(12) United States Patent
Moore et al.

(10) Patent No.: US 12,377,077 B2
(45) Date of Patent: Aug. 5, 2025

(54) METHODS AND FORMULATIONS TO TREAT MITOCHONDRIAL DYSFUNCTION

(71) Applicant: The Board of Trustees of the Leland Stanford Junior University, Stanford, CA (US)

(72) Inventors: Tereza Moore, Palo Alto, CA (US); Tina M. Cowan, Palo Alto, CA (US); Gregory M. Enns, Palo Alto, CA (US); Mehrdad Shamloo, Stanford, CA (US); Michael J. Green, Half Moon Bay, CA (US); Alam Jahangir, San Jose, CA (US); Rolando E. Yanes, Santa Clara, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1072 days.

(21) Appl. No.: 17/419,477

(22) PCT Filed: Dec. 31, 2019

(86) PCT No.: PCT/US2019/069145
§ 371 (c)(1),
(2) Date: Jun. 29, 2021

(87) PCT Pub. No.: WO2020/142547
PCT Pub. Date: Jul. 9, 2020

(65) Prior Publication Data
US 2022/0071963 A1 Mar. 10, 2022

Related U.S. Application Data

(60) Provisional application No. 62/786,970, filed on Dec. 31, 2018.

(51) Int. Cl.
| | |
|---|---|
| A61K 31/4184 | (2006.01) |
| A61K 31/05 | (2006.01) |
| A61K 31/155 | (2006.01) |
| A61K 31/194 | (2006.01) |
| A61K 31/404 | (2006.01) |
| A61K 31/41 | (2006.01) |
| A61K 31/4155 | (2006.01) |
| A61K 31/422 | (2006.01) |
| A61K 31/4245 | (2006.01) |
| A61K 31/427 | (2006.01) |
| A61K 31/433 | (2006.01) |
| A61K 31/4365 | (2006.01) |
| A61K 31/437 | (2006.01) |
| A61K 31/4439 | (2006.01) |
| A61K 31/505 | (2006.01) |
| A61K 31/618 | (2006.01) |
| A61K 31/706 | (2006.01) |

(52) U.S. Cl.
CPC .......... *A61K 31/4184* (2013.01); *A61K 31/05* (2013.01); *A61K 31/155* (2013.01); *A61K 31/194* (2013.01); *A61K 31/404* (2013.01); *A61K 31/41* (2013.01); *A61K 31/4155* (2013.01); *A61K 31/422* (2013.01); *A61K 31/4245* (2013.01); *A61K 31/427* (2013.01); *A61K 31/433* (2013.01); *A61K 31/4365* (2013.01); *A61K 31/437* (2013.01); *A61K 31/4439* (2013.01); *A61K 31/505* (2013.01); *A61K 31/618* (2013.01); *A61K 31/706* (2013.01)

(58) Field of Classification Search
CPC .. A61K 31/4184; A61K 31/05; A61K 31/155; A61K 31/194; A61K 31/404; A61K 31/41; A61K 31/4155; A61K 31/422; A61K 31/4245; A61K 31/427; A61K 31/433; A61K 31/465; A61K 31/437; A61K 31/4439; A61K 31/505; A61K 31/618; A61K 31/706
See application file for complete search history.

(56) References Cited

U.S. PATENT DOCUMENTS

| | | |
|---|---|---|
| 2013/0267493 A1 | 10/2013 | Bhattacharya et al. |
| 2017/0145034 A1 | 5/2017 | Blaquiere et al. |
| 2017/0182076 A1 | 6/2017 | Alvarez et al. |

FOREIGN PATENT DOCUMENTS

| | | |
|---|---|---|
| JP | 2016-533385 A | 10/2016 |
| WO | WO 2014/180908 A1 | 11/2014 |
| WO | WO 2018/118808 A1 | 6/2018 |

OTHER PUBLICATIONS

Registry No. 1658466-10-4, File Registry on STN, entered Mar. 9, 2015.*
International Search Report and Written Opinion for PCT/US2019/069145. Mailed Jun. 3, 2020. 19 pages.
Arad et al., AMP-activated protein kinase in the heart: role during health and disease. Circ Res. Mar. 2, 2007;100(4):474-88.

(Continued)

*Primary Examiner* — Rebecca L Anderson
(74) *Attorney, Agent, or Firm* — Casimir Jones, S.C.; Anne M. Reynolds

(57) ABSTRACT

Methods of treatment and pharmaceutical formulations configured to treat primary and secondary mitochondrial dysfunction are provided. The methods and treatments use an agonist of AMPK. The agonist activates AMPK to activate ATP-producing pathways and inhibiting ATP-consuming pathways, thus allowing for the alleviation of symptoms associated with mitochondrial dysfunctions.

17 Claims, 34 Drawing Sheets

(56) References Cited

OTHER PUBLICATIONS

Atkuri et al., Inherited disorders affecting mitochondrial function are associated with glutathione deficiency and hypocitrullinemia. Proc Natl Acad Sci U S A. Mar. 10, 2009;106(10):3941-5.

Calaza et al., Mitochondrial decline precedes phenotype development in the complement factor H mouse model of retinal degeneration but can be corrected by near infrared light. Neurobiol Aging. Oct. 2015;36(10):2869-76.

Cameron et al., Discovery and Preclinical Characterization of 6-Chloro-5-[4-(1-hydroxycyclobutyl)phenyl]-1H-indole-3-carboxylic Acid (PF-06409577), a Direct Activator of Adenosine Monophosphate-activated Protein Kinase (AMPK), for the Potential Treatment of Diabetic Nephropathy. J Med Chem. Sep. 8, 2016;59(17):8068-81.

Chinnery et al., Treatment for mitochondrial disorders. Cochrane Database Syst Rev. Jan. 25, 2006;(1):CD004426. 24 pages.

Cokorinos et al., Activation of Skeletal Muscle AMPK Promotes Glucose Disposal and Glucose Lowering in Non-human Primates and Mice. Cell Metab. May 2, 2017;25(5):1147-1159.e10.

Cool et al., Identification and characterization of a small molecule AMPK activator that treats key components of type 2 diabetes and the metabolic syndrome. Cell Metab. Jun. 2006;3(6):403-16.

Enns et al., Degree of glutathione deficiency and redox imbalance depend on subtype of mitochondrial disease and clinical status. PLoS One. Jun. 18, 2014;9(6):e100001. 9 pages.

Golubitzky et al., Screening for active small molecules in mitochondrial complex I deficient patient's fibroblasts, reveals AICAR as the most beneficial compound. PLoS One. 2011;6(10):e26883. 9 pages.

Hawley et al., The ancient drug salicylate directly activates AMP-activated protein kinase. Science. May 18, 2012;336(6083):918-22.

Hunter et al., Mechanism of action of compound-13: an α1-selective small molecule activator of AMPK. Chem Biol. Jul. 17, 2014;21(7):866-79.

Jobst et al., Glycosylated protein in lipofuscin. J Clin Pathol. May 1991;44(5):437-8.

Kim et al., AMPK activators: mechanisms of action and physiological activities. Exp Mol Med. Apr. 1, 2016;48(4):e224. 12 pages.

Li et al., Novel small-molecule AMPK activator orally exerts beneficial effects on diabetic db/db mice. Toxicol Appl Pharmacol. Dec. 1, 2013;273(2):325-34.

Meltzer-Mats et al., Synthesis and mechanism of hypoglycemic activity of benzothiazole derivatives. J Med Chem. Jul. 11, 2013;56(13):5335-50.

Myers et al., Systemic pan-AMPK activator MK-8722 improves glucose homeostasis but induces cardiac hypertrophy. Science. Aug. 4, 2017;357(6350):507-511.

Pang et al., Small molecule antagonizes autoinhibition and activates AMP-activated protein kinase in cells. J Biol Chem. Jun. 6, 2008;283(23):16051-60.

Pfeffer et al., Treatment for mitochondrial disorders. Cochrane Database Syst Rev. Apr. 18, 2012;2012(4):CD004426. 39 pages.

Pinkosky et al., Liver-specific ATP-citrate lyase inhibition by bempedoic acid decreases LDL-C and attenuates atherosclerosis. Nat Commun. Nov. 28, 2016;7:13457.

Schon et al., Neuronal degeneration and mitochondrial dysfunction. J Clin Invest. Feb. 2003;111(3):303-12.

Xi et al., Novel direct AMPK activator suppresses non-small cell lung cancer through inhibition of lipid metabolism. Oncotarget. Oct. 9, 2017;8(56):96089-96102.

Xiao et al., Structural basis of AMPK regulation by small molecule activators. Nat Commun. 2013;4:3017. 10 pages.

Yang et al., Analysis of mouse models of cytochrome c oxidase deficiency owing to mutations in Sco2. Hum Mol Genet. Jan. 1, 2010;19(1):170-80.

Zadra et al., A novel direct activator of AMPK inhibits prostate cancer growth by blocking lipogenesis. EMBO Mol Med. Apr. 2014;6(4):519-38.

Zhang et al., Human gut microbiota changes reveal the progression of glucose intolerance. PLoS One. Aug. 20, 2013;8(8) 11 pages.

Office Action for JP 2021-538362, mailed Nov. 28, 2023, 2 pages. With English Translation.

Office Action for CN 201980087513.1, mailed Dec. 1, 2023, 10 pages. With English Translation.

Office Action for CA 3124838, mailed Nov. 27, 2023, 5 pages.

\* cited by examiner

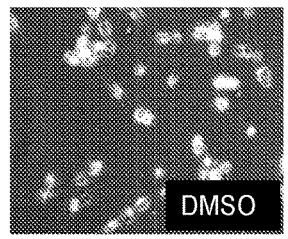 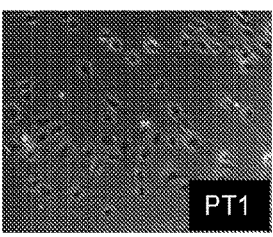 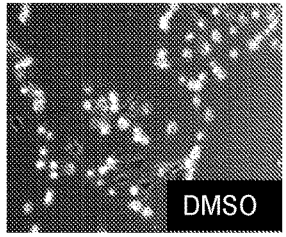 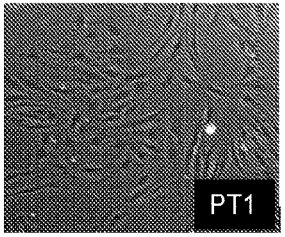
Fig. 3A  Fig. 3B  Fig. 3C  FIG. 3D
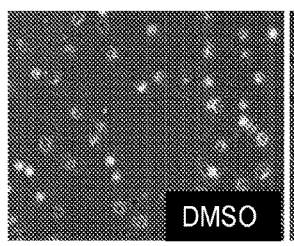 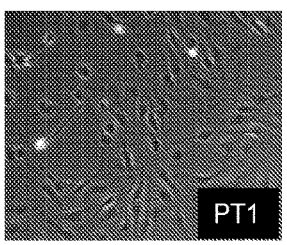 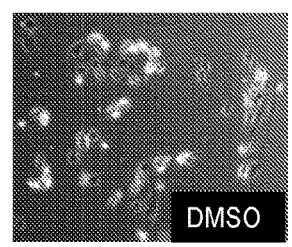 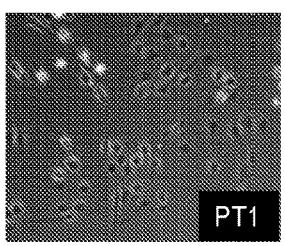
Fig. 3E  Fig. 3F  Fig. 3G  FIG. 3H
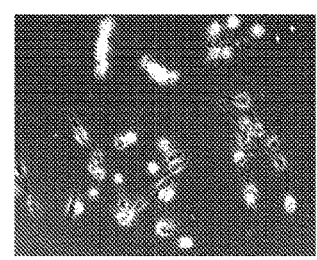 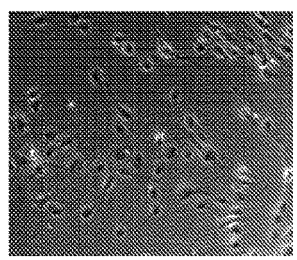
Fig. 3I  Fig. 3J Step 1

Step 2

Step 3

METHODS AND FORMULATIONS TO TREAT MITOCHONDRIAL DYSFUNCTION

CROSS REFERENCE TO RELATED APPLICATIONS

This application is a national stage filing under 35 U.S.C. § 371 of International Patent Application No. PCT/US2019/069145, filed on Dec. 31, 2019, which claims priority to U.S. Provisional Application Ser. No. 62/786,970, entitled "Methods and Formulations to Treat Mitochondrial Dysfunction" to Moore et al., filed Dec. 31, 2018; the disclosures of each of which are herein incorporated by reference in their entireties.

FIELD OF THE INVENTION

The present invention relates to methods of treatment and pharmaceutical formulations to treat primary and secondary mitochondrial dysfunction.

BACKGROUND

Previously studied drug candidates were conventional AMP-dependent AMPK activators, with the mechanism of action requiring elevations of AMP caused either by RC inhibition (e.g., metformin, resveratrol) or conversion into AMP mimetics (e.g., AICAR). The indirect mechanism involving RC inhibition is not suitable for cases with underlying mitochondrial dysfunction, and AMP-dependent activation of AMPK results in the activation of other AMP-regulated enzymes, thereby compounding pleiotropic effects. Additionally, previous studies have identified direct, AMP-independent AMPK agonists for the purpose of treating diabetes, obesity, and metabolic syndrome.

Primary mitochondrial diseases are a clinically heterogeneous group of disorders that are usually progressive, multisystemic, and are associated with a high mortality rate in children. They are caused by inherited deficiencies in the mitochondrial respiratory chain (RC), leading to an increased production of reactive oxygen and nitrogen species (ROS and RNS) as well as a deficiency in overall energy production. These resulting metabolic imbalances lead to cellular damage and ultimately to cell death.

There is currently no curative treatment for primary mitochondrial disease. Only supportive treatment is available and involves treating specific symptoms (e.g., Diabetes, cardiac disease, and ptosis) and a "mitochondrial cocktail" consisting of vitamin cofactors and antioxidants. Unfortunately, meta-analyses have shown that the available supportive interventions lacks efficacy, highlighting the need for a novel treatment. (See, e.g., Pfeffer et al, Cochrane Database Sys Rev. 2012 Apr. 18; 4; Chinnery et al, 2006, Cochrane Database Sys Rev. 2006 Jan. 25; (1); the disclosures of which are incorporated herein by reference in their entirety).

Secondary mitochondrial diseases also demonstrate mitochondrial dysfunction but, unlike primary mitochondrial diseases, are not caused by genes related to the mitochondrial respiratory chain. Secondary mitochondrial diseases, such as Parkinson's disease or Alzheimer's disease, are due to acquired mitochondrial abnormalities caused by other diseases, conditions, or environmental factors that indirectly damage the mitochondria. Consequently, any treatment identified for primary mitochondrial disease, would be expected to also benefit disorders and conditions associated with secondary mitochondrial dysfunction, including neurodegenerative, neuromuscular, and muscle wasting disorders.

SUMMARY OF THE INVENTION

Methods and Formulations to treat mitochondrial dysfunction in accordance with embodiments of the invention are disclosed.

In one embodiment, a method of treating a patient with mitochondrial dysfunction includes identifying a mitochondrial dysfunction in an individual and providing an AMPK agonist to the individual.

In another embodiment, the mitochondrial dysfunction is a primary mitochondrial dysfunction.

In a further embodiment, the primary mitochondrial dysfunction is selected from the group consisting of Autosomal Dominant Optic Atrophy (ADOA), Alpers-Huttenlocher syndrome (nDNA defect), Ataxia neuropathy syndrome, (nDNA defect), Barth syndrome/Lethal Infantile Cardiomyopathy (LIC), Co-enzyme Q deficiency, Complex I, complex II, complex III, complex IV and complex V deficiencies (either single deficiencies or any combination of deficiency), Chronic progressive external ophthalmoplegia (CPEO), Diabetes mellitus and deafness, Kearns-Sayre syndrome (mtDNA defect), Leukoencephalopathy with Brainstem and Spinal Cord Involvement and Lactate Elevation (LBSL-leukodystrophy), Leigh syndrome (mtDNA and nDNA defects), Leber's hereditary optic neuropathy (LHON), Luft Disease, Mitochondrial myopathy, encephalopathy, lactic acidosis, and stroke syndrome (MELAS) (mtDNA defect), Mitochondrial Enoyl CoA Reductase Protein-Associated Neurodegeneration (MEPAN), Myoclonic epilepsy with ragged red fibers (MERRF), mitochondrial recessive ataxia syndrome (MIRAS), mtDNA deletion syndrome, mtDNA Depletion syndrome, mtDNA maintenance disorders, mtDNA/RNA translation defects, Mitochondrial tRNA synthetase deficiencies, Mitochondrial Myopathy, Mitochondrial neurogastrointestinal encephalopathy syndrome (MNGIE), Neurogenic muscle weakness, ataxia, and retinitis pigmentosa (NARP), Pearson syndrome, Pyruvate dehydrogenase complex deficiency (PDCD/PDH), DNA polymerase gamma deficiency (POLG), Pyruvate carboxylase deficiency, and Thymidine kinase 2 deficiency (TK2).

In still a further embodiment, the mitochondrial dysfunction is a secondary mitochondrial dysfunction.

In still another embodiment, the secondary mitochondrial dysfunction is selected from the group consisting of Amyotrophic Lateral Sclerosis (ALS), Alzheimer's disease (AD) and other dementias, Friedreich's ataxia (FA), Huntington's disease (HD), Motor neuron diseases (MND), N-glycanase deficiency (NGLY1), Organic acidemias, Parkinson's disease (PD) and PD-related disorders, Prion disease, Spinal muscular atrophy (SMA), Spinocerebellar ataxia (SCA), Becker muscular dystrophy, Congenital muscular dystrophies, Duchenne muscular dystrophy, Emery-Dreifuss muscular dystrophy, Facioscapulohumeral muscular dystrophy, Myotonic dystrophy, Oculopharyngeal muscular dystrophy, Charcot-Marie-Tooth disease, Congenital myopathies, Distal myopathies, Endocrine myopathies (hyperthyroid myopathy, hypothyroid myopathy), Giant axonal neuropathy, Hereditary spastic paraplegia, Inflammatory myopathies (dermatomyositis, inclusion-body myositis, polymyositis), Metabolic myopathies, Neuromuscular junction diseases: Autism, Cancer, Diabetes, Metabolic syndrome, Chronic fatigue syndrome, an inflammatory disorder, arthritis, and aging.

In yet another embodiment, the AMPK agonist is a direct AMPK agonist.

In a further embodiment again, the direct AMPK agonist is selected from the group consisting of PT1, ETC-1002, Salicylate, C991, C13, D561-0775, MT 63-78, A-769662, ZLN024, C24, MK-8722, PF-739, and PF-06409577.

In another embodiment again, the AMPK agonist is an AMP-dependent agonist.

In a further additional embodiment, the AMP-dependent agonist is selected from the group consisting of metformin, resveratrol, and AICAR.

In another additional embodiment, the AMPK agonist is provided in a pharmaceutical formulation.

In a still yet further embodiment, the pharmaceutical formulation comprises the AMPK agonist and at least one of the group consisting of a binding agent, a lubricating agent, a buffer, and a coating.

In still yet another embodiment, the providing step comprises orally administering the AMPK agonist to the individual.

In a still further embodiment again, the providing step comprises administering the AMPK agonist daily for at least one week.

In still another embodiment again, the method further includes assessing the efficacy of the AMPK agonist in the individual.

In a still further additional embodiment, the providing step is accomplished by administrating the AMPK agonist by at least one of the group consisting of: oral administration, subcutaneous administration, intravenous administration, intraperitoneal administration, intranasal administration, dermal administration, and inhalation.

In still another additional embodiment, a method of treating mitochondrial disorders includes identifying a disorder in an individual and modulating AMPK activity in the individual.

In a yet further embodiment again, the modulating step is accomplished by activating AMPK in the individual.

In yet another embodiment again, the activating step is accomplished by phosphorylating AMPK or providing an agonist to AMPK.

In a yet further additional embodiment, the modulating step is accomplished by inhibiting AMPK in the individual.

In yet another additional embodiment, the disorder is associated with mitochondrial dysfunction.

In a further additional embodiment again, the mitochondrial dysfunction is a primary mitochondrial dysfunction.

In another additional embodiment again, the mitochondrial dysfunction is a secondary mitochondrial dysfunction.

In a still yet further embodiment again, an AMPK agonist includes a molecule of formula

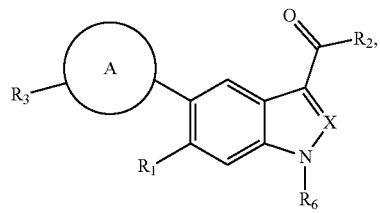

where:
A is selected from a 5-membered ring heterocyclic, either unsubstituted or substituted with one or more $C_{1-6}$ alkyl or fluoro substituents X is $CR_5$ or N;

$R_1$ is H, $CF_3$, or halo;

$R_2$ is $OR_5$, NHOH, $NHSO_2R_4$, $OCH_2OCOR_4$, or $COR_2$ is a C-linked tetrazole, $R_3$ is $C_{1-10}$ alkyl, $C_{3-7}$ cycloalkyl, $C_{4-12}$ alkylcycloalkyl, $C_{4-10}$ cycloalkylalkyl, $C_{3-7}$ heterocycloalkyl, $C_{4-12}$ alkylheterocycloalkyl, $C_{4-10}$ heterocycloalkylalkyl, aryl or heteroaryl either unsubstituted or substituted with one to three substituents selected from halo, OH and $OCOR_7$;

$R_4$ is $C_{1-10}$ alkyl, $C_{3-7}$ cycloalkyl, $C_{4-12}$ alkylcycloalkyl, $C_{4-10}$ cycloalkylalkyl either unsubstituted or substituted with one to three halogen substituents;

$R_5$ is $R_4$ or H;

$R_6$ is H, $C_{1-6}$ alkyl, $C_{3-6}$ cycloalkyl, or two $R_6$ groups, together with the nitrogen atom to which they are attached can form a four to seven membered heterocycloalkyl ring, all of which can be optionally substituted with 1 to 3 fluorine atoms; and $R_7$ is $C_{1-10}$ alkyl, $C_{3-7}$ cycloalkyl, $C_{4-12}$ alkylcycloalkyl unsubstituted or substituted with one to three substituents selected from fluoro, $C_{1-10}$ alkyl, and $NR_6$, $R_6$.

In still yet another embodiment again, A is selected from the group consisting of

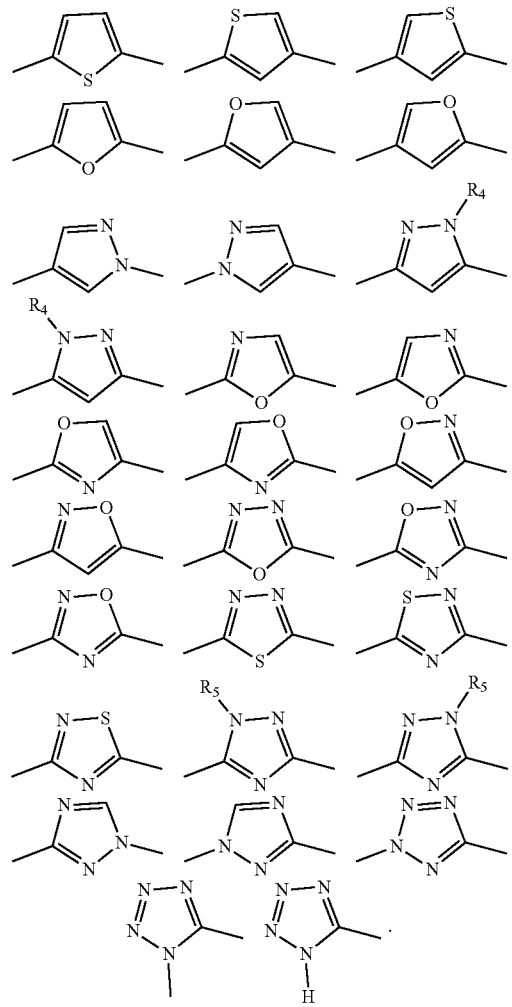

In a still yet further additional embodiment, A is selected from the group consisting of:

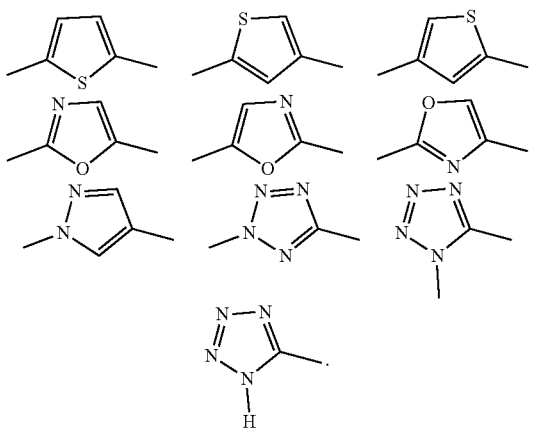

In still yet another additional embodiment, A is selected from the group consisting of:

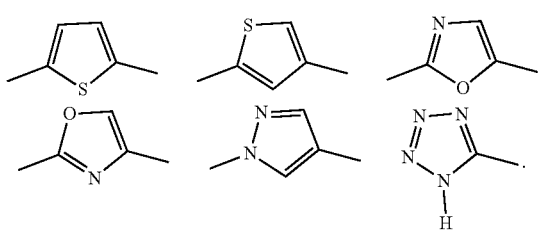

In a yet further additional embodiment again, X is CH, $R_6$ is H, $R_1$ is Cl, and $R_2$ is OH.

In yet another additional embodiment again, the molecule has a formula as illustrated in one of FIGS. 13A-13Z and FIGS. 14A-14O.

In a still yet further additional embodiment again, the molecule has the formula:

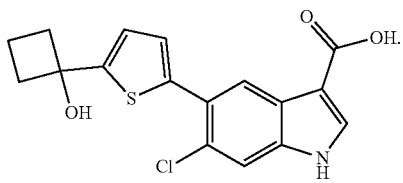 [SMILES: O=C(O)c1c[nH]c2cc(Cl)c(-c3ccc(C4(O)CCC4)s3)cc12]

In still yet another additional embodiment again, an AMPK agonist includes a molecule of formula:

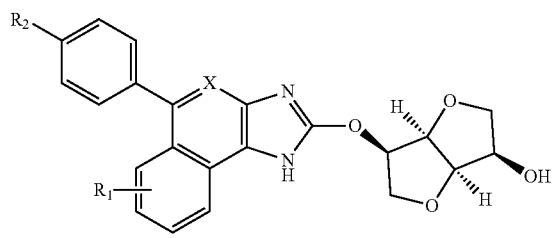

where:
X is CH or N;
$R_1$ is small alkyl (C1-C4) or halogen (e.g., Cl, Br, or F);
$R_2$ is phenyl, alkyl C1-C10, cycloalkyl (C3-C10), hydroxyalkyl (C1-C6), heteroaromatic (e.g., pyridyl, pyrazolyl, pyrolyl, pyrimidyl, thiophenyl, furanyl, or triazole), or heterocyclic C4-C6;
where phenyl is optionally substituted with halogens (e.g., Cl, Br, or F),
where an alkyl is linear or branched and optionally substituted with OH, OMe, OEt,
where cycloalkyl is optionally substituted with one or more OH,
where hydroxy alkyl is linear or branched
where heteroaromatic is optionally substituted with small alkyls (C1-C6) or hydroxyalkyls (C1-C6), where alkyls and hydroxyalkyls are linear or branched,
where heteroatom in hetrocyclic is optionally O, S, or $NR_4$, where $R_4$ is
a linear or branched C1-C6 alkyl or hydroxyalkyl; and
$R_4$ is a linear or branched C1-C6 alkyl or hydroxyalkyl.

In another further embodiment, the molecule has the formula of:

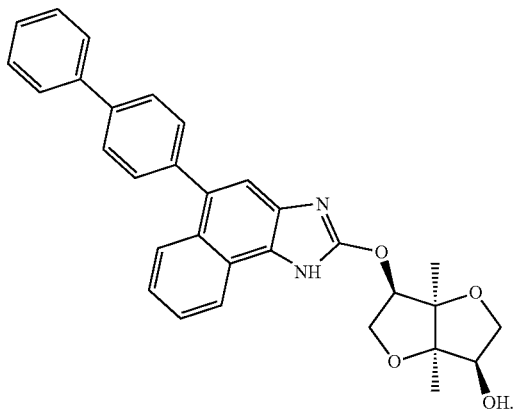 [SMILES: C[C@]12OC[C@@H](Oc3nc4cc(-c5ccc(-c6ccccc6)cc5)c5ccccc5c4[nH]3)[C@@]1(C)OC[C@H]2O]

In still another further embodiment, an AMPK agonist includes a molecule of formula:

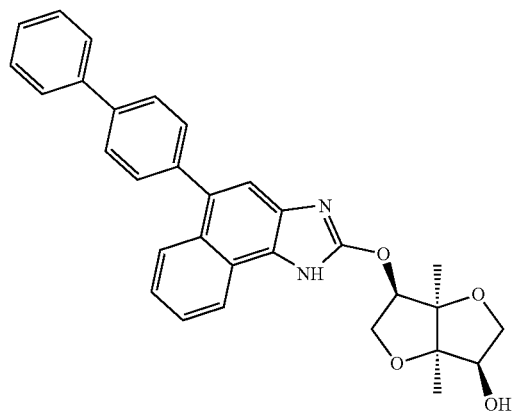

where:
A is a fused ring (e.g., C3-C10 cycloalkyl);
X is CH or N;
Y is O, S, NH, NR$_3$;
R$_1$ is small alkyl (C1-C4) or halogen (e.g., Cl, Br, or F);
R$_2$ is phenyl, alkyl C1-C10, cycloalkyl (C3-C10), hydroxyalkyl (C1-C6), heteroaromatic (e.g., pyridyl, pyrazolyl, pyrolyl, pyrimidyl, thiophenyl, furanyl, or triazole), or heterocyclic C4-C6;
  where phenyl is optionally substituted with halogens (e.g., Cl, Br, or F), where an alkyl is linear or branched and optionally substituted with OH, OMe, OEt,
  where cycloalkyl is optionally substituted with one or more OH,
  where hydroxy alkyl is linear or branched
  where heteroaromatic is optionally substituted with small alkyls (C1-C6) or hydroxyalkyls (C1-C6), where alkyls and hydroxyalkyls are linear or branched,
  where heteroatom in hetrocyclic is optionally O, S, or NR$_4$;
R$_3$ is a C1-C6 alkyl (linear or branched); and
R$_4$ is a linear or branched C1-C6 alkyl or hydroxyalkyl.

In yet another further embodiment, A is selected from a C6 phenyl ring or one of the following:

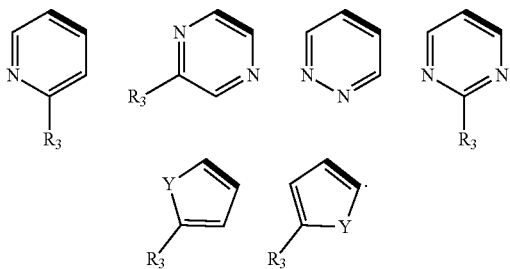

In another further embodiment again, the molecule has the formula of:

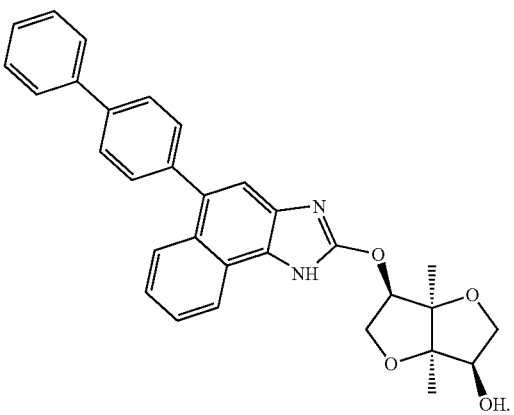 [SMILES: C[C@]12OC[C@@H](Oc3nc4cc(-c5ccc(-c6ccccc6)cc5)c5ccccc5c4[nH]3)[C@@]1(C)OC[C@H]2O]

BRIEF DESCRIPTION OF THE DRAWINGS

These and other features and advantages of the present invention will be better understood by reference to the following detailed description when considered in conjunction with the accompanying drawings where.

DETAILED DESCRIPTION

Figure 1A:
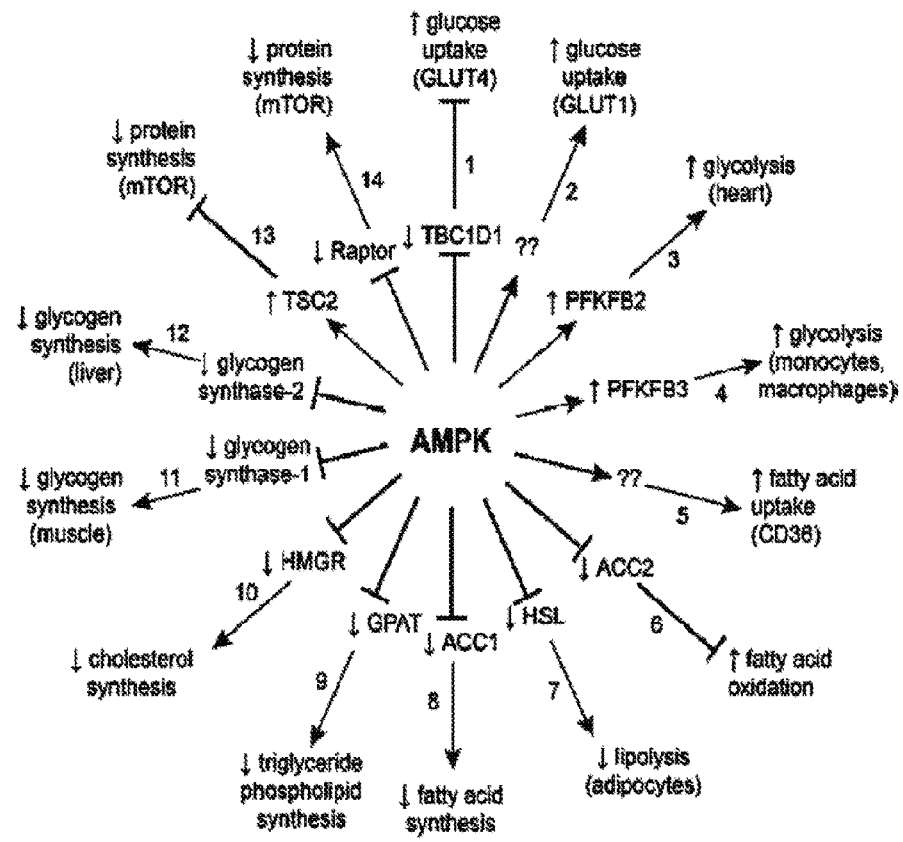
FIG. 1A illustrates pathways activated and inhibited by AMPK in accordance with various embodiments.
Figure 1A:
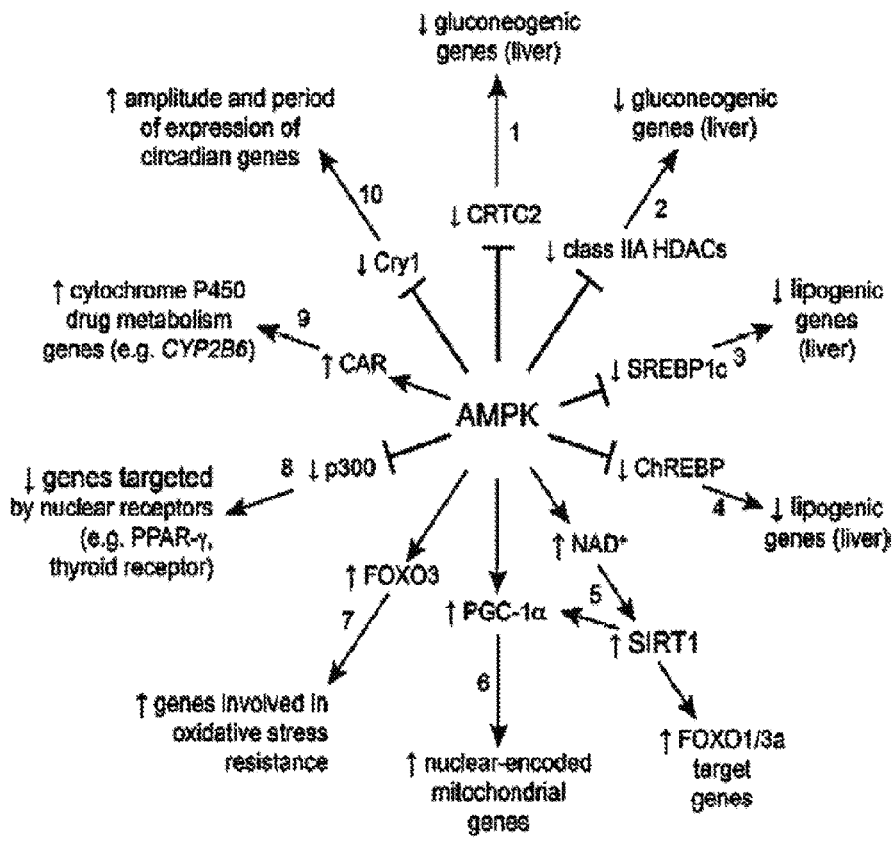
Figure 1B:
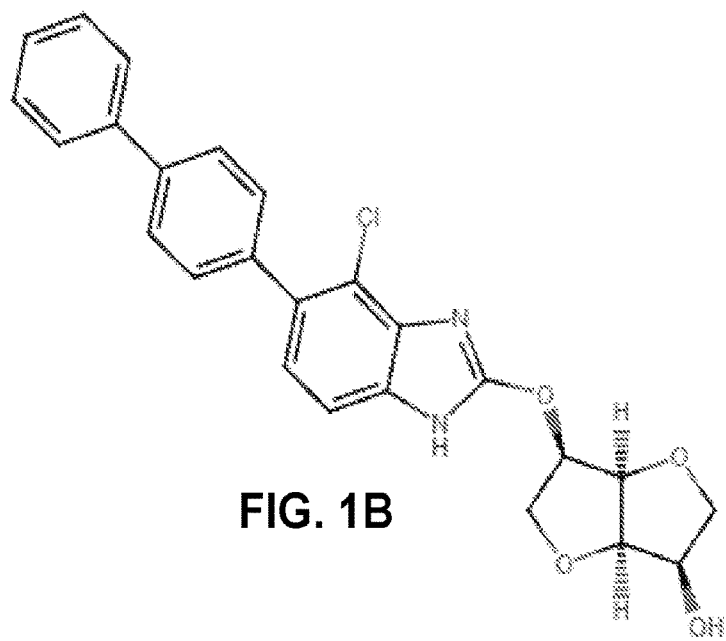
FIGS. 1B-1D illustrate structures of AMPK agonists in accordance with various embodiments.
Figure 1C:
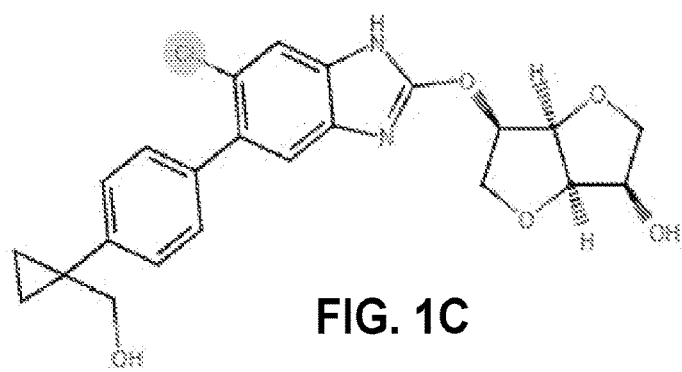
Figure 1D:
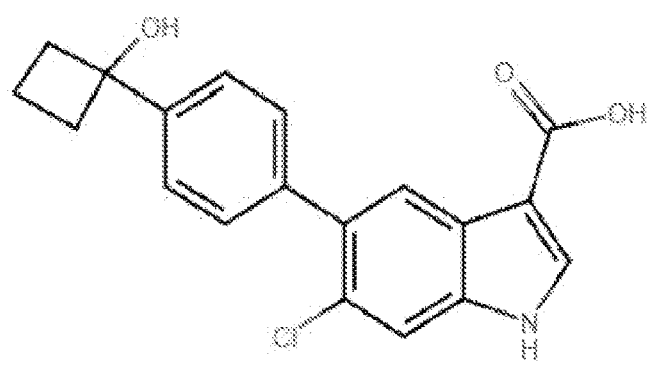

Turning now to the data and description, methods of treatment, and pharmaceutical formulations configured to treat mitochondrial disorders, diseases, and/or dysfunctions are described. In various embodiments, the methods and formulations use agonists of AMP-activated protein kinase (AMPK). AMPK is a master regulator of cellular energy homeostasis and is activated during energy deficiency to restore adenosine triphosphate (ATP) levels. Generally, AMPK restores energy homeostasis by activating ATP-producing pathways (e.g., Glycolysis, mitochondrial biogenesis) and inhibiting ATP-consuming pathways (e.g., Gluconeogenesis and fatty acid synthesis). Additional pathways or processes promoted by AMPK include antioxidant enzymes, autophagy, fatty acid metabolism, and muscle regeneration.

FIG. 1 illustrates a variety of pathways activated or inhibited by AMPK. AMPK's regulation of glucose and fatty acid pathway has made it an attractive therapeutic target for diabetes, obesity and metabolic syndrome, leading to the identification of AMPK agonists for this purpose.

To combat the defects in indirect AMPK agonists, certain embodiments are directed to direct, AMP-independent AMPK agonists to treat disorders and conditions with underlying mitochondrial dysfunction. Direct AMPK activating compounds, including PT1, ETC-1002, Salicylate, C991, C13, D561-0775, MT 63-78, A-769662, ZLN024, C24, MK-8722 (FIG. 1B), PF-739 (FIG. 1C), and PF-06409577 (FIG. 1D) allosterically activate AMPK by directly binding to either the alpha or beta subunit, and in some cases were shown to improve lipid and glucose profiles in vivo. (See e.g., Cool et al, Cell Metab. 2006 June; 3(6):403-16; Pang et al, J Biol Chem. 2008 Jun. 6; 283(23):16051-60; Hawley et al, Science. 2012 May 18; 336(6083):918-22; Li et al, Toxicol Appl Pharmacol. 2013 Dec. 1; 273(2):325-34; Zhang et al, PLoS One. 2013 Aug. 20; 8(8); Xiao et al, Nat Commun. 2013; 4:3017; Zadra et al, EMBO Mol Med. 2014 April; 6(4):519-38; Hunter et al, Chem Biol. 2014 Jul. 17; 21(7):866-79; Pinkosky et al, Nat Commun. 2016 Nov. 28; 7:13457; Cameron et al, 2016 Sep 8; 59(17):8068-81; Myers et al, Science. 2017 Aug. 4; 357(6350):507-511; Cokorinos et al, Cell Metab. 2017 May 2; 25(5):1147-1159; Xi et al, Oncotarget. 2017 Nov. 10; 8(56): 96089-96102; the disclosures of which are incorporated herein by reference in their entirety.)

Treatments using various embodiments of direct AMPK agonists increase cellular respiration and ATP levels and reduce oxidative stress, resulting in consistent and effective improvement in viability of cells from patients with both primary and secondary mitochondrial disease, including a wide-range of disorders and conditions associated with secondary mitochondrial dysfunction. Diseases and disorders associated with primary and secondary mitochondrial dysfunction are listed in Tables 1 and 2, respectively. Additionally, direct AMPK agonists provide protection against retinal degeneration in age related macular degeneration (AMD), neuroprotectivity in ischemic stroke, and is sufficient to enhance motor performance. Further, direct AMPK agonists mitigate known negative effects, such as retinal damage, neuronal degeneration and muscle wasting, associated with mitochondrial dysfunction in both primary and secondary mitochondrial disorders. As such, certain embodiments are directed to the treatment of N-glycanase (NGLY1) deficiency, age-related macular degeneration (AMD), ischemic stroke, muscular dystrophies (e.g., Duchenne and Becker), Friedreich ataxia (FA), autoimmune disorders with muscle involvement (e.g., inclusion body myositis, Polymyositis, and Dermatomyositis), and/or neurodegenerative disorders (e.g., Amyotrophic Lateral Sclerosis (ALS), Parkinson's Disease, and Alzheimer's Disease). Additionally, AMPK activation in cardiac tissue can result in reversible cardiac hypertrophy, thus various embodiments are directed to the treat diseases associated with dilated cardiomyopathy. (See, e.g., Arad et al, Circ Res. 2007 Mar. 2; 100(4):474-88; Myers et al, Science. 2017 Aug. 4; 357(6350):507-511; the disclosures of which are incorporated herein by reference in their entirety.)

TABLE 1

Diseases and disorders associated with primary mitochondrial dysfunction

Autosomal Dominant Optic Atrophy (ADOA)
Alpers-Huttenlocher syndrome (nDNA defect)
Ataxia neuropathy syndrome, (nDNA defect)
Barth syndrome/Lethal Infantile Cardiomyopathy (LIC)
Co-enzyme Q deficiency
Complex I, complex II, complex III, complex IV and complex V deficiencies (either single deficiencies or any combination of deficiency)
Chronic progressive external ophthalmoplegia (CPEO)
Diabetes mellitus and deafness
Kearns-Sayre syndrome (mtDNA defect)
Leukoencephalopathy with Brainstem and Spinal Cord Involvement and Lactate Elevation (LBSL-leukodystrophy)
Leigh syndrome (mtDNA and nDNA defects)
Leber's hereditary optic neuropathy (LHON)
Luft Disease
Mitochondrial myopathy, encephalopathy, lactic acidosis, and stroke syndrome (MELAS) (mtDNA defect)
Mitochondrial Enoyl CoA Reductase Protein-Associated Neurodegeneration (MEPAN)
Myoclonic epilepsy with ragged red fibers (MERRF)
mitochondrial recessive ataxia syndrome (MIRAS)
mtDNA deletion syndrome
mtDNA Depletion syndrome
mtDNA maintenance disorders
mtDNA/RNA translation defects
Mitochondrial tRNA synthetase deficiencies

TABLE 1-continued

Diseases and disorders associated with primary mitochondrial dysfunction

Mitochondrial Myopathy
Mitochondrial neurogastrointestinal encephalopathy syndrome (MNGIE)
Neurogenic muscle weakness, ataxia, and retinitis pigmentosa (NARP)
Pearson syndrome
Pyruvate dehydrogenase complex deficiency (PDCD/PDH)
DNA polymerase gamma deficiency (POLG)
Pyruvate carboxylase deficiency
Thymidine kinase 2 deficiency (TK2)

TABLE 2

Diseases and disorders associated with secondary mitochondrial dysfunction

Neurodegenerative:

Amyotrophic Lateral Sclerosis (ALS)
Alzheimer's disease (AD) and other dementias
Friedreich's ataxia (FA)
Huntington's disease (HD)
Motor neuron diseases (MND)
N-glycanase deficiency (NGLY1)
Organic acidemias
Parkinson's disease (PD) and PD-related disorders
Prion disease
Spinal muscular atrophy (SMA)
Spinocerebellar ataxia (SCA)

Muscular dystrophies:

Becker muscular dystrophy
Congenital muscular dystrophies
Duchenne muscular dystrophy
Emery-Dreifuss muscular dystrophy
Facioscapulohumeral muscular dystrophy
Myotonic dystrophy
Oculopharyngeal muscular dystrophy Myopathies:

Charcot-Marie-Tooth disease
Congenital myopathies
Distal myopathies
Endocrine myopathies (hyperthyroid myopathy, hypothyroid myopathy)
Giant axonal neuropathy
Hereditary spastic paraplegia
Inflammatory myopathies (dermatomyositis, inclusion-body myositis, polymyositis)
Metabolic myopathies
Neuromuscular junction diseases:

Other:

Autism
Cancer
Diabetes
Metabolic syndrome
Chronic fatigue syndrome
Inflammatory disorders (e.g., arthritis)
Aging (e.g., lifespan)

Characterization of AMPK Agonist Properties

Properties of selected AMPK agonists are provided below to characterize the performance of exemplary embodiments of the invention. Although some specific agonists are discussed, it will be understood that the results are meant only to provide an overview of agonist functions and are not meant to be limiting.

Effect of Direct AMPK Agonists on Cell Viability and Morphology

Figure 2A:
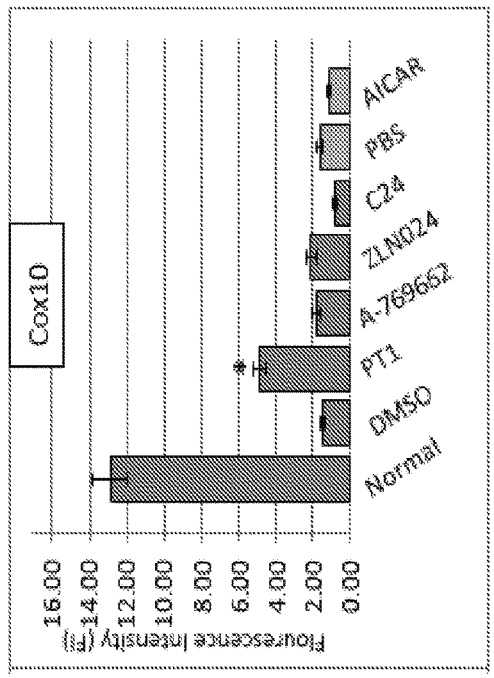
FIGS. 2A-2F illustrate results of cell viability assays under various treatments in accordance with various embodiments.
Figure 2B:
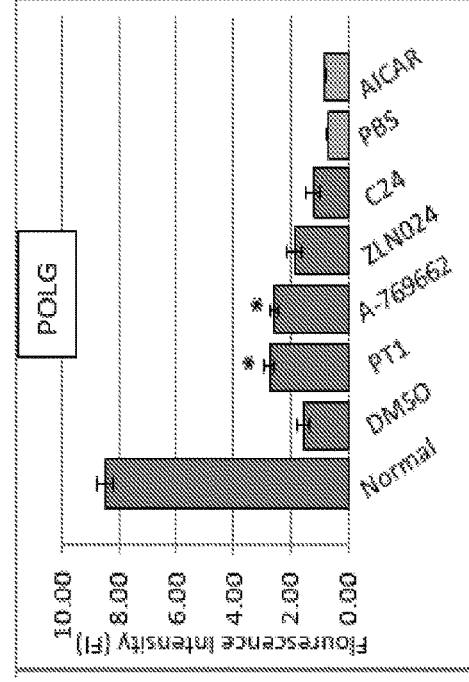
Figure 2C:
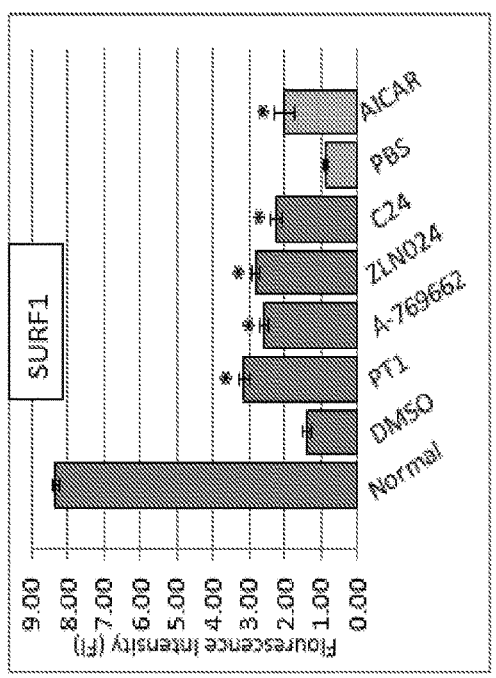
Figure 2D:
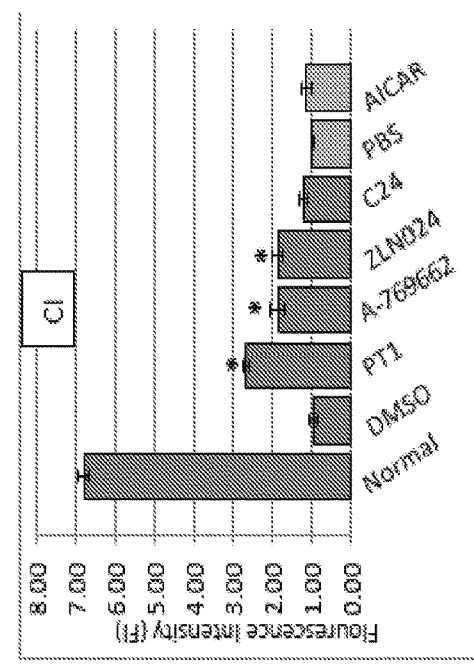
Figure 2E:
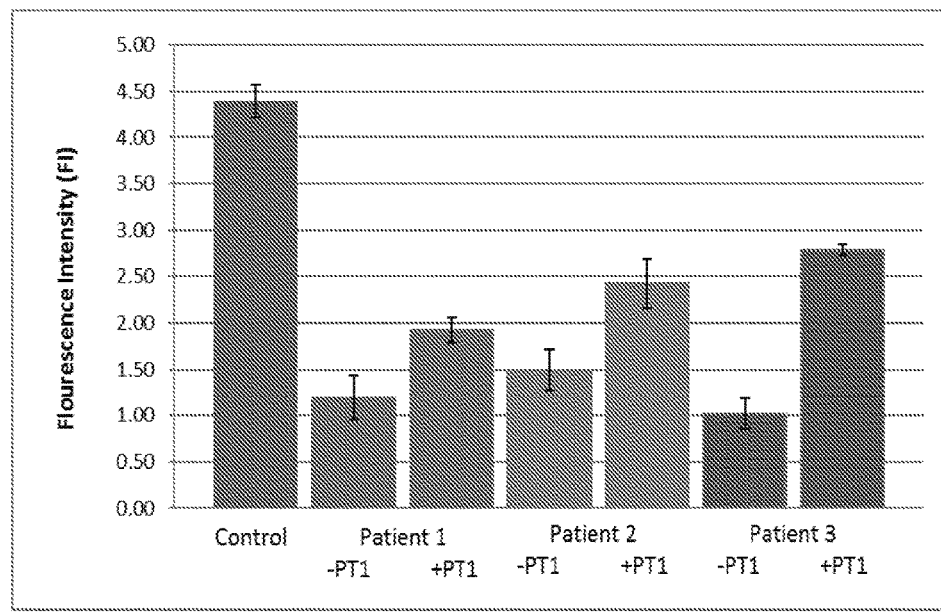
Figure 2F:
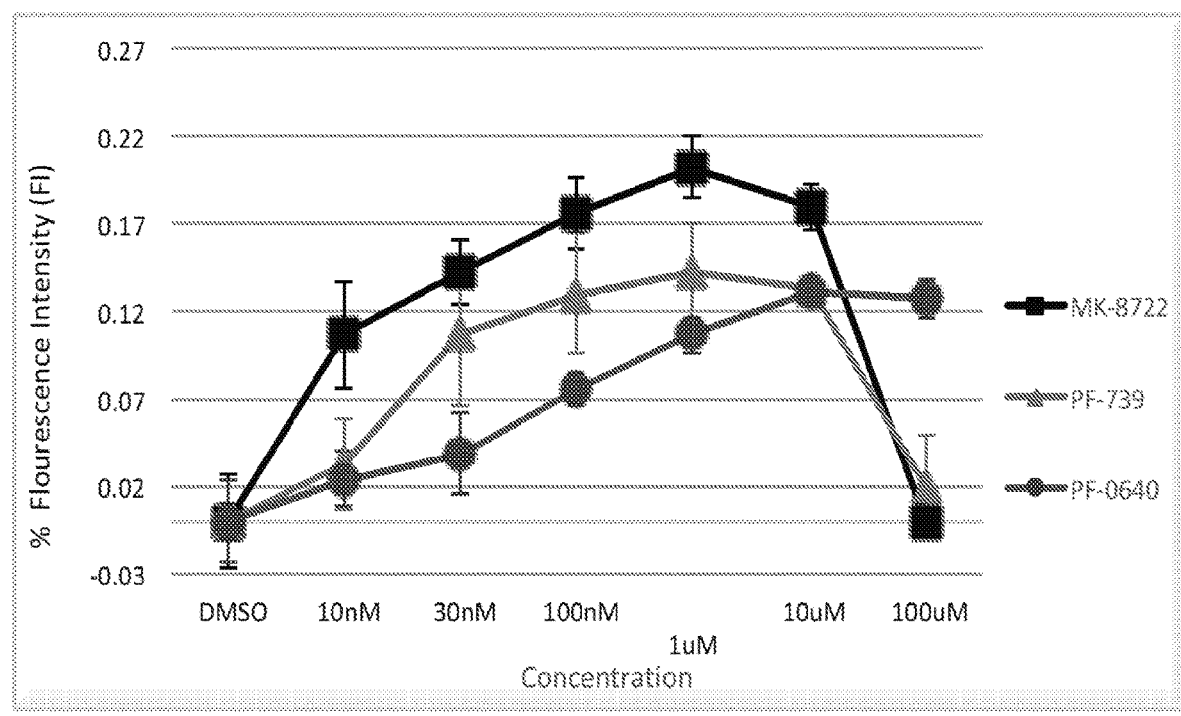

Various embodiments utilized direct AMPK agonists to increase cell viability and morphology in individuals having mitochondrial dysfunction. FIGS. 2A-2F illustrate the effect on cell viability of direct AMPK agonists of some embodiments. FIGS. 2A-2D illustrate cell viability in four fibroblast lines deficient for Cytochrome C Oxidase Assembly Factor (SURF1, FIG. 2A), Heme A:Farnesyltransferase Cytochrome C Oxidase Assembly Factor (COX10, FIG. 2B), Mitochondrial Complex I (CI, FIG. 2C), and Mitochondrial DNA Polymerase Gamma (POLG, FIG. 2D). In FIG. 2A, four direct AMPK agonists, PT1, A-769662, ZLN024, and C24 of various embodiments demonstrate a 35-55% increase in viability compared to untreated cells (e.g., cells treated with the vehicle, DMSO). FIGS. 2B-2D illustrate the effect on cell viability for mitochondrial dysfunctions encompassing components of the respiratory chain and mitochondrial DNA (mtDNA) replication machinery. Turning to FIGS. 2B-2D, the direct AMPK agonist, PT1, improves survival in these mutant lines despite the different pathogenic mechanisms of the gene deficiencies. Additionally, the remaining compounds showed variable responses among the mutant lines: A-769662 improved survival in CI and POLG-deficient cells, ZLN024 improved survival in CI-deficient cells, and C24 improved survival in SURF1-deficient cell but not in any of the other lines. Additionally, the indirect AMPK agonist, AICAR, does not improve cell viability in any of the other lines except SURF1 (FIG. 2A), indicating that AICAR is not as effective as direct AMPK agonists. The direct AMPK agonist, PT1, showed similar results in fibroblasts exhibiting NGLY-1 deficiency, as seen in FIG. 2E. FIG. 2E illustrates fibroblasts deficient in NGLY-1 isolated from three individuals. The fibroblasts treated with PT1 (+PT1) exhibit up to a 60% improvement in viability versus the untreated (−PT1) cells. Additionally, FIG. 2F shows the effect of cell viability of three newer AMPK agonists of various embodiments. In FIG. 2F, the AMPK agonists, MK-8722, PF-739, and PF-06409577 show increasing levels of cellular viability in SURF1 deficient fibroblasts in a dose dependent manner. Thus, direct AMPK agonists of various embodiments improve cell viability across a range of primary and secondary mitochondrial disease etiologies.

Figure 3K:
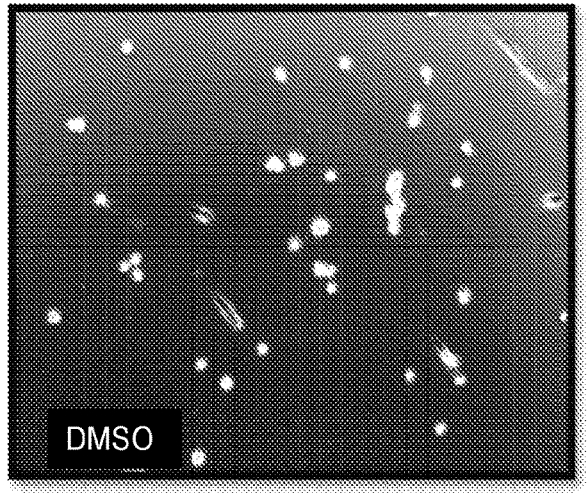
FIGS. 3A-3N illustrate cellular morphology of fibroblasts under various treatments in accordance with various embodiments.
Figure 3L:
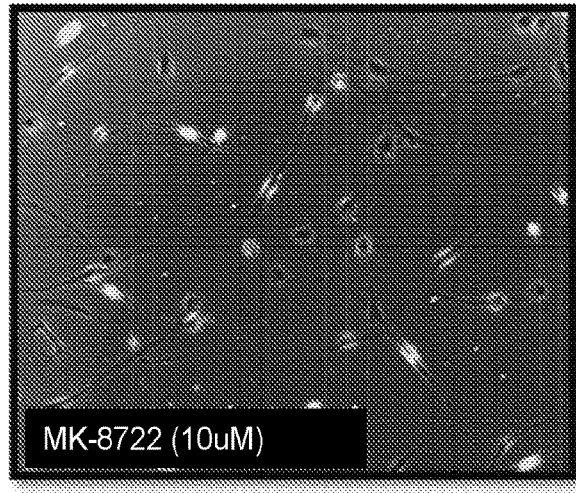
Figure 3M:
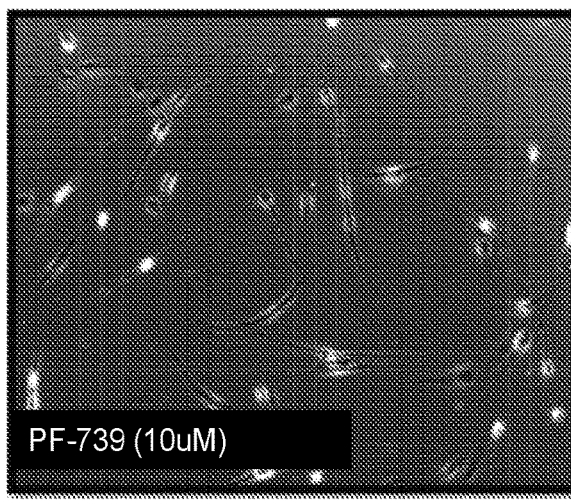
Figure 3N:
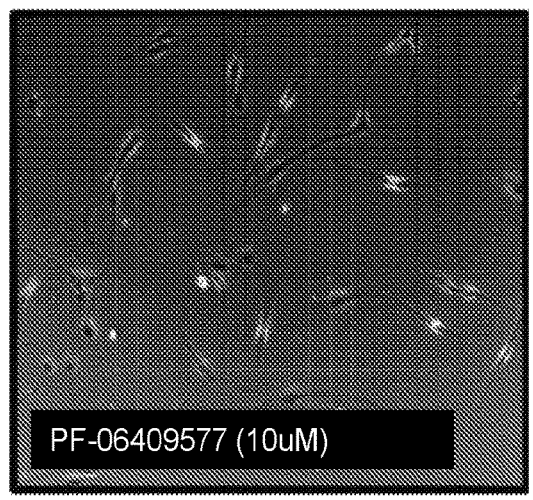

Turning to FIGS. 3A-3N, cellular morphology of fibroblasts with various deficiencies are illustrated, in accordance with many embodiments. Specifically, FIGS. 3A and 3B illustrate fibroblasts deficient in SURF1, where FIG. 3A illustrates cellular morphology without treatment (DMSO only), while FIG. 3B illustrates SURF1 deficient fibroblasts treated with PT1, showing improved cellular morphology over the untreated cells in FIG. 3A. Similarly, FIGS. 3C-3J illustrate similar results in cellular morphology, when treated with PT1, where FIGS. 3C and 3D illustrate fibroblasts deficient for COX10, FIGS. 3E and 3F illustrate fibroblasts deficient for CI, FIGS. 3G and 3H illustrate fibroblasts deficient for POLG, and FIGS. 3I and 3J illustrate fibroblasts deficient for NGLY-1. Similarly, FIGS. 3C, 3E, 3G, and 3I illustrate the untreated deficient fibroblasts, while FIGS. 3D, 3F, 3H, and 3J illustrate fibroblasts treated with PT1. Additionally, FIGS. 3K-3N illustrate the effect of newly developed AMPK agonists, MK-8722, PF-739, and PF-06409577, on SURF1-deficient fibroblasts. In particular, FIG. 3K shows SURF1-deficient fibroblasts treated only with the vehicle, DMSO, while FIG. 3L shows improved cellular morphology following treatment with MK-8722, FIG. 3M shows improved cellular morphology following treatment with PF-739, and FIG. 3N shows improved cellular morphology following treatment with PF-06409577. Thus, direct AMPK agonists of various embodiments improve cellular morphology across a range of primary and secondary mitochondrial disease etiologies.

Figure 4A:
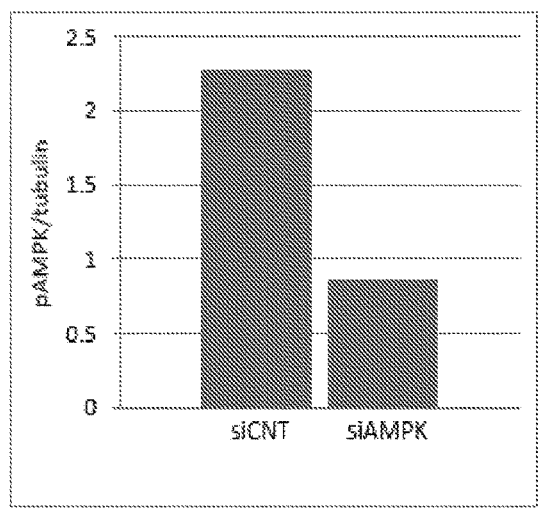
FIG. 4A illustrates pAMPK concentration in a knockdown assay in accordance with various embodiments.
Figure 4B:
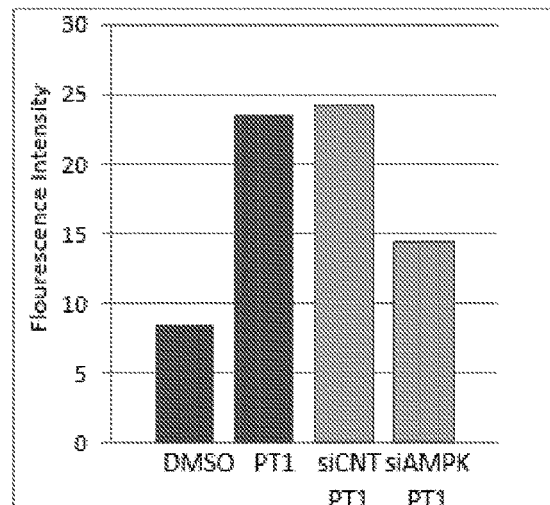
FIG. 4B illustrates cell viability results in a knockdown study with various treatments in accordance with various embodiments.
Figure 4C:
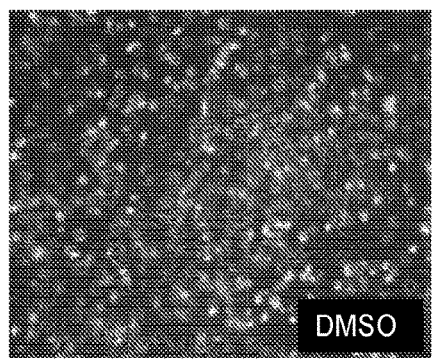
FIGS. 4C-4F illustrate cellular morphology results in a knockdown study with various treatments in accordance with various embodiments.
Figure 4D:
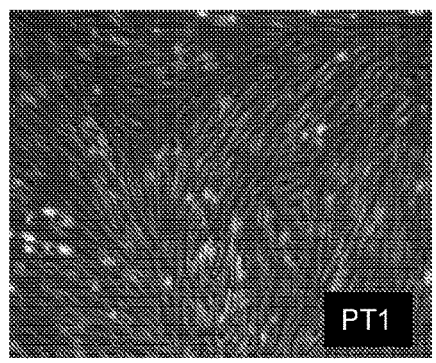
Figure 4E:
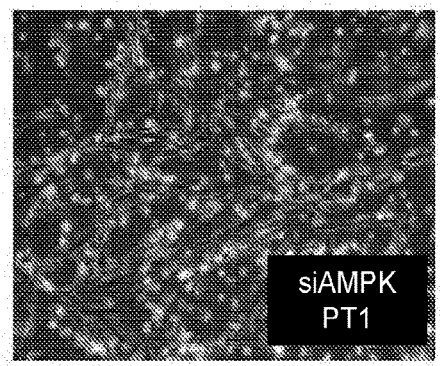
Figure 4F:
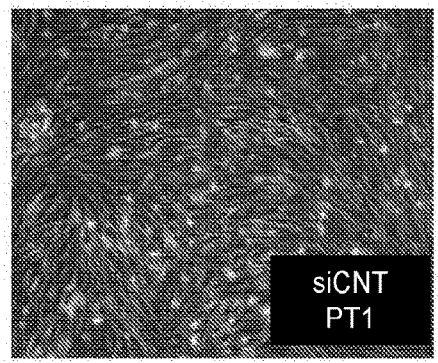

Turning now to FIGS. 4A-4F, direct AMPK agonists of certain embodiments are specific to AMPK activation and not nonspecific interactions. FIG. 4A illustrates a protein blot (western blot) of phosphorylated AMPK (pAMPK) demonstrating the relative level of pAMPK to tubulin after treatment after transfecting COX10 deficient fibroblasts with small interfering RNA (siRNA). A siRNA specific for the AMPK alpha subunit gene, PRKAA1, resulted in a decrease in pAMPK levels over cells transfected with a nonspecific siRNA used as a control (siCNT). FIG. 4B illustrates cell viability in the COX10 deficient fibroblasts with and without PT1 treatment and with and without siRNA transfection, showing that PT1 treatment alone (PT1) and PT1 treatment with the nonspecific siCNT (siCNT+PT1) have increased viability over untreated cells (DMSO) and cells treated with PT1 and transfected with siAMPK (siAMPK+PT1). Additionally, treatment with PT1 together with selective knockdown of AMPK (siAMPK+PT1) results in a 63% decrease in pAMPK levels and 41% decrease in cell viability compared to control conditions (siCNT+PT1), consistent with the idea that cellular response to PT1 is mediated by AMPK activation. FIGS. 4C-4F illustrate cellular morphology under the same conditions as present in FIG. 4B. Specifically, FIG. 4C illustrates untreated COX10 deficient fibroblasts; FIG. 4D illustrates COX10 deficient fibroblasts treated with PT1; FIG. 4E illustrates COX10 deficient fibroblasts transfected with siAMPK and treated with PT1; and FIG. 4F illustrates COX10 deficient fibroblasts transfected with the control siCNT and treated with PT1.

Figure 5A:
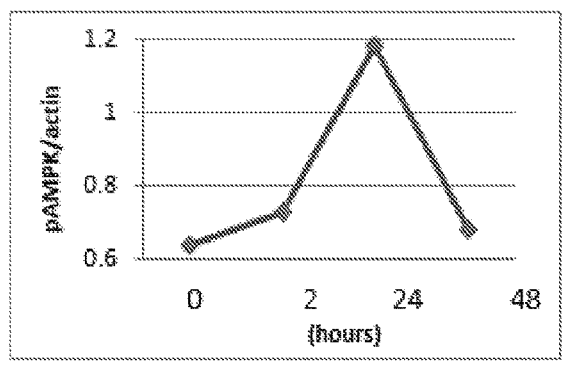
FIG. 5A illustrates pAMPK concentration after a treatment assay in accordance with various embodiments.
Figure 5B:
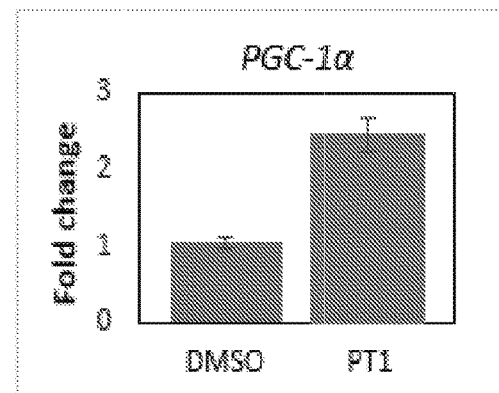
FIG. 5B-5D illustrate gene expression levels after a treatment assay in accordance with various embodiments.
Figure 5C:
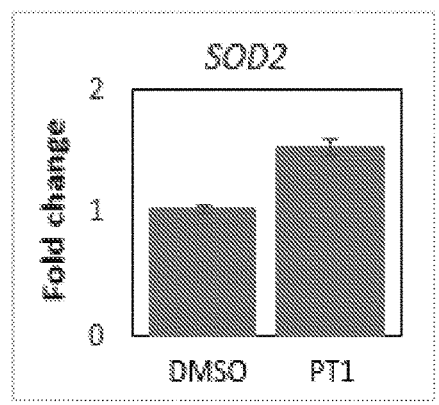
Figure 5D:
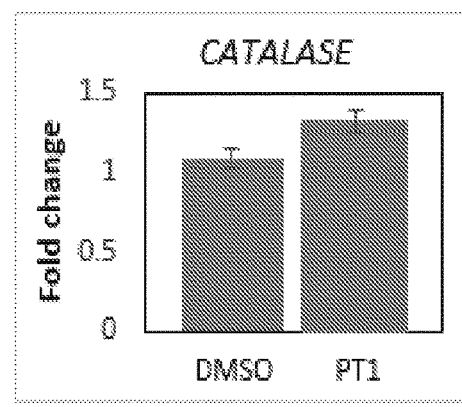

Turning to FIGS. 5A-5D, certain embodiments of direct AMPK agonists address metabolic disruptions caused by mitochondrial dysfunction. FIG. 5A illustrates pAMPK levels normalized to actin in SURF1 deficient fibroblasts treated with PT1 for 0 hours, 2 hours, 24 hours, and 48 hours. FIG. 5A illustrates that pAMPK levels increase within 2 hours post PT1 treatment and peaked at 24 hours post PT1 treatment. Additionally, pAMPK levels return to baseline positions after 48 hours post PT1 treatment. In FIGS. 5B-5D, the effect of PT1 treatment, in accordance with various embodiments, increase gene expression of mitochondrial biosynthesis and antioxidant genes. FIG. 5B shows a 2.4-fold increase in expression of peroxisome proliferator-activated receptor gamma coactivator 1-alpha (PGC-1α), while FIGS. 5C and 5D illustrate a 1.3-fold increase in manganese superoxide dismutase (SOD2) expression and a 1.5-fold increase in catalase expression, respectively.

Effect of Direct AMPK Agonists on Cellular Respiration

Figures 6A, 6B, 6C:
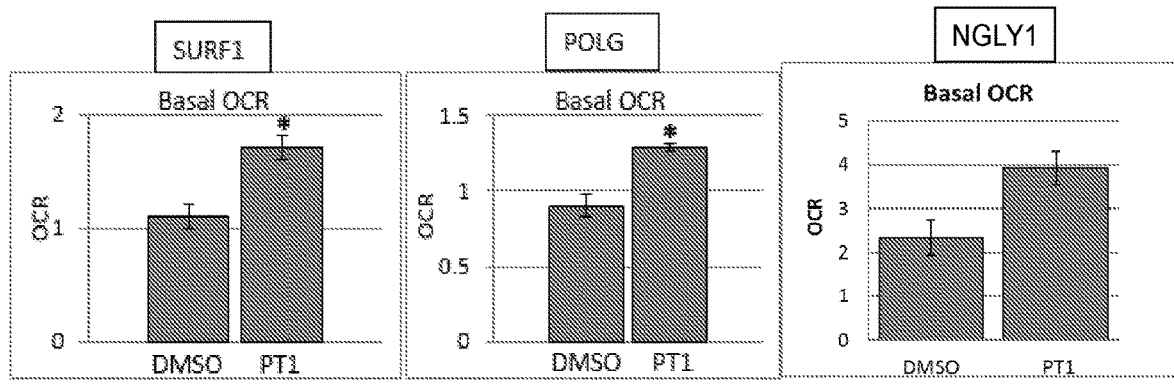
FIGS. 6A-6H illustrate cellular respiration results with and without treatment on various deficient fibroblast lines in accordance with various embodiments.
Figures 6D, 6E:
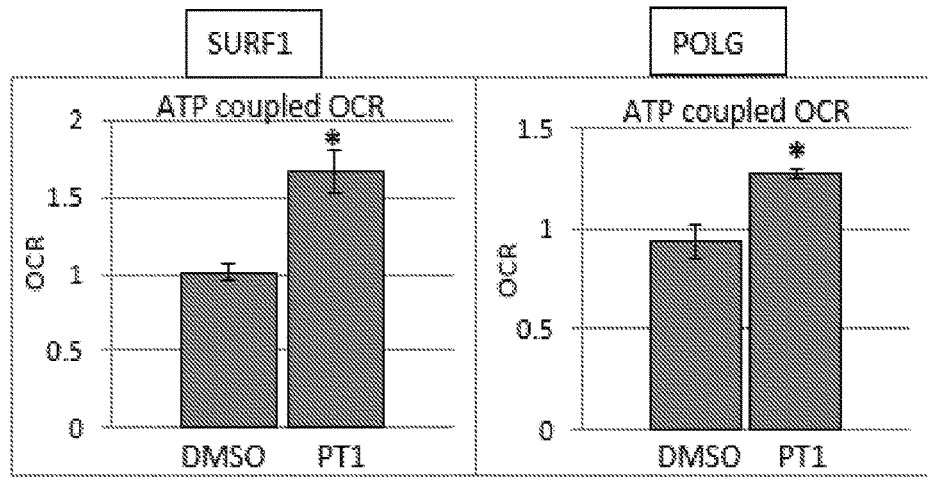
Figures 6F, 6G, 6H:
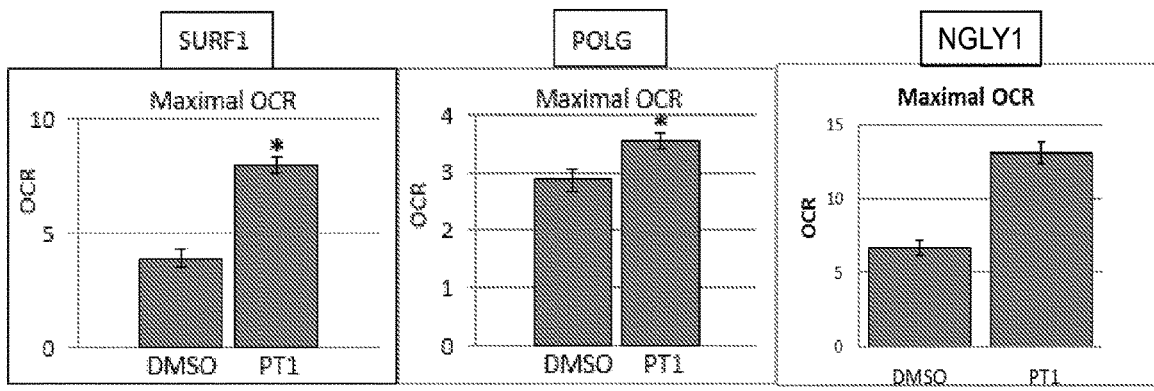

Various embodiments improve cellular respiration in individuals with mitochondrial dysfunction. As noted above, certain embodiments increase PGC-1α expression. PGC-1a stimulates the biogenesis of new mitochondria that possess increased respiratory function as compared to aged mitochondria having accrued secondary mtDNA mutations and reactive oxygen species (ROS). Turning to FIGS. 6A-H, improved respiratory function caused by direct AMPK agonists of some embodiments is illustrated. FIGS. 6A-6C show basal oxygen consumption rates (OCR) in SURF1, POLG, and NGLY1 deficient fibroblasts, respectively. Despite etiological differences in each gene, SURF1, POLG, and NGLY1 deficient fibroblasts showed an approximately 30% improvement for SURF1 and POLG deficient fibroblasts and 16% improvement in NGLY1 deficient fibroblasts in basal respiration when treated with PT1 over untreated (DMSO), in accordance with various embodiments. Additionally, FIGS. 6D and 6E illustrate the fraction of basal mitochondrial oxygen consumption used for ATP synthesis (ATP-coupled respiration) in SURF1 (FIG. 6D) and POLG (FIG. 6E) deficient fibroblasts. In this situation, the treatment with PT1 shows an improvement of approximately 40% in SURF1 deficient fibroblasts (FIG. 6D) and 30% in POLG deficient fibroblasts (FIG. 6E) over the untreated (DMSO) fibroblasts, in line with certain embodiments. Further, treatment with PT1 in accordance with some embodiments improves maximal respiration capacity, which reflects the ability to of cells to respond to increased ATP demand, as illustrated in FIGS. 6F-6H. In FIGS. 6F, SURF1 deficient fibroblasts show an approximately 50% improvement in maximal respiration in cells treated with the direct AMPK agonist, PT1 over the untreated (DMSO) fibroblasts. Similarly, FIG. 6G illustrates that POLG deficient fibroblasts show an improvement of approximately 20% in maximal respiration in cells treated with the direct AMPK agonist, PT1 over the untreated (DMSO) fibroblasts. And, FIG. 6H shows an approximately 40% improvement in maximal respiration NGLY1 deficient fibroblasts when treated with the direct AMPK agonist, PT1 over the untreated (DMSO) fibroblasts.

Effect of Direct AMPK Agonists on Oxidative Stress and Energy Status

Figure 7A:
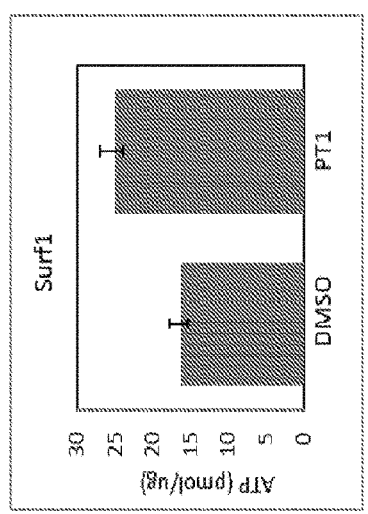
FIGS. 7A-7C illustrate ATP concentrations with and without treatment of various deficient fibroblast lines in accordance with various embodiments.
Figure 7B:
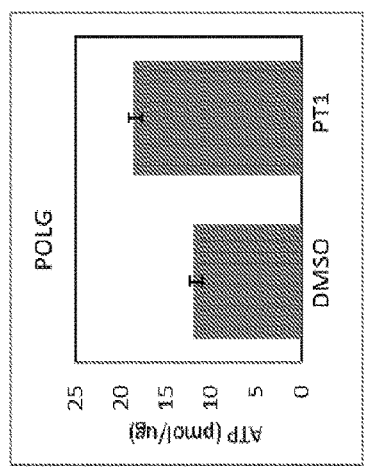
Figure 7C:
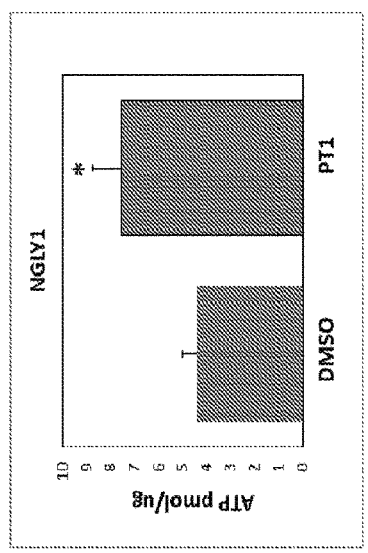
Figure 7D:
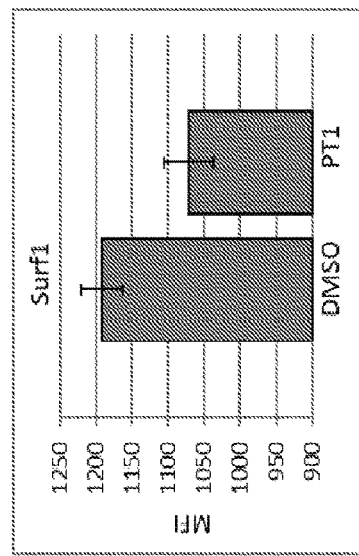
FIGS. 7D-7F illustrate reactive oxygen species (ROS) concentrations with and without treatment of various deficient fibroblast lines in accordance with various embodiments.
Figure 7E:
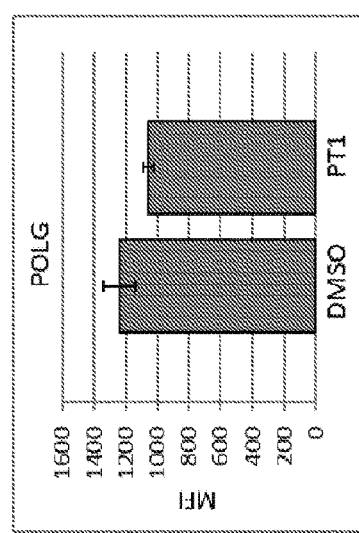
Figure 7F:
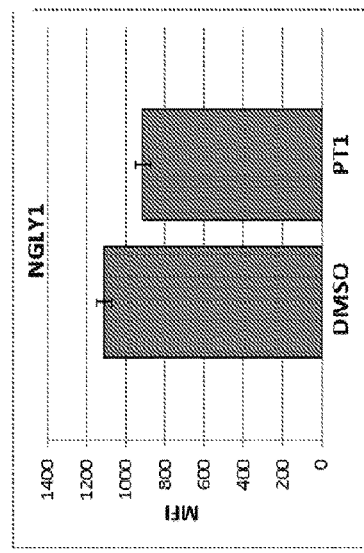

Turning now to FIGS. 7A-7F, various embodiments improve ATP production and reduce reactive oxygen species (ROS) levels in mitochondrial dysfunction. Specifically, FIGS. 7A, 7B, and 7C show increases in ATP production of 35% in SURF1 deficient fibroblasts, 36% in POLG deficient fibroblasts, and 40% inNGLY1 deficient fibroblasts treated with the direct AMPK agonist, PT1, over untreated (DMSO) fibroblasts, respectively. Further, FIGS. 7D, 7E, and 7F illustrate reductions in ROS levels of 10% in SURF1 deficient fibroblasts, 15% in POLG deficient fibroblasts, and 18% in NGLY1 deficient fibroblasts treated with the direct AMPK agonist, PT1, over untreated (DMSO) fibroblasts, respectively. Mitochondrial dysfunction causes an incomplete electron transfer through the respiration chain (RC), leading to decreased ATP synthesis and over-production of reactive oxygen species (ROS). (See, e.g., Atkuri et al, Proc Natl Acad Sci USA. 2009 Mar. 10; 106(10):3941-5; Enns et al, PLoS One. 2014 Jun. 18; 9(6); the disclosures of which are incorporated herein by reference in their entirety.) ATP and ROS content reflect cellular energy and oxidative status, both of which are dependent on effective ATP-coupled respiration and overall mitochondrial function. Cellular responses to these metabolic disruptions involve activating pathways that improve cellular respiration (e.g., mitochondrial biogenesis) and upregulating the expression of endogenous antioxidants to neutralize ROS and decrease oxidative stress. Thus, improvements in ATP production and reduction in ROS levels, as shown in FIGS. 7A-7F, show the ability of various embodiments to improve the oxidative stress and energy status of mitochondrial dysfunction.

Effect of Direct AMPK Agonists on Lipofuscin Levels

Figure 8A:
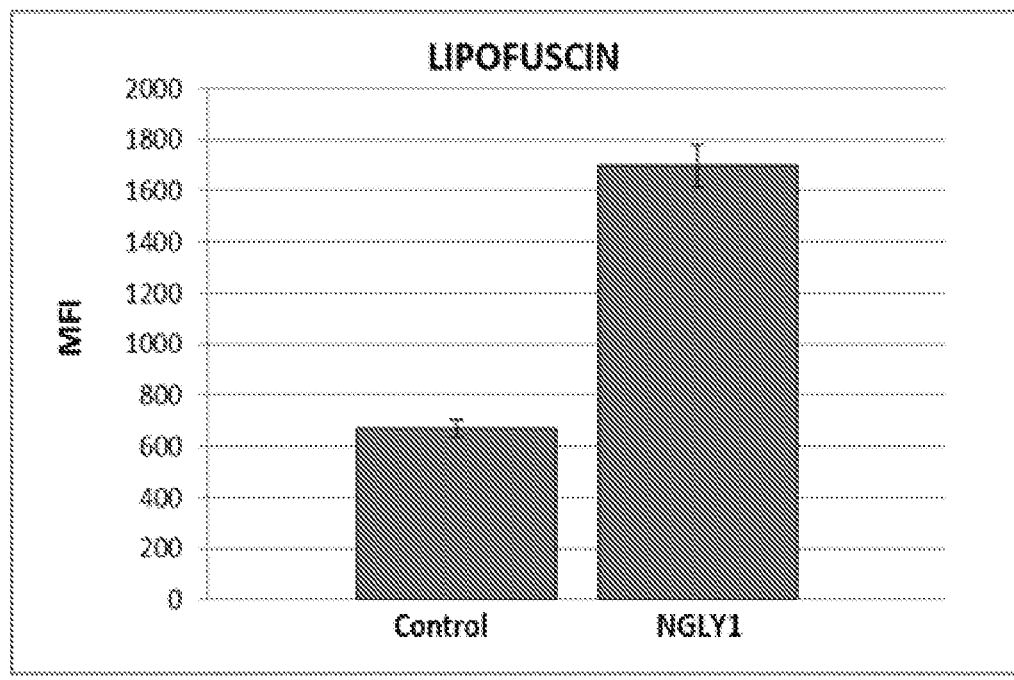
FIG. 8A illustrates lipofuscin levels in control and NGLY1 deficient fibroblast lines in accordance with various embodiments.
Figure 8B:
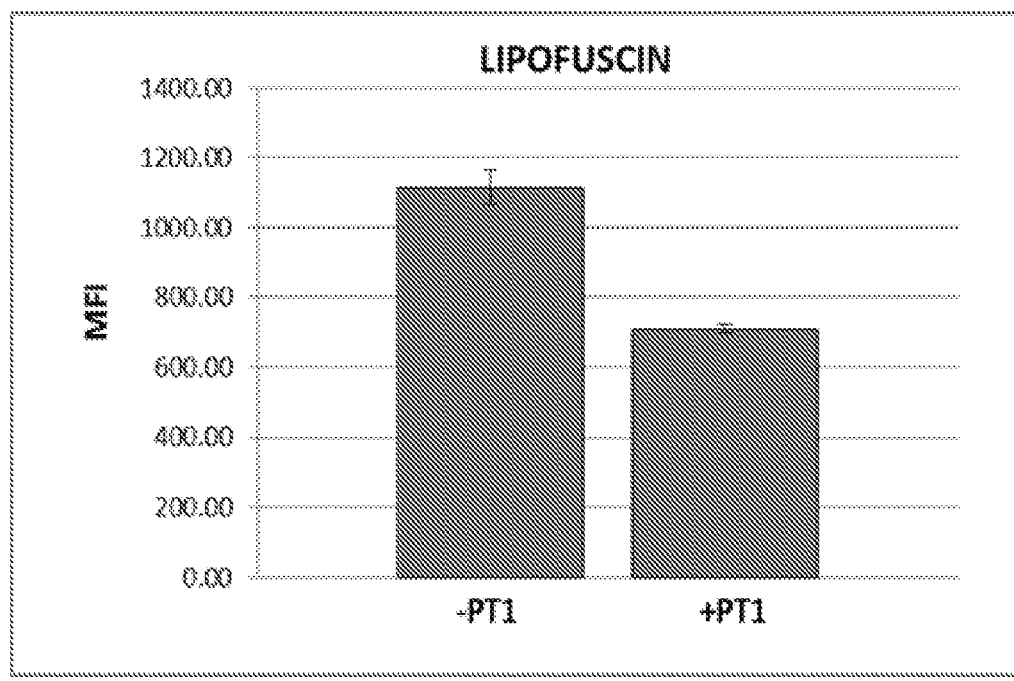
FIG. 8B illustrates lipofuscin levels in an NGLY1 deficient fibroblast line and with and without treatment in accordance with various embodiments.

Some embodiments decrease accumulation of aberrant glycoproteins as seen in FIGS. 8A-8B. Certain mitochondrial dysfunctions, including those caused by NGLY1 deficiencies, produce an accumulation of proteins and lipids, called lipofuscin. (See, e.g., Jobst, et al., J Clin Pathol. 1991 May; 44(5): 437-438; the disclosure of which is incorporated herein by reference in its entirety.) As seen in FIG. 8A, NGLY1 deficient fibroblasts exhibit approximately 60% higher levels of lipofuscin than normal fibroblasts (Control). FIG. 8B illustrates that treatment with the direct AMPK agonist, PT1, in accordance with various embodiments, reduces lipofuscin levels by approximately 36% in NGLY1 deficient fibroblasts.

AMPK Activation Attenuates Retinal Degeneration in AMD

Figure 9A:
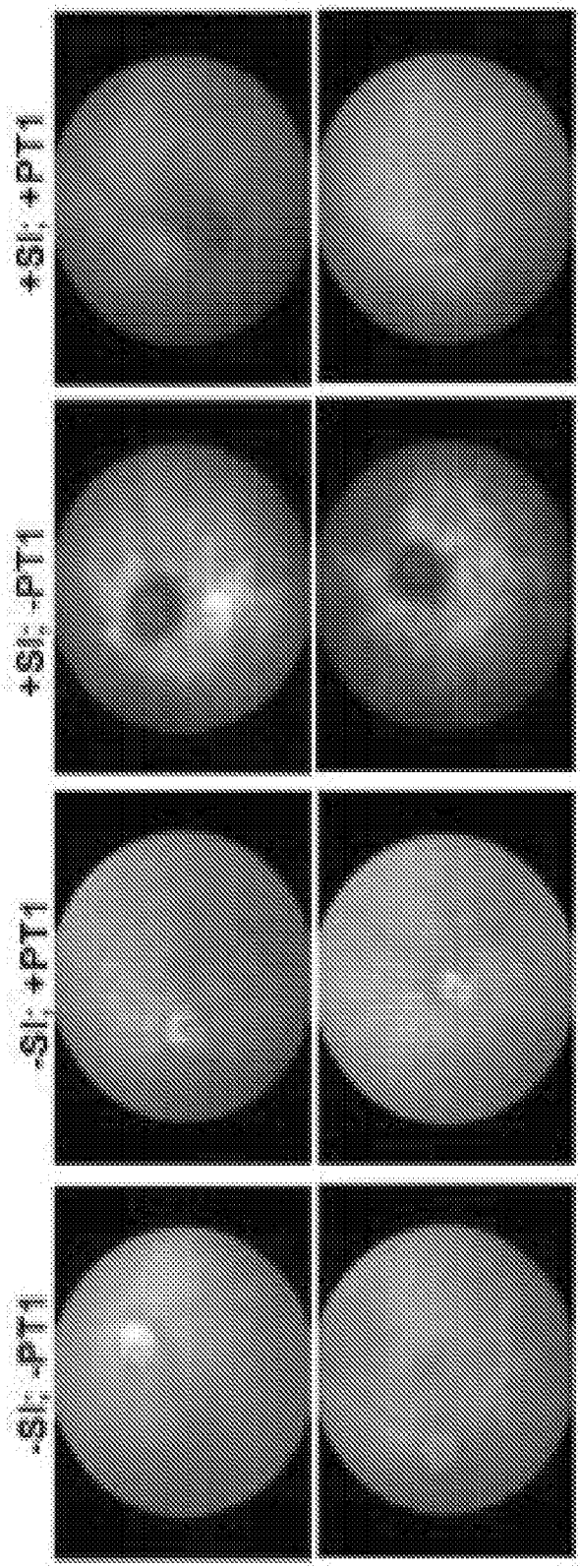
FIG. 9A illustrates funduscopy images of retinas with and without treatment in a control and an induced AMD model in accordance with various embodiments.
Figure 9B:
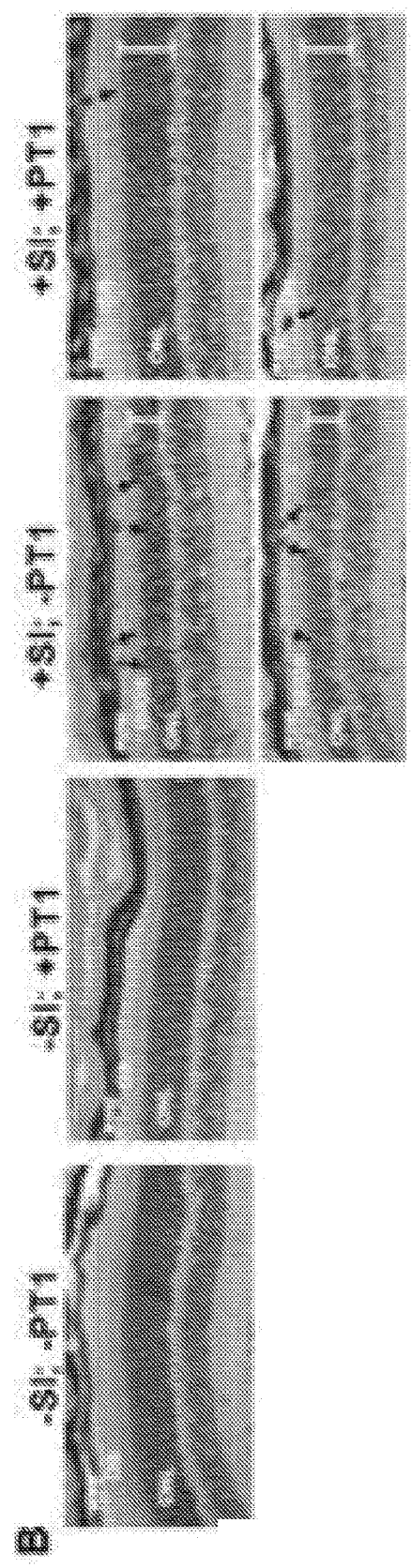
FIG. 9B illustrates retinal section images of retinas with and without treatment in a control and an induced AMD model in accordance with various embodiments.
Figure 9C:
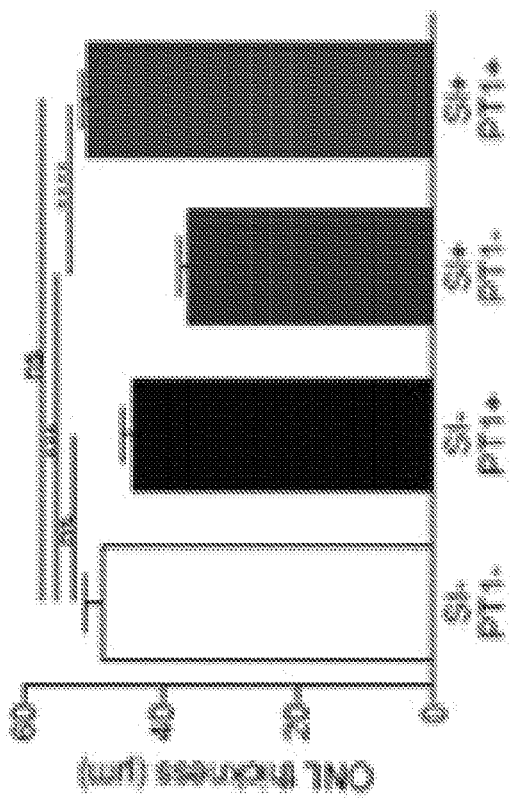
FIG. 9C illustrates ONL thickness measurements of retinas with and without treatment in a control and an induced AMD model in accordance with various embodiments.

Turning now to FIGS. 9A-9E, various embodiments attenuate retinal damage caused by mitochondrial dysfunction. In particular, FIG. 9A shows funduscopic images of retinas treated with and without sodium iodate (SI) and with and without the direct AMPK agonist, PT1, in accordance with certain embodiments. SI is a toxin that selectively induces oxidative stress and mitochondrial dysfunction in retinal pigment epithelium (RPE). As such, SI treated tissue simulates retinal disorders caused by mitochondrial dysfunction, such as AMD. As seen in FIG. 9A, the tissue without SI treatment (−SI) with and without PT1 (+PT1 and −PT1) have similar, normal tissue. However, tissue treated with SI and without PT1 (+SI; −PT1) shows signs of retinal degeneration, including white deposits. However, tissue treated with both SI and PT1 (+SI; +PT1) show improved signs of retinal degeneration. Thus, indicating that direct AMPK agonists of various embodiments attenuate retinal degeneration. Similarly, FIG. 9B shows similar results from H&E staining of retinal sections. As illustrated, tissue without SI treatment (−SI; −PT1 and −SI, +PT1) have similar appearances. However, the −SI; +−PT1 tissue shows signs of retinal degeneration, including thinning of the photoreceptor outer nuclear level (ONL), disorganization of the inner and photoreceptor outer/inner segments (IS/OS), and presence of melanin debris. With treatment of PT1 in the SI treated tissue, these disease indications are reduced, including a protection against ONL thinning (white bars), alterations in photoreceptor morphology, and decreased melanin debris (black arrows). Measurements of ONL thickness are illustrated in FIG. 9C, where the tissue not treated with SI (SI−, PT1− and SI−, PT1+) and the SI and PT1 treated tissue (SI+, PT1+) show greater thickness than the SI treated tissue without PT1 treatment (SI+, PT1−). Further, FIG. 9D demonstrates improved electrical response of retinal tissue treated with both SI and PT1 (PT1+; SI+) to levels similar to normal tissue (PT1−; SI− and PT1+; SI−) over the tissue treated with SI and without PT1 (PT1−; SI+).

Figure 9D:
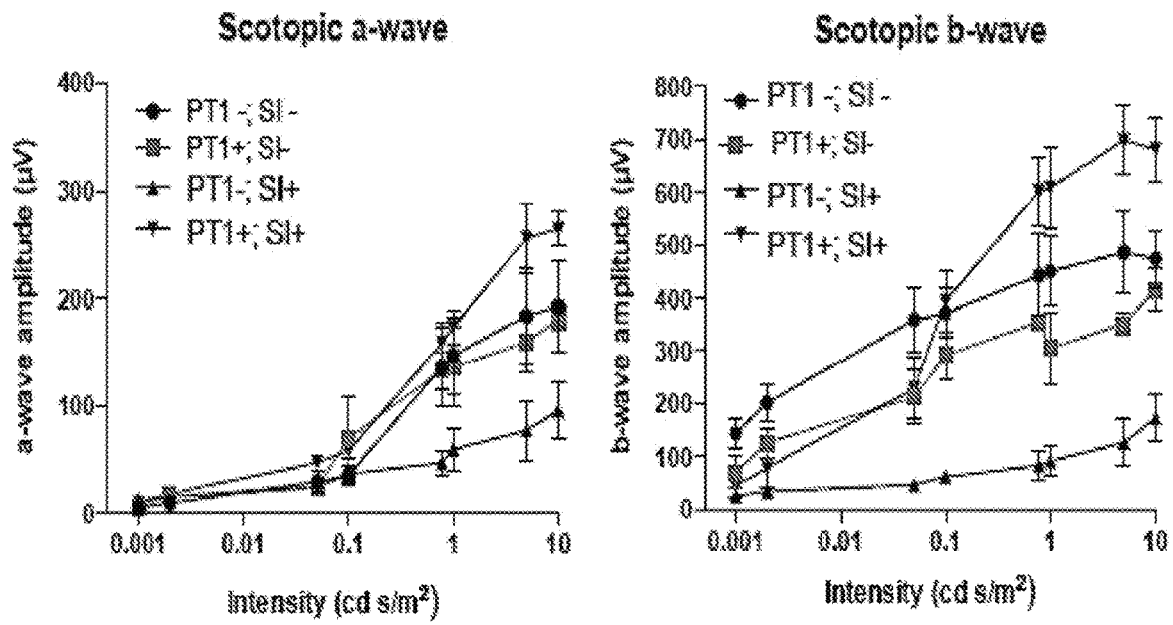
FIG. 9D illustrates electroretinography images of retinas with and without treatment in a control and an induced AMD model in accordance with various embodiments.
Figure 9E:
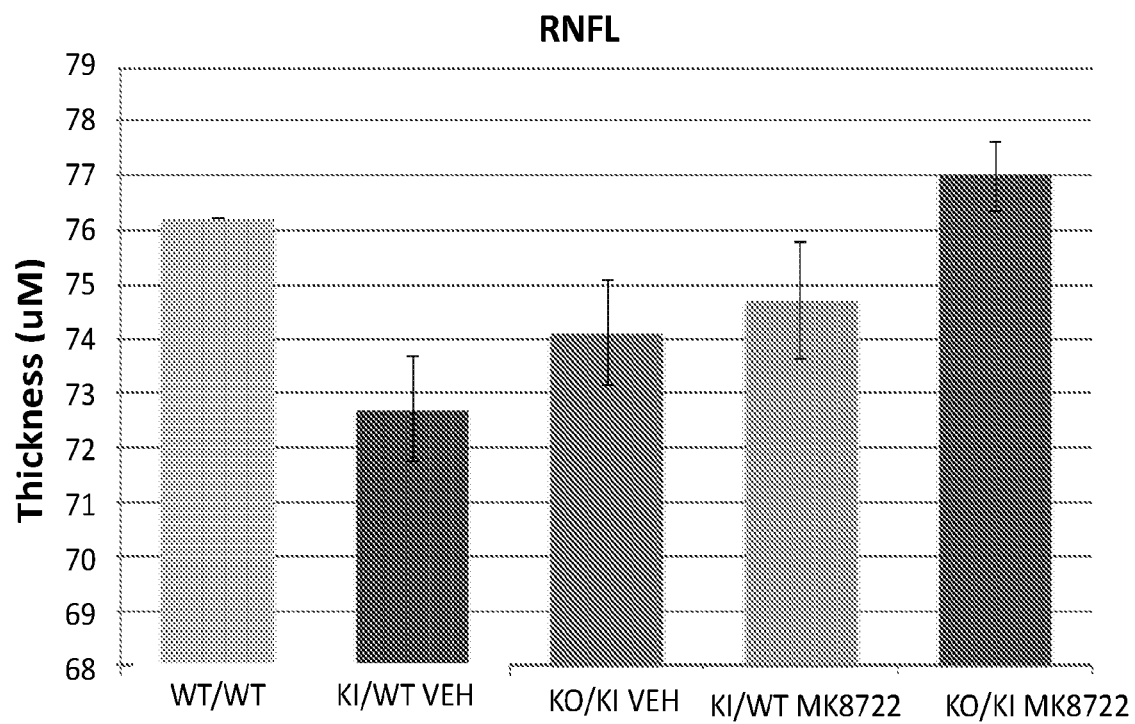
FIG. 9E illustrates reduced retinal degradation after treatment with AMPK agonists in accordance with various embodiments.

Further, FIG. 9E illustrates retinal thickness in wild type mice (WT/WT) as mice that are possess knock-out and/or knock-in alleles of the cytochrome C oxidase assembly protein, SCO2, where the knock-in allele represented an E129K mutation on the SCO2 protein. In particular, the mice are heterozygous knock-in and wild type (KI/WT) or heterozygous knock-out and knock-in (KO/KI). FIG. 9E illustrates how treated (MK8722) mice demonstrate less degradation than mice treated with only a vehicle (VEH) mice.

Mitochondrial dysfunction in the eye of patients with mitochondrial disease result in ophthalmic manifestations such as retinopathy and optic atrophy, and compromised mitochondrial function has also been shown to be associated with the age-related macular degeneration (AMD). Given that the eye is one of the most energy-dependent tissues in the body, both primary and secondary mitochondrial diseases with ophthalmological findings are expected to benefit from AMPK activation. (See, e.g., Calaza, et al, Neurobiol Aging. 2015 October; 36(10):2869-76; the disclosure of which is incorporated by reference herein in its entirety.) Thus, the direct AMPK agonists of various embodiments will be used to treat patients with ophthalmic diseases associated with mitochondrial dysfunction.

Neuroprotection in Ischemic Stroke

Figure 10C:
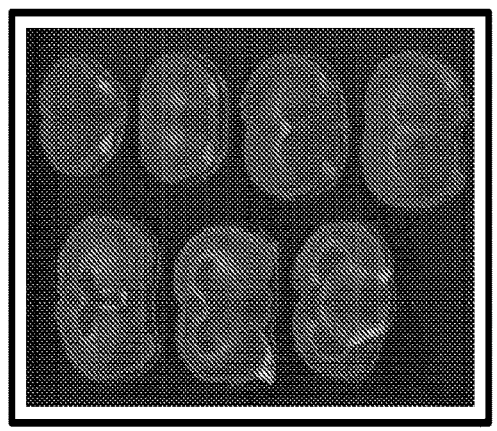
FIGS. 10B and 10C illustrate brain slices with infarct tissue in treated and untreated ischemic tissue in accordance with various embodiments.
Figure 10B:
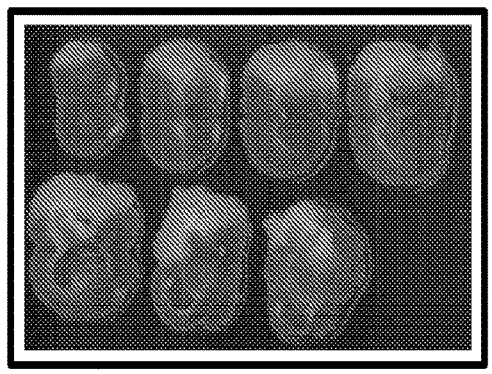
Figure 10A:
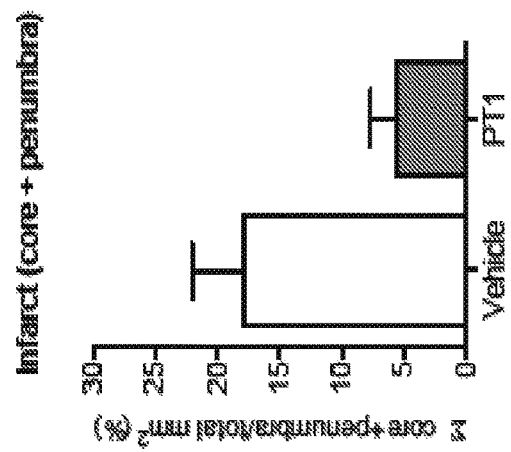
FIG. 10A illustrates percent of infarct tissue in treated and untreated ischemic tissue in accordance with various embodiments.

Some embodiments provide neuroprotection in individuals with ischemic stroke. Impairment of mitochondrial energy metabolism in neurons is the key pathogenic factor in ischemic stroke and a number of neurodegenerative disorders, including certain primary mitochondrial diseases, AD, PD, and ALS (Schon et al, J Clin Invest. 2003 Feb. 1; 111(3): 303-312; the disclosure of which is incorporated herein by reference in its entirety). FIGS. 10A-10C demonstrate the neuroprotective effect of direct AMPK on individuals suffering ischemic stroke. In particular, FIG. 10A shows the percent of infarct tissue in brain tissue suffering ischemic stroke. As seen in FIG. 10A, treatment with PT1 shows a marked improvement over individuals treated with only the vehicle DMSO (Vehicle). Turning to FIGS. 10B and 10C, illustrate TCC-stained brain slices, where individuals treated with only the vehicle (FIG. 10B) show high levels of ischemic tissue in white, whereas the individuals treated with PT1 (FIG. 10C), in accordance with various embodiments, show much lower amounts of ischemic tissue in white.

Effect of AMPK Agonists on Motor Performance and Skeletal Muscle

Figure 11A:
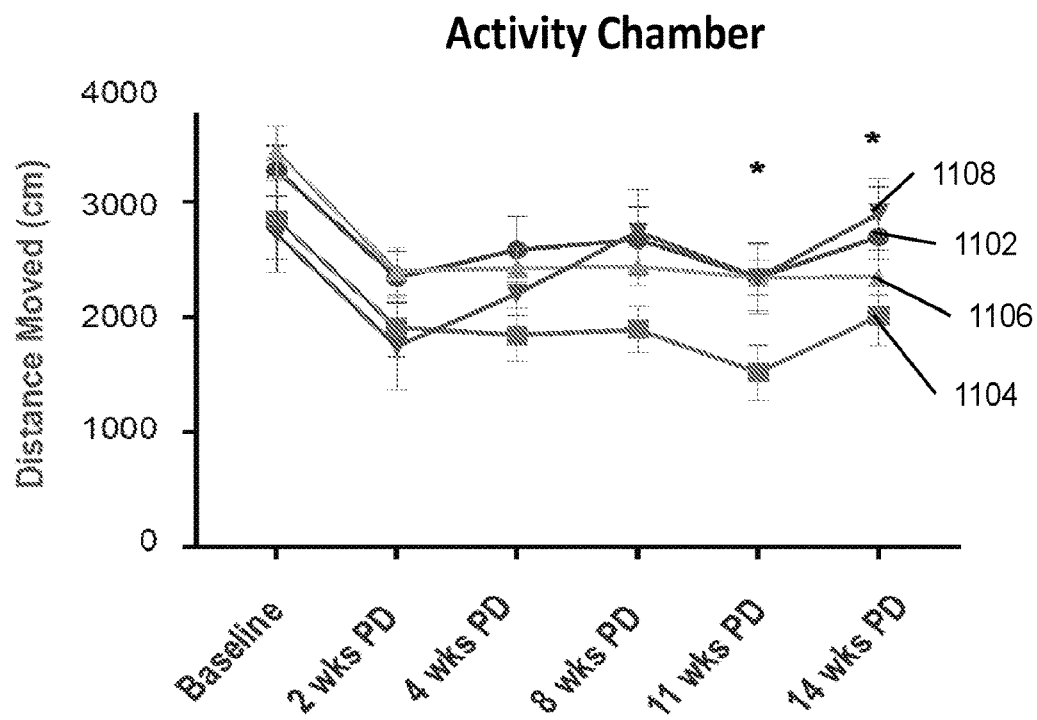
FIGS. 11A-11C illustrate locomotor performance in treated and untreated mice in accordance with various embodiments.
Figure 11B:
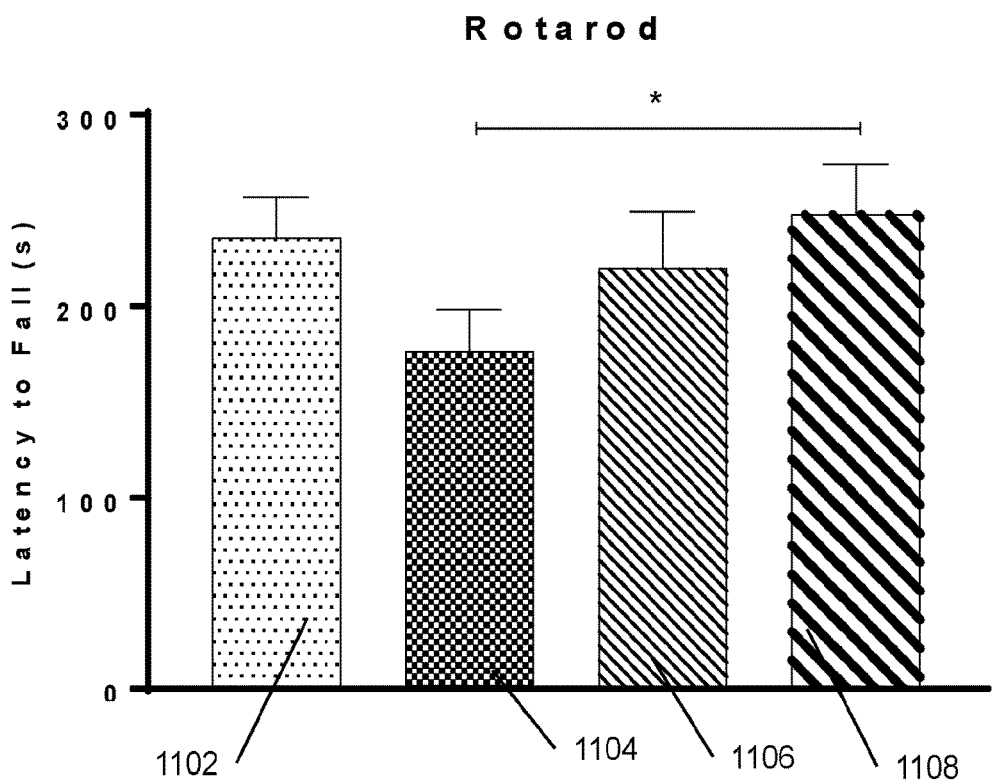
Figure 11C:
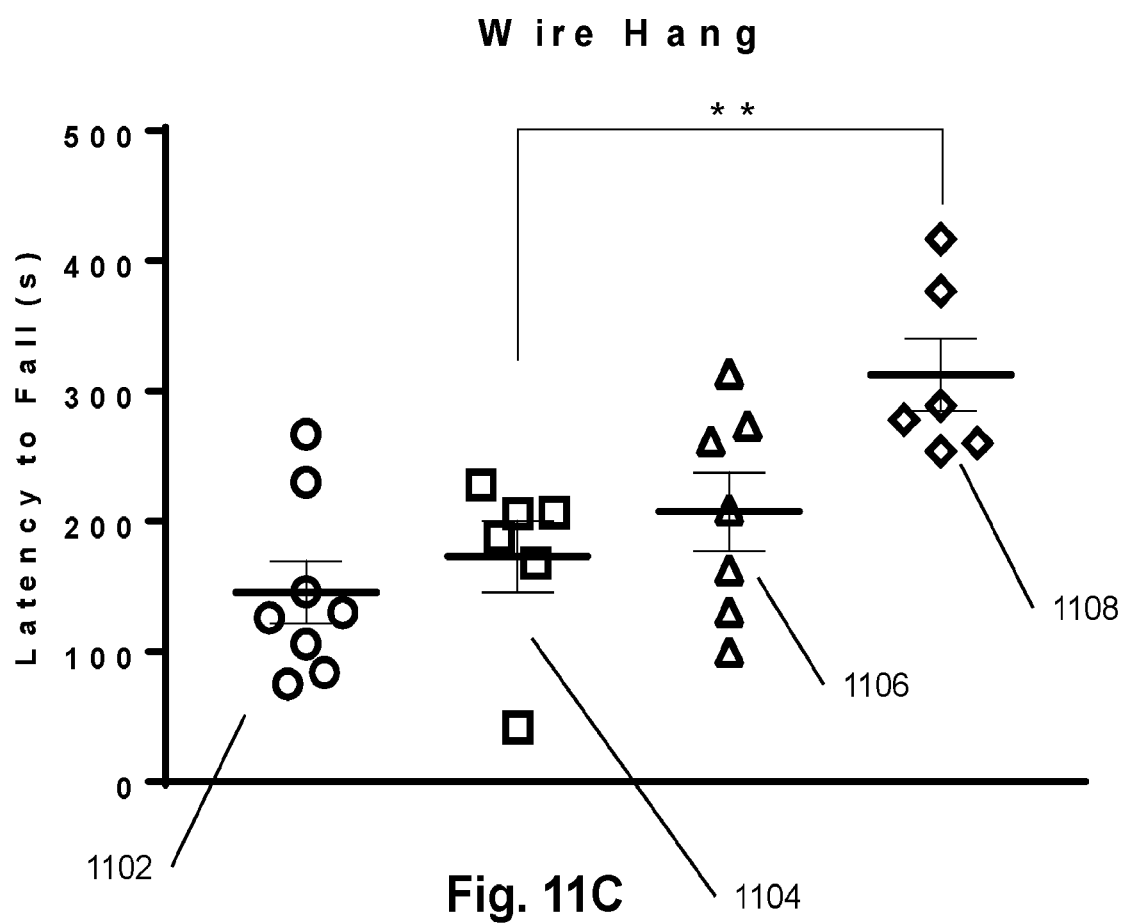

Various embodiments will be used to improve motor performance in individuals with mitochondrial dysfunction as well as muscle wasting diseases, such as muscular dystrophies and autoimmune myositis disorders. FIGS. 11A-11C illustrate improvements in muscle performance using the AMPK agonists MK-8722, in accordance with various embodiments. FIG. 11A illustrates distance travelled in an activity chamber by mice with various genotypes in the SCO2 gene treated with an AMPK agonist and with a delivery vehicle only. Specifically, FIG. 11A illustrates heterozygous knock-in and wild-type mice treated with only a vehicle (1102), heterozygous knock-in and knock-out mice treated with only a vehicle (1104), heterozygous knock-in and wild-type mice treated with an AMPK agonist (1106), and heterozygous knock-in and knock-out mice treated with an AMPK agonist (1108). As illustrated in FIG. 11A, heterozygous knock-in and wild-type mice show similar levels of activity, regardless of whether they are treated with an AMPK agonist (1106) or vehicle-only (1102), while mice that are heterozygous for knock-out and knock-in alleles show reduced activity when treated with a vehicle only (1104), but activity in the knock-out/knock-in mice treated with an AMPK agonist (1108) returns to levels comparable with knock-in/wild-type mice.

FIG. 11B illustrates rotarod performance improvements in knock-out/knock-in mice using an AMPK agonist (1108) over knock-out/knock-in mice with vehicle-only treatment (1104). Additionally, the knock-out/knock-in mice using an AMPK agonist (1108) show levels higher than the knock-in/wild-type mice treated with an AMPK agonist (1106) or vehicle treated (1102). Similarly, FIG. 11C illustrates results from a hanging wire assay illustrating that AMPK agonists of many embodiments improve muscle performance. In particular, AMPK agonists are capable of improving wire hang time in knock-out/knock-in mice (1108) to levels higher than the knock-in/wild-type (1102, 1106) as well as the vehicle-treated knock-out/knock-in (1104). Collectively, FIGS. 11A-11C illustrate that AMPK activation from AMPK agonists of many embodiments can enhance strength, endurance, and overall locomotor function in muscle-degenerative disorders associated with mitochondrial dysfunction.

Figure 11D:
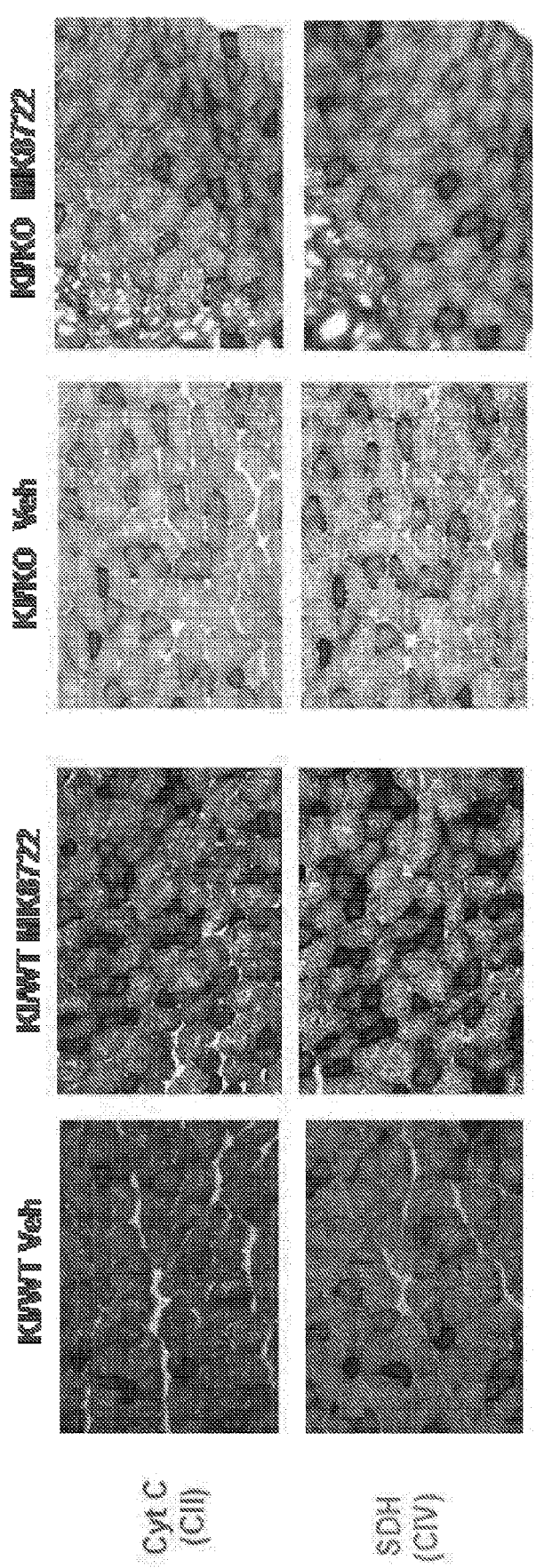
FIGS. 11D and 11E illustrate mitochondrial function and glycogen storage in treated and untreated mice in accordance with various embodiments.
Figure 11E:
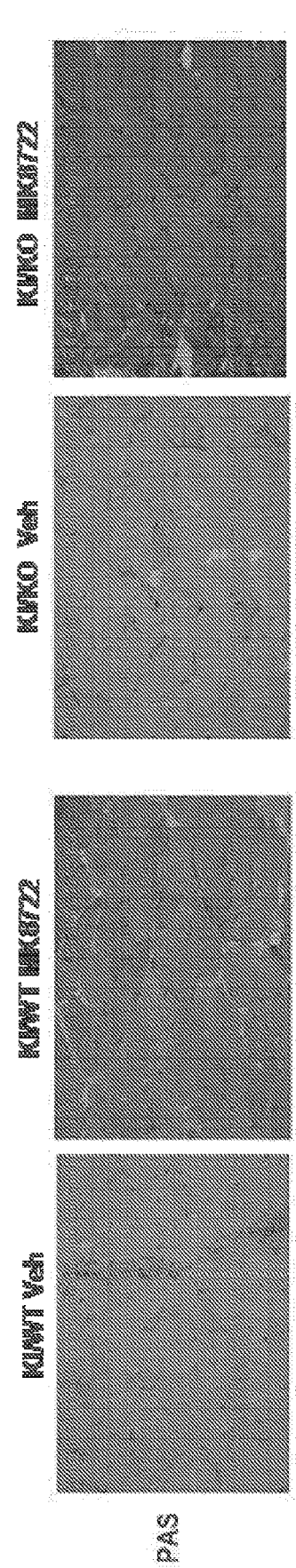

Many embodiments are further capable of increasing mitochondrial function and/or glycogen storage in skeletal muscle, as indicated in FIGS. 11D-11E. FIG. 11D illustrates that histological staining indicative of mitochondrial cytochrome C oxidase (CtyoC) and succinate dehydrogenase (SDH) activities. The darker staining in embodiments treating with an AMPK agonist indicates increased activity over the lighter stained vehicle-only treated samples. Similarly, the darker staining of glycogen in FIG. 11E illustrates an increased presence of stored glycogen in samples treated with an embodiment of an AMPK agonist. The combination of increased mitochondrial function and glycogen content indicates that embodiments are capable of normalizing energy levels within skeletal muscle, thereby preventing degeneration and weakness.

Figure 11F:
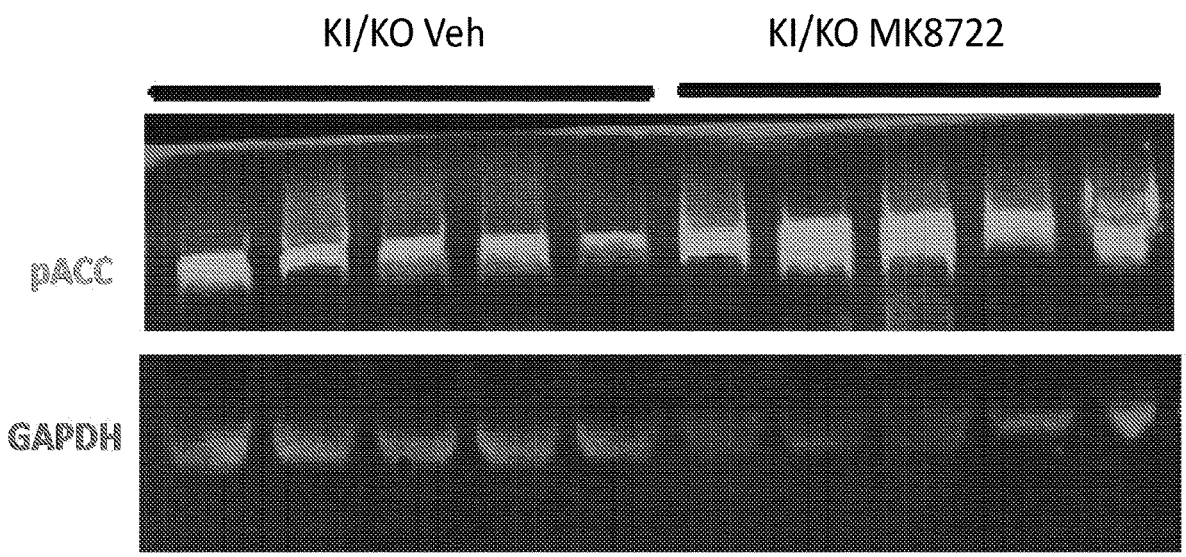
FIGS. 11F and 11G illustrate results of ACC phosphorylation assays performed on treated and untreated mice in accordance with various embodiments.
Figure 11G:
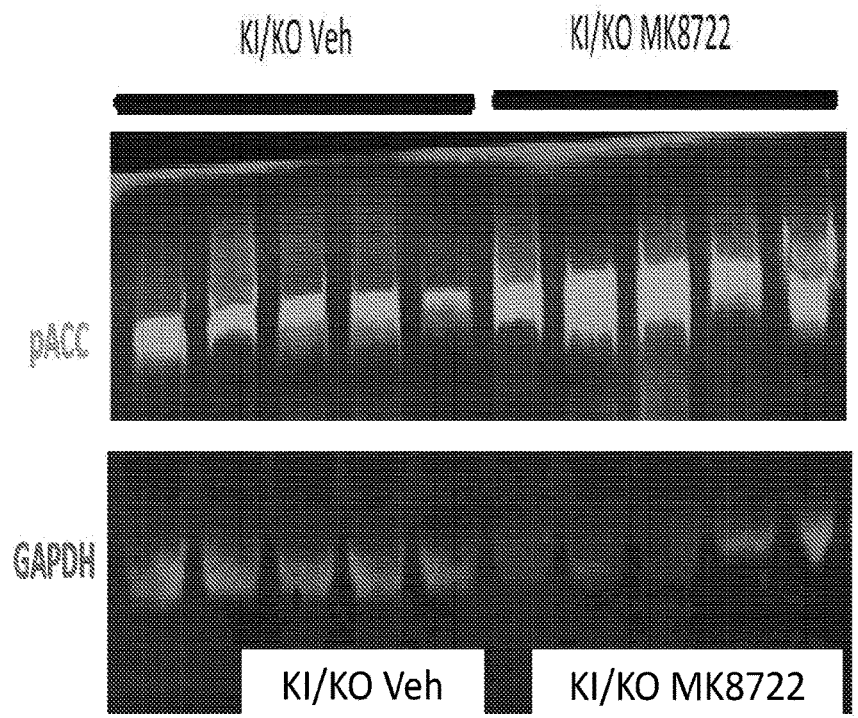

Turning to FIGS. 11F-11G, the increased phosphorylation of ACC in skeletal muscle. In particular, FIG. 11F illustrates a western blot of phosphorylated ACC (pACC) in mice treated with a vehicle only (KI/KO Veh) as well as in mice treated an AMPK agonist of many embodiments (KI/KO MK8722). FIG. 11G summarizes the western blots by normalizing pACC to 1 in mice treated with a vehicle only (KI/KO Veh) and mice treated an AMPK agonist of many embodiments (KI/KO MK8722). FIGS. 11F-11G thus indicate that AMPK agonists of many embodiments are capable of activating AMPK in skeletal muscle.

Embodiments of AMPK Agonists

Figure 12A:
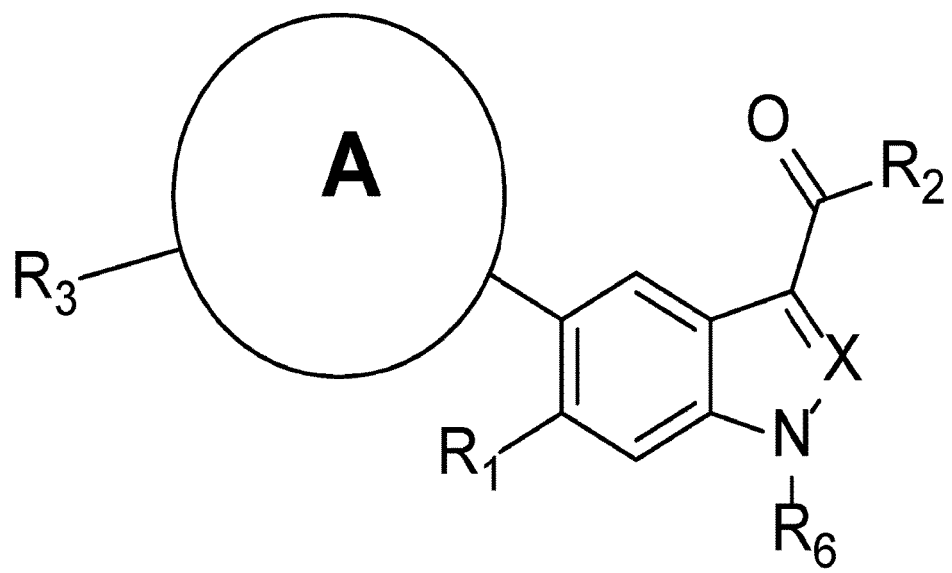
FIG. 12A illustrates a generalized structure of AMPK agonists in accordance with various embodiments.

Many embodiments are directed to highly potent, selective and stable small molecule agonists of AMPK. Many such embodiments are directed to molecules having a generalized structure as illustrated in FIG. 12A. A number of embodiments will modify the generalized structure in FIG. 12A to generate derivative molecules based on the structure in FIG. 12A. Derived molecules can be tested for activity in a number of ways known in the art or described herein, such as measuring pACC in a sample, as in indicator of increasing AMPK activity. By varying certain fragments, R-groups, etc., it is possible to develop a systematic understanding of how each fragment influences AMPK activity.

Derivative molecules of certain embodiments are developed from the structure in 12A. In many embodiments, moieties, R-groups, or other fragments may be substituted by one or more of the following:

A is selected from 5-membered ring heterocyclics either unsubstituted or substituted with one or more $C_{1-6}$ alkyl or fluoro substituents;

X is $CR_5$ or N;

$R_1$ is H, $CF_3$ or halo;

$R_2$ is $OR_5$, NHOH, $NHSO_2R_4$, $OCH_2OCOR_4$ or $COR_2$ is a C-linked tetrazole, $R_3$ is $C_{1-10}$ alkyl, $C_{3-7}$ cycloalkyl, $C_{4-12}$ alkylcycloalkyl, $C_{4-10}$ cycloalkylalkyl, $C_{3-7}$ heterocycloalkyl, $C_{4-12}$ alkylheterocycloalkyl, $C_{4-10}$ heterocycloalkylalkyl, aryl or heteroaryl either unsubstituted or substituted with one to three substituents selected from halo, OH and $OCOR_7$;

$R_4$ is $C_{1-10}$ alkyl, $C_{3-7}$ cycloalkyl, $C_{4-12}$ alkylcycloalkyl, $C_{4-10}$ cycloalkylalkyl either unsubstituted or substituted with one to three halogen substituents;

$R_5$ is $R_4$ or H;

$R_6$ is H, $C_{1-6}$ alkyl, $C_{3-6}$ cycloalkyl, or two $R_6$ groups, together with the nitrogen atom to which they are attached can form a four to seven membered heterocycloalkyl ring, all of which can be optionally substituted with 1 to 3 fluorine atoms, $R_7$ is $C_{1-10}$ alkyl, $C_{3-7}$ cycloalkyl, $C_{4-12}$ alkylcycloalkyl unsubstituted or substituted with one to three substituents selected from fluoro, $C_{1-10}$ alkyl and $NR_6$, $R_6$.

In many embodiments, A is selected from the group consisting of:

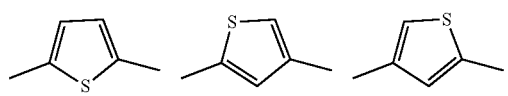

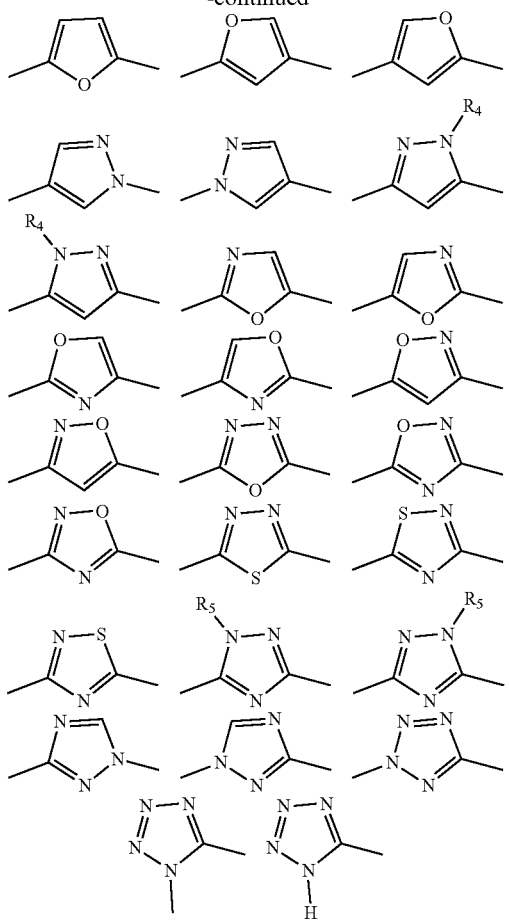

Figure 12B:
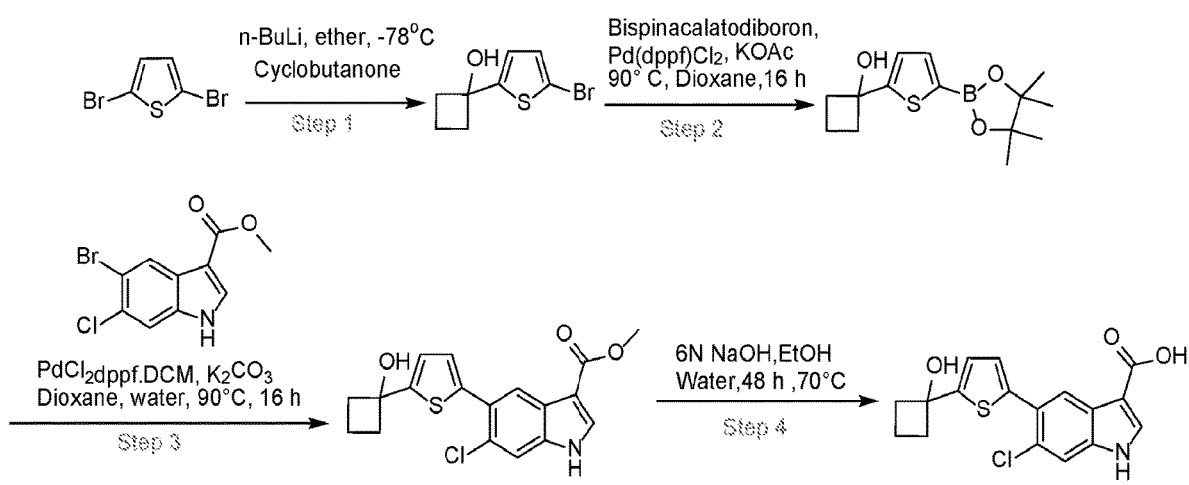
FIG. 12B-12D illustrate schematics methods of synthesis of AMPK agonists in accordance with various embodiments.
Figure 12C:
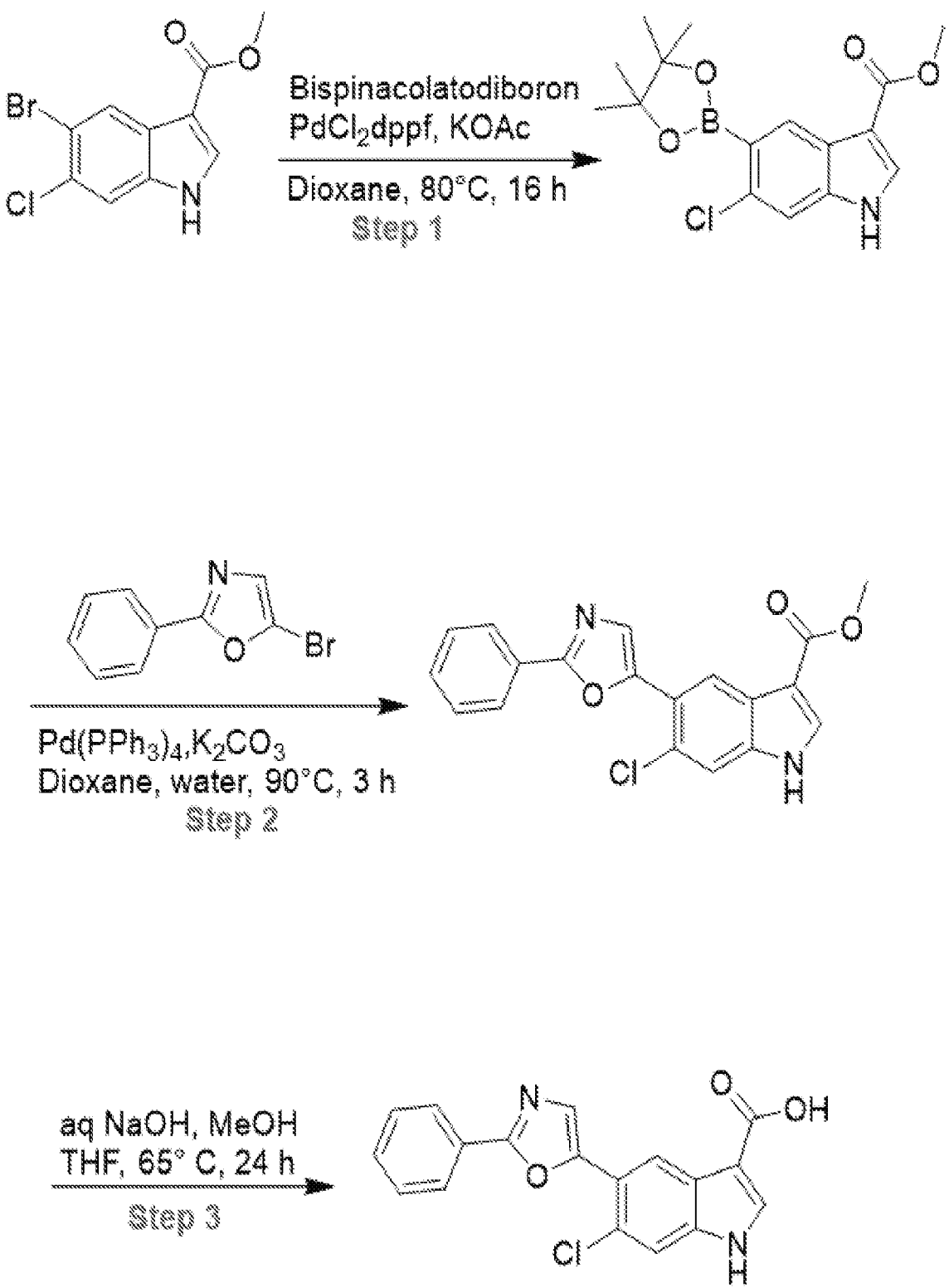
Figure 12D:
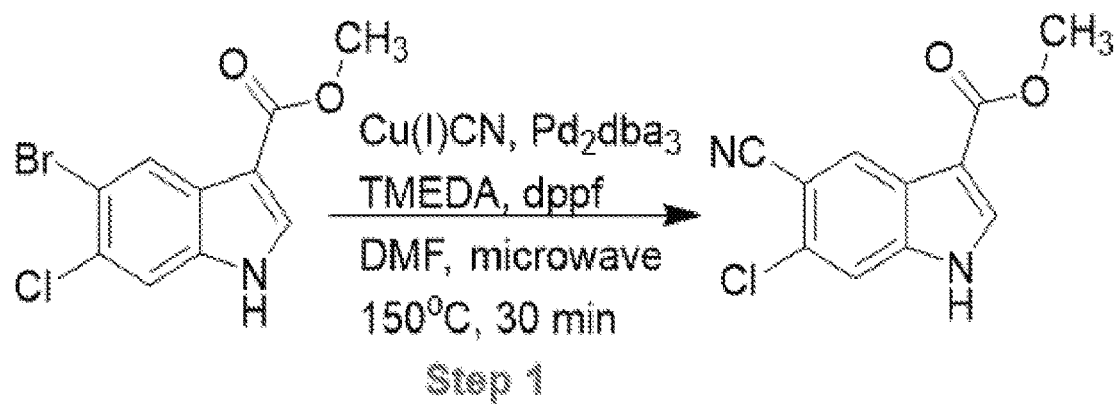
Figure 12D:
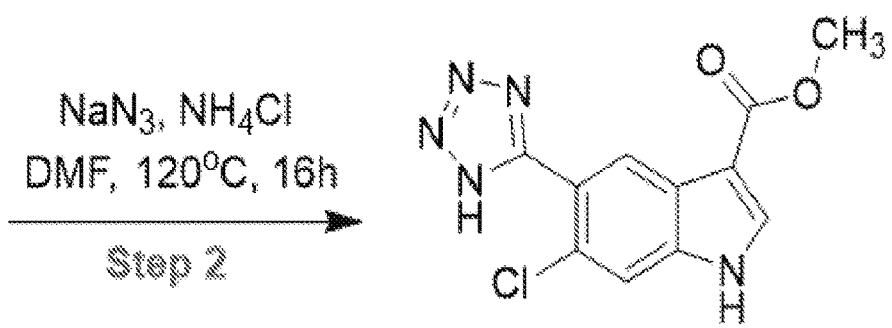
Figure 12D:
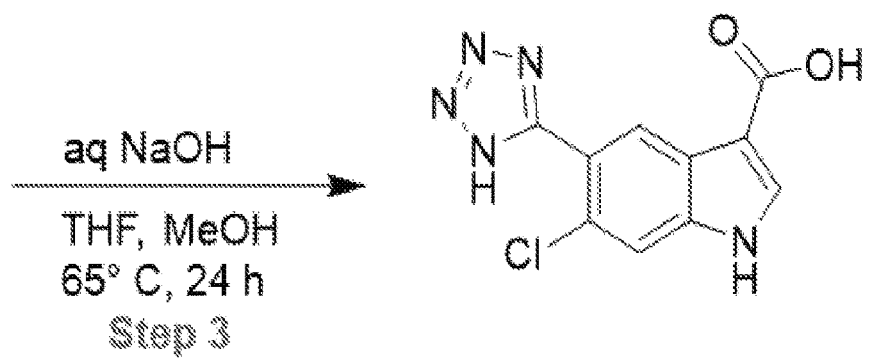

A number of embodiments can be manufactured or synthesized, such as by using a method as illustrated in FIGS. 12B-12D. FIG. 12B illustrates a method to synthesize the compound illustrated in FIG. 13A. In particular, FIG. 12B illustrates a step 1 of combining cyclobutanone with 2,5-dibromothiophene to generate 1-(5-bromothiophen-2-yl)cyclobutan-1-ol. At Step 2, Bispinacalatodiboron is added to the result of Step 1 to generate 1-(5-(4,4,5,5-tetramethyl-1,3,2-dioxaborolan-2-yl)thiophen-2-yl)cyclobutan-1-ol. Step 3 combines this product with methyl 5-bromo-6-chloro-1H-indole-3-carboxylate and $K_2CO_3$ to generate methyl 6-chloro-5-(5-(1-hydroxycyclobutyl)thiophen-2-yl)-1H-indole-3-carboxylate. Finally, Step 4 generates 6-chloro-5-(5-(1-hydroxycyclobutyl)thiophen-2-yl)-1H-indole-3-carboxylic acid (FIG. 13A), by combining the product of step 3 with NaOH and ethanol. While the process of FIG. 12B generates the compound illustrated in FIG. 13A, it should be noted that additional compounds can be generated in a similar manner (e.g., the processes illustrated in FIGS. 12C-12D), such as the compounds illustrated in FIGS. 13B-13Z and 14A-14O.

Additional embodiments will be prepared by the method shown in FIG. 12C, such that the boron group is attached first to the indole ring of these embodiments, then coupled to the A Ring (as shown in FIG. 12A).

Further embodiments will be prepared by the method of FIG. 12D, where the A Ring contains four nitrogen atoms.

Figure 15A:
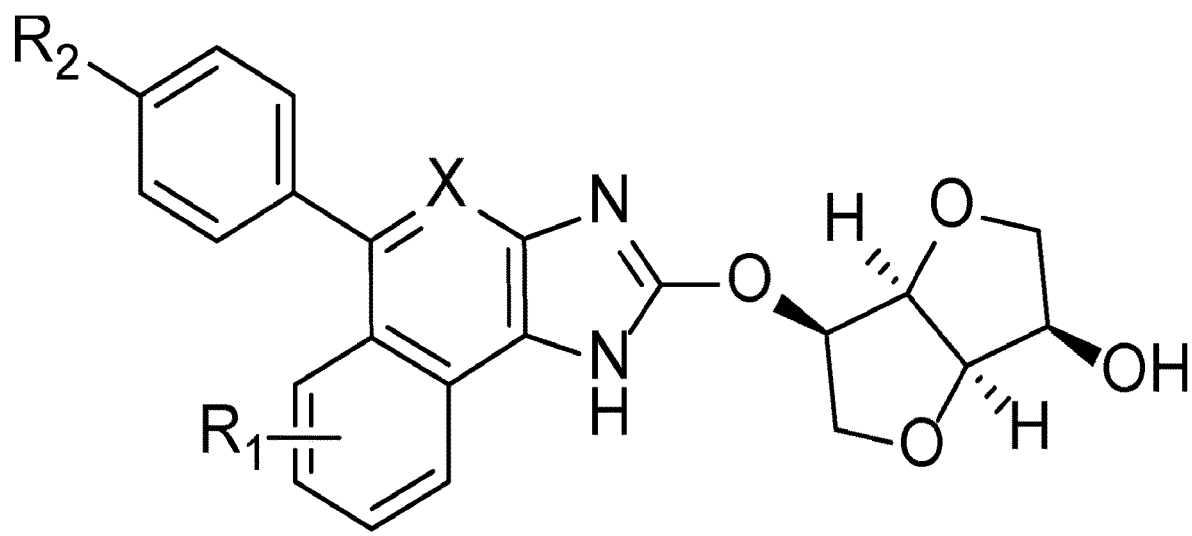
FIGS. 15A-15B illustrate generalized structures of AMPK agonists in accordance with various embodiments.
Figure 15B:
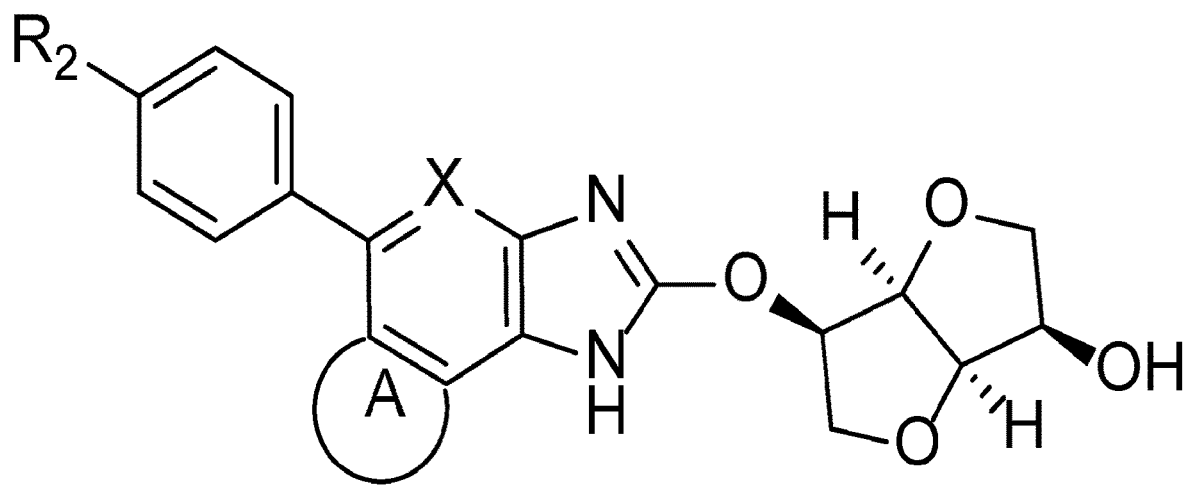

Further embodiments can possess different structures while still maintaining the ability to activate AMPK. Some embodiments will possess a generalized structure, such as illustrated in FIGS. 15A-15B.

Derivative molecules of certain embodiments are developed from the structure in 15A. In many embodiments, moieties, R-groups, or other fragments may be substituted by one or more of the following:

X is CH or N;
R$_1$ is small alkyl (C1-C4) or halogen (e.g., Cl, Br, or F);
R$_2$ is phenyl, alkyl C1-C10, cycloalkyl (C3-C10), hydroxyalkyl (C1-C6), heteroaromatic (e.g., pyridyl, pyrazolyl, pyrolyl, pyrimidyl, thiophenyl, furanyl, or triazole), or heterocyclic C4-C6;
   where phenyl is optionally substituted with halogens (e.g., Cl, Br, or F),
   where an alkyl is linear or branched and optionally substituted with OH, OMe, OEt,
   where cycloalkyl is optionally substituted with one or more OH,
   where hydroxy alkyl is linear or branched
   where heteroaromatic is optionally substituted with small alkyls (C1-C6) or hydroxyalkyls (C1-C6), where alkyls and hydroxyalkyls are linear or branched,
   where heteroatom in hetrocyclic is optionally O, S, or NR$_4$, where R$_4$ is a linear or branched C1-C6 alkyl or hydroxyalkyl; and
R$_4$ is a linear or branched C1-C6 alkyl or hydroxyalkyl.

Derivative molecules of certain embodiments are developed from the structure in 15B. In many embodiments, moieties, R-groups, or other fragments may be substituted by one or more of the following:

A is a fused ring (e.g., C3-C10 cycloalkyl);
X is CH or N;
Y is O, S, NH, NR$_3$;
R$_1$ is small alkyl (C1-C4) or halogen (e.g., Cl, Br, or F);
R$_2$ is phenyl, alkyl C1-C10, cycloalkyl (C3-C10), hydroxyalkyl (C1-C6), heteroaromatic (e.g., pyridyl, pyrazolyl, pyrolyl, pyrimidyl, thiophenyl, furanyl, or triazole), or heterocyclic C4-C6;
   where phenyl is optionally substituted with halogens (e.g., Cl, Br, or F),
   where an alkyl is linear or branched and optionally substituted with OH, OMe, OEt,
   where cycloalkyl is optionally substituted with one or more OH,
   where hydroxy alkyl is linear or branched
   where heteroaromatic is optionally substituted with small alkyls (C1-C6) or hydroxyalkyls (C1-C6), where alkyls and hydroxyalkyls are linear or branched,
   where heteroatom in hetrocyclic is optionally O, S, or NR$_4$;
R$_3$ is a C$_1$-C$_6$ alkyl (linear or branched); and
R$_4$ is a linear or branched C1-C6 alkyl or hydroxyalkyl.

In a number of embodiments, A is a C6 phenyl ring. In many embodiments, A is selected from the group consisting of:

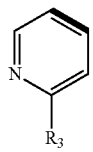 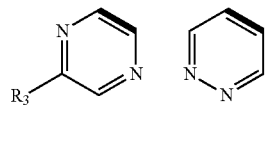 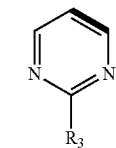 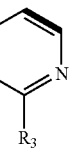

-continued

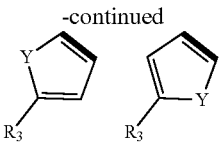

Figure 15C:
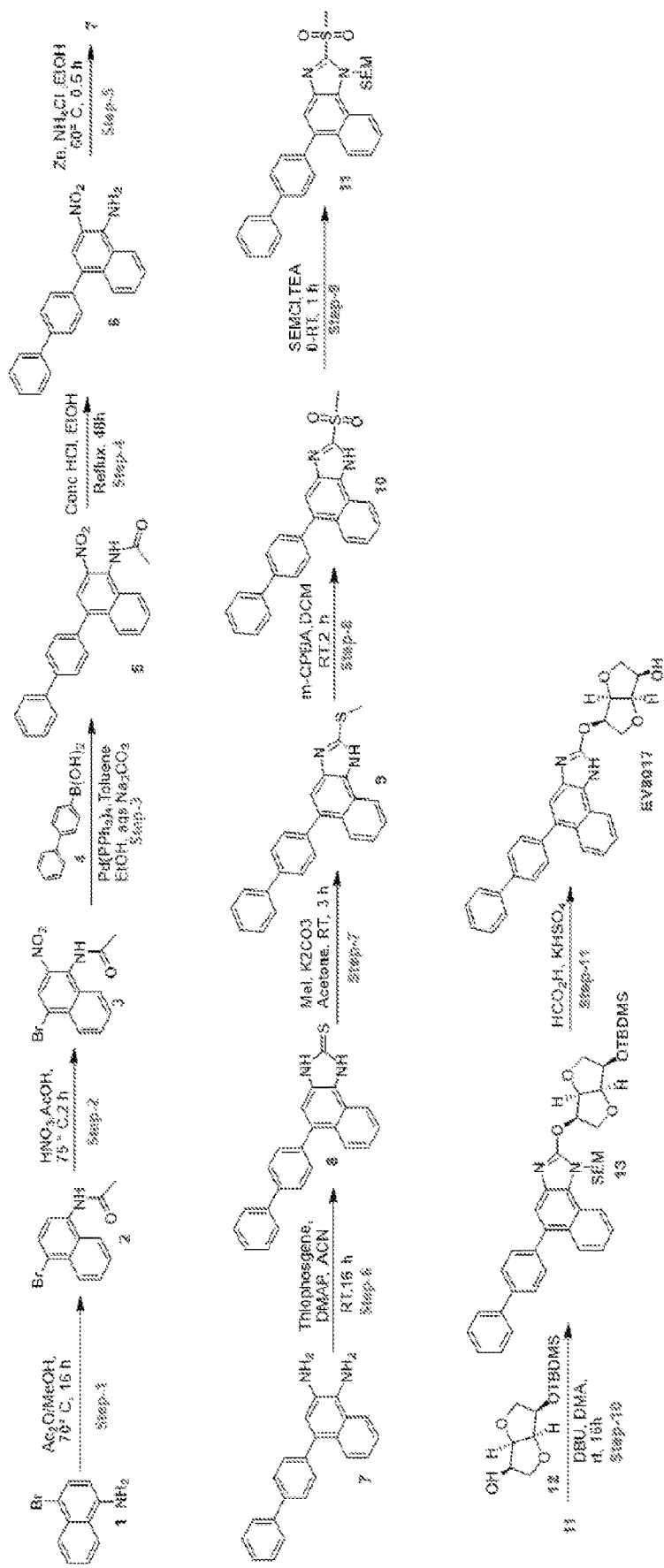
FIG. 15C illustrates a schematic of a method of synthesis of AMPK agonists in accordance with various embodiments.
Figure 15D:
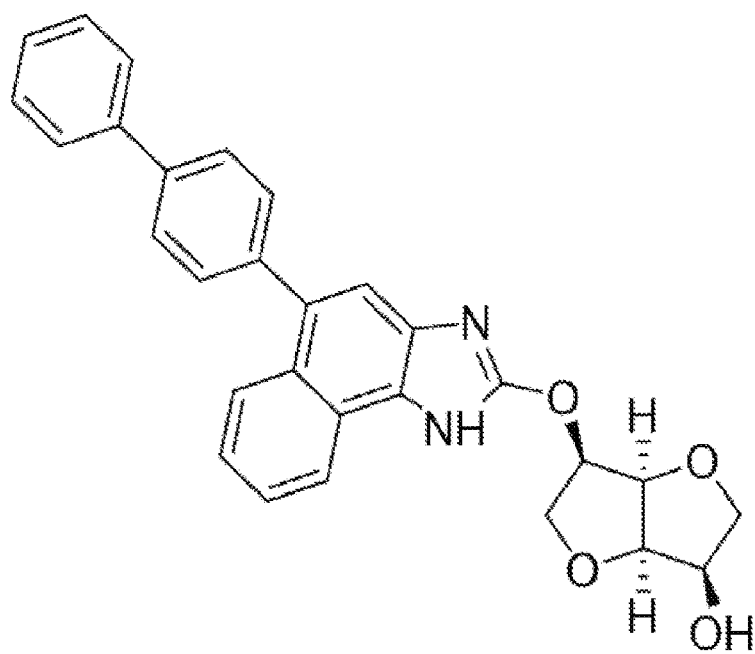
FIG. 15D illustrates a structure of an AMPK agonist in accordance with various embodiments.

Turning to FIG. 15C, a method of synthesizing embodiments is illustrated. Specifically, FIG. 15C illustrates a method to synthesize the embodiment illustrated in FIG. 15D (also referred to as EV8017). While the process of FIG. 15C generates the compound illustrated in FIG. 15D, it should be noted that additional compounds can be generated in a similar manner.

Figure 13A:
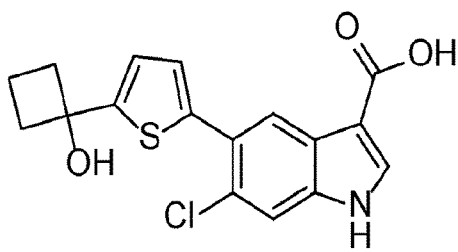
FIGS. 13A-13Z illustrate structures of AMPK agonists in accordance with various embodiments.
Figure 16A:
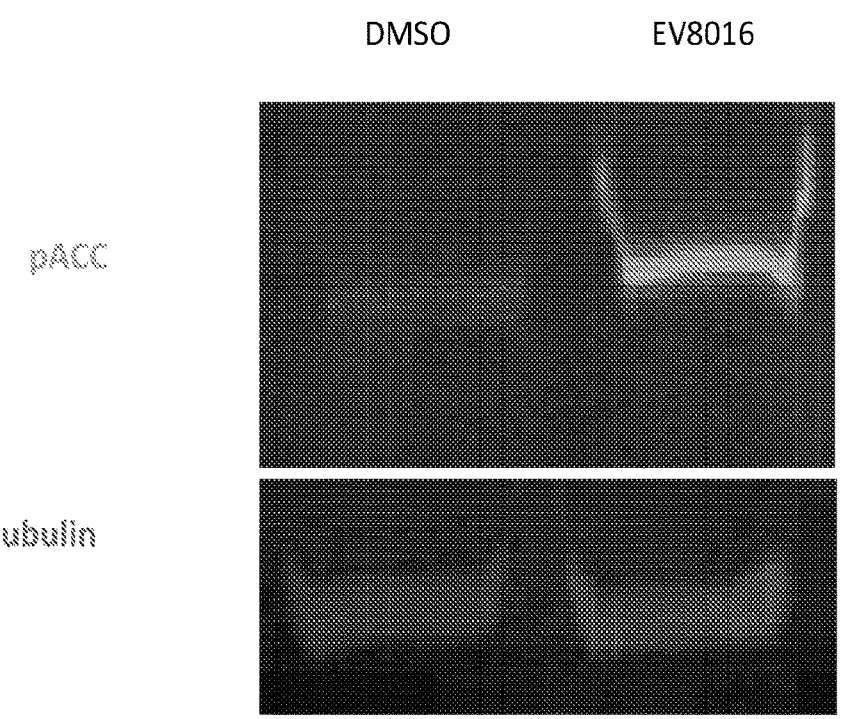
FIG. 16A illustrates results of ACC phosphorylation assay performed on mitochondrial deficient cells in accordance with various embodiments.

Turning to FIG. 16A, the biological effect of a novel AMPK agonist illustrated in FIG. 13A. In particular, FIG. 16A illustrates a western blot of phosphorylated ACC (pACC) in mitochondrial-defective patient cells treated with the embodiment illustrated in FIG. 13A (labeled EV8016) and vehicle-only treated cells (labeled DMSO). As noted above, in relation to FIG. 11F, phosphorylation of ACC is indicative of AMPK activation, thus indicating that compounds in accordance with many embodiments are capable of activating AMPK.

Figure 16B:
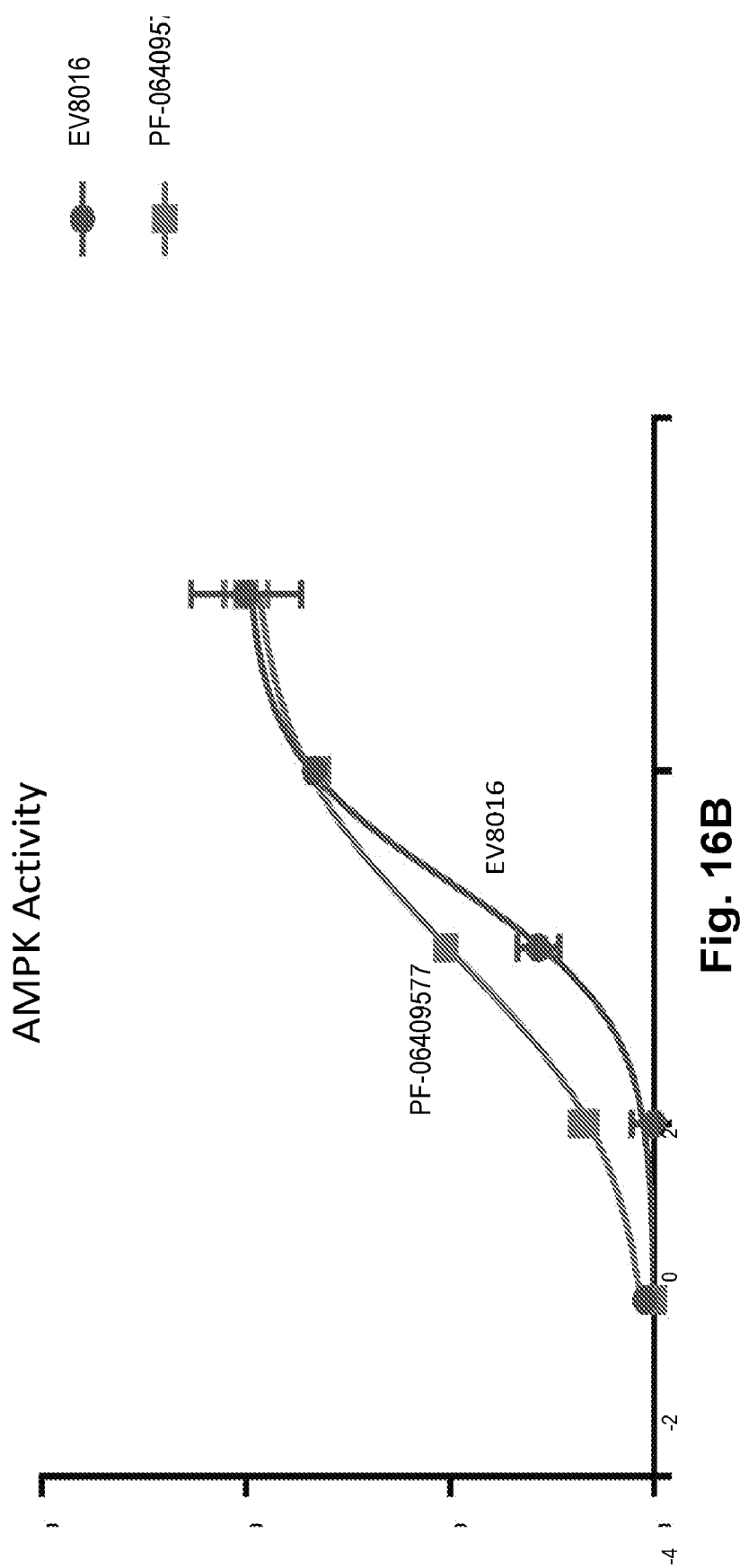
FIG. 16B illustrates AMPK activity of AMPK agonists used in determining EC50 in accordance with various embodiments.

Turning to FIG. 16B, EC50 of various embodiments of AMPK agonists can be determined. In the exemplary embodiment EV8016 (FIG. 13A), the EC50 was determined to be 232 nM, while the PF-06409577 embodiment (FIG. 1D) was determined to be 96 nM. One of skill in the art would appreciate and understand how to determine EC50 of additional embodiments.

Methods of Treating Individuals with AMPK Agonists

Figure 17:
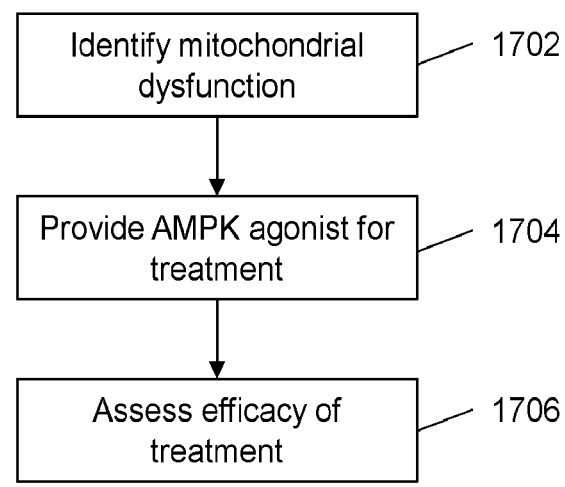
FIG. 17 illustrates a method of treating an individual in accordance with various embodiments.

Turning now to FIG. 17, various embodiments are directed to treating mitochondrial dysfunction in an individual in process 1700. In some embodiments, a mitochondrial dysfunction is identified in the individual at step 1702. In certain embodiments, individuals with dysfunction are discovered by exhibited symptoms, such as N-glycanase (NGLY1) deficiency, age-related macular degeneration (AMD), ischemic stroke, muscular dystrophies (e.g., Duchenne and Becker), Friedreich ataxia (FA), autoimmune disorders with muscle involvement (e.g., inclusion body myositis, Polymyositis, and Dermatomyositis), neurodegenerative disorders (e.g., Amyotrophic Lateral Sclerosis (ALS), Parkinson's Disease, and Alzheimer's Disease), diabetes, metabolic disorder, and/or obesity. In other embodiments, mitochondrial dysfunction will be identified based on molecular signatures of disease or dysfunction, such that protein blots (western blots), polymerase chain reaction (PCR), genotyping using genetic markers (e.g., single nucleotide polymorphisms (SNPs), expressed sequence tags (ESTs), simple sequence repeats (SSRs), etc.) will identify a particular disease or dysfunction present in the individual.

At step 1704, the individual is treated with an AMPK agonist in various embodiments. In some embodiments, the AMPK agonist is a direct (or AMP-independent) agonist, while in other embodiments, the AMPK agonist is an AMP-dependent agonist. Examples of direct agonists include PT1, ETC-1002, Salicylate, C991, C13, D561-0775, MT 63-78, A-769662, ZLN024, C24, MK-8722, PF-739, and PF-06409577. Examples of ATP-dependent agonists include metformin, resveratrol, and AICAR. In certain embodiments, the AMPK agonist is supplied to an individual at a therapeutically effective dose, where the therapeutically effective dose reduces, eliminates, or alleviates the consequences of mitochondrial dysfunction during and/ or after commencement of the therapy. In some embodiments, the AMPK agonist is provided orally, subcutaneously, intravenously, intraperitoneal injection, intranasal administration, dermal administration, via inhalation, intraocular (including intravitreal), and/or any method that provides a therapeutic effect. In certain embodiments, the AMPK agonist is formulated to provide a therapeutic effect. In some embodiments, the AMPK formulation includes a binding agent, a lubricating agent, a buffer, and/or a coating, which allows for a pharmacokinetic release of the AMPK agonist to provide the therapeutic effect.

Further, the AMPK agonist and/or formulation will be provided to the individual an appropriate dose and dosing schedule to provide a therapeutic effect. In some embodiments, the AMPK agonist will be provided as a single dose, while some embodiments will provide multiple doses over a course of time. In various embodiments, dosing will be accomplished as a concentration of a total volume, such that a dose will be 10 nM, 30 nM, 100 nM, 1 µM, 100 µM, or more, depending on the therapeutic effect. In additional embodiments, dosing will be in a ratio of mass of an AMPK agonist to mass of the individual being treated, such that a dose will be 1 mg/kg, 5 mg/kg, 10 mg/kg, 20 mg/kg, 50 mg/kg, 100 mg/kg, or more, depending on the therapeutic effect. In multiple-dosing embodiments, the dosing schedule can be 1 dose/day, 2 doses/day, 3 doses/day, or more and can continue for as long as necessary, such that the dosing can go for 1 week, 2 weeks, 3 weeks, 4 weeks, 5 weeks, 10 weeks, 20 weeks, or in perpetuity for the lifetime of the individual.

In further embodiments, the dose and/or dosing regimen will vary over the course of treatment depending on various factors, including achieving a threshold of enzyme activity. In some embodiments, a higher dose will be used to treat an individual and will be reduced after an amount of time, such that in various embodiments, a daily dose of 100 µM will be used for an amount of time, such as 1 week, 2 weeks, 4 weeks, or more, then the dose will be reduced for continuing treatment of an individual. In certain embodiments, the dosing regimen will change, such that the time between doses will change over the course of a treatment. For example, certain embodiments will provide daily doses of an AMPK agonist to an individual for an amount of time (e.g., 1 week, 2 weeks, 4 weeks, etc.) then will increase the amount of time between doses, such that subsequent doses will occur semi-weekly, weekly, or monthly for the rest of the treatment.

At step 1706, various embodiments will assess the individual for efficacy of the AMPK agonist. In certain embodiments, this step is accomplished by assessing the disease symptoms, such as those listed for step 1702, while in other embodiments, this step will be accomplished by looking at molecular profiles, such as genotyping, gene expression, and other methods as disclosed in reference to step 1702.

Methods of Modulating AMPK Activity

Figure 18:
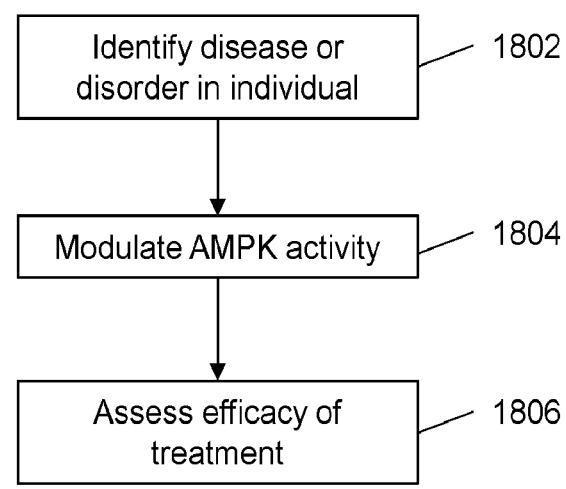
FIG. 18 illustrates a method of modulating AMPK activity in an individual in accordance with various embodiments.

Turning now to FIG. 18, various embodiments are directed to modulating AMPK activity to treat diseases or disorders in an individual, as illustrated in process 1800. In some embodiments, a disorder or disease is identified that is associated with mitochondrial dysfunction at step 1802. Examples of these diseases and/or disorders include the diseases and disorders identified in Tables 1-2, such that the disease and/or disorder is associated with mitochondrial dysfunction, such as primary mitochondrial dysfunction and/or secondary mitochondrial dysfunction. In various embodiments, the diseases and disorders are identified based on symptoms exhibited by an individual, while in some embodiments, diseases and disorders will be identified based on molecular signatures of disease or dysfunction, such that protein blots (western blots), polymerase chain reaction (PCR), genotyping using genetic markers (e.g., single nucleotide polymorphisms (SNPs), expressed sequence tags (ESTs), simple sequence repeats (SSRs), etc.).

At Step 1804, various embodiments will modulate AMPK activity. Modulating AMPK activity can be activating AMPK or inhibiting AMPK activity. In certain embodiments, AMPK activity will be activated by phosphorylating AMPK or providing an AMPK agonist. In certain embodiments, modulating is accomplished by inhibiting AMPK activity. Inhibition of AMPK can be accomplished using a competitive inhibitor or an allosteric inhibitor, which prevent AMPK from catalyzing a reaction.

At Step 1806, various embodiments will assess the individual for efficacy of the treatment. In certain embodiments, this step is accomplished by assessing the disease symptoms, such as those listed for step 1802, while in other embodiments, this step will be accomplished by looking at molecular profiles, such as genotyping, gene expression, and other methods as disclosed in reference to step 1802

EXEMPLARY EMBODIMENTS

Experiments were conducted to demonstrate the capabilities of the assays and inhibitors in accordance with embodiments. These results and discussion are not meant to be limiting, but merely to provide examples of operative devices and their features.

Materials & Methods

Fibroblasts previously derived from four patients with primary mitochondrial disease (Surf1, Complex I, Cox10, Polg), three patients with NGLY1 deficiency and four normal controls were used for the study. All samples were obtained with informed consent and approved by the Stanford IRB. Fibroblasts were maintained in DMEM medium containing 8.3 mM glucose and supplemented with 10% fetal bovine serum (FBS)(Fisher Scientific), 1% Penicillin-Streptomycin (10,000 U/mL)(Life Technologies), 1% glutaMAX (Life Technologies), 1% uridine (5 mg/ml) and 1% pyruvate (11 mg/ml) at 37° C., 5% $CO_2$.

For the screening of various compounds, $15 \times 10^3$ cells/500 ul media were seeded in quadruplets on 24 well microtiter plates. The following day, the medium was removed, wells washed with PBS and replaced with a mitochondrial stressor media containing DMEM, 1% Penicillin-Streptomycin (10,000 U/mL)(Life Technologies), 10% FCS (Fisher Scientific), 1 mM Galactose (Sigma Aldrich), and 25 µM sodium azide with or without the following compounds: 1 mM AICAR (Medchem Express), 1 mM Metformin (Sigma Aldrich), 100 µM PT1 (Santa Cruz Biotechnology), 100 µM A-769662 (Medchem Express), 100 µM C24 (Medchem Express). Following treatment with the various compounds, tissue cultures were analyzed for growth, oxygen consumption rate, and ATP levels.

Example 1: Cell Growth and Viability

Methods: Cell growth was measured by a fluorometric method using Calcein AM (Anaspec). Mitochondrial stressor media was removed, wells washed with PBS and then incubated with 500 ul/well of 800 nM Calcein AM in PBS for 30 min at 37 C, 5% CO2. Cell viability was measured by values obtained using a 485 nm excitation with the Flouroskan Ascent Microplate Fluorometer (Thermo Scientific).

Cellular ATP content was measured by LC-MS. Cells were trypsonized, washed with cold PBS, and lysed using NH4AC (0.05 M pH6). The lysate was transferred to a molecular weight cut-off filter (Chromsystems) and spun for 20 min at 4 C, 800×g. Following centrifugation, the supernatant was analyzed for DNA quantitation using the Nano-Drop ND-1000 (Nanodrop Technologies) and ATP quantitation by a 6400 Series Triple Quad LC/MS System (Agilent Technologies).

Fibroblasts in tissue culture were visualized by phase-contrast microscopy with a Leica DM IRB microscope at ×10 magnification, and images were taken with the Hamamatsu ORCA-ER camera.

Statistical significance (p<0.05) was calculated by 2-tailed student's t-test.

Results: Four direct activators of AMPK, PT1, A-769662, ZLN024, and C24, were tested on SURF1-deficient fibroblasts. The AMP analog AICAR, previously shown to improve mitochondrial function in vitro (Golubitzky, et al, PLoS One. 2011; 6(10); the disclosure of which is incorporated by reference herein in its entirety;) was included in the study design as a positive control. Mutant cells treated with direct AMPK agonists demonstrated a 35-55% increase in viability compared with untreated cells (i.e., cells treated with the vehicle DMSO) (FIG. 2A), with PT1 showing the largest improvement. A smaller but still significant effect was also seen in SURF1 cells treated with AICAR compared to the corresponding untreated control (i.e., cells treated with PBS), with mean cell survival increased by 57%.

To assess whether these findings extend to mitochondrial disorders beyond SURF1 deficiency, similar studies using fibroblasts from patients with deficiencies of mitochondrial complex I (CI), heme A:farnesyltransferase cytochrome c oxidase assembly factor (COX10), and mitochondrial DNA polymerase gamma (POLG) were performed. These studies therefore assessed a broad range of mitochondrial disruptions encompassing different components of the respiratory chain and mtDNA replication machinery. One compound, PT1, consistently and significantly improved survival in all mutant lines despite their different pathogenic mechanisms (FIGS. 2B-2D). The remaining compounds showed variable responses among the mutant lines: A-769662 improved survival in CI and POLG-deficient cells, ZLN024 improved survival in CI-deficient cells, and C24 improved survival in SURF1-deficient cell but not in any of the other lines. Interestingly, AICAR treatment also did not improve survival in any of the other lines except SURF1. Similar results were observed with fibroblasts from patients with NLGY-1 deficiency with up to 60% improvement in viability (FIG. 2E). Additionally, the newly developed AMPK agonists, MK-8722, PF-739, and PF-04609577, were tested and showed they improved the viability of surf1 patient cells similar to PT1, and that this improvement occurred in a dose dependent manner (FIG. 2E). Additionally, the cell morphology improved with treatment with PT1 on SURF1 (FIG. 3B), COX10 (FIG. 3D), CI (FIG. 3F), POLG (FIG. 3H), and NGLY1 FIG. 3J) deficient fibroblasts over untreated cells (FIGS. 3A, 3C, 3E, 3G, AND 3I), where the untreated cells show exhibit bright apoptotic cells. Additionally, MK-8722 (FIG. 3L), PF-739 (FIG. 3M), and PF-04609577 (FIG. 3N) improved cell morphology in SURF1-deficient fibroblasts over untreated fibroblasts (FIG. 3K), where the untreated cells show exhibit bright apoptotic cells are illustrated.

Conclusion: These results indicate that direct AMPK activation improves cell viability across a range of primary and secondary mitochondrial disease etiologies, which is supported by improved cell morphology seen in mutant cells treated with PT1 compared to cells treated with DMSO.

Example 2: Measuring AMPK Agonist on AMPK

Methods: Western blotting was performed to identify pAMPK levels in cells treated with PT1. Cells were lysed with RIPA buffer supplemented with Na-Orthovanadate, PMSF, and Protease Inhibitor cocktail. Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 min, the membrane was washed once with TBST and incubated with antibodies against AMPK (1:1,000), pAMPK (1:1,000), actin (1:10,000) at 4° C. overnight. Membranes were washed three times for 5 min and incubated with a 1:10,000 dilution of horseradish peroxidase-conjugated anti-mouse or anti-rabbit antibodies for 2 h. Blots were washed with TBST three times and developed with the ECL system (Thermo Scientific) according to the manufacturer's protocols.

To test whether the cellular response to PT1 is a result of AMPK activation itself, or is merely a result of nonspecific interactions, an siRNA knockdown strategy was used. siRNA for PRKAA1 (s101) and a negative control (Life Technologies) were incubated with Hiperfect reagent (Qiagen) in media containing DMEM, 1% Penicillin-Streptomycin (10,000 U/mL) (Life Technologies), 1% glutaMAX (Life Technologies) but no serum and allowed to complex for 10 min at room temperature. The complex was then added to COX10 patient tissue cultures in 6-well microtiter plates (final siRNA concentration of 10 nM of each siRNA) and incubated for 72 hr at 37° C., 5% $CO_2$. At the end of the incubation period, the cells were analyzed for levels of AMPK and pAMPK by western blot analysis (see protocol above) or incubated for six additional days with PT1 (or DMSO as untreated control) and assessed for viability by Calcein AM. COX10-deficient fibroblasts were treated with PT1 and either siAMPK or siCNT, and responses were evaluated for pAMPK protein expression by western blotting (FIG. 4A), cell viability by Calcein AM fluorescence assay (FIG. 4B), and cell morphology by phase contrast microscopy (FIGS. 4C-4F)

Results: Cultured fibroblasts from SURF1 deficient patient cells were treated with PT1 for 0 hr, 2 hr, 24 hr and 48 hr and pAMPK levels measured. pAMPK levels increased by 2 hours post–PT1 treatment, and peaked at 24 hr with return to baseline at 48 hrs (FIG. 5A). Treatment with PT1 together with selective knockdown of AMPK (PT1+siAMPK) resulted in a 63% decrease in pAMPK levels and 41% decrease in cell viability compared to control conditions (PT1+siCNT), consistent with the idea that cellular response to PT1 is mediated by AMPK activation. Following 48 hr treatment with PT1, the peroxisome proliferator-activated receptor gamma coactivator 1-alpha (PGC-1a), a master regulator of mitochondrial biogenesis, increased by 2.4-fold (FIG. 5B). Similarly, catalase and manganese superoxide dismutase (SOD2), two of the main antioxidant genes regulated by AMPK, increased by 1.3-fold and 1.5-fold, respectively (FIGS. 5C-5D).

Conclusion: PT1's mechanism of action addresses the main metabolic disruptions caused by mitochondrial dysfunction; therefore stimulating mitochondrial biogenesis and triggering the oxidative stress response through AMPK activation.

Example 3: Oxygen Consumption and Cellular Respiration

Background: To determine if the upregulation of PGC-1 with PT1 treatment was associated with improved mitochondrial respiration, oxygen consumption rates (OCR) were evaluated in both SURF1 and POLG patient fibroblasts.

Methods: Oxygen consumption rate (OCR) was measured using an XF96 extracellular flux analyzer (Seahorse Biosciences). Fibroblasts were seeded at 10×103 cell/well in 100 ul media containing 8.3 mM glucose and supplemented with 10% fetal bovine serum (FBS) (Fisher Scientific), 1% Penicillin-Streptomycin (10,000 U/mL)(Life Technologies), 1% glutaMAX (Life Technologies), 1% uridine (5 mg/ml) and 1% pyruvate (11 mg/ml) on an XF 96 well plate at 37° C., 5% CO2. The following day the medium was replaced with the mitochondrial stressor media (details above) with or without PT1, A-769662, and AICAR. After 48 hours the stressor media was replaced with 175 µl unbuffered XF base DMEM medium (Fisher Scientific) with the same constituents as the mitochondrial stressor medium and incubated at 37° C. for 30 min for equilibrium before the measurements. OCR Baseline measurements were measured three times, once every five minutes. After the experiment, cell content was estimated by Calcein AM fluorescence intensity (FI) and OCR was calculated as OCR divided by FI.

Results: Despite distinct etiologic differences, both Surf1 and POLG patient cells treated with PT1 demonstrated a roughly 30% improvement in basal respiration (FIGS. 6A-6B), while PT1 demonstrated a 16% increase in basal OCR in NGLY1 patient cells (FIG. 6C).

The fraction of basal mitochondrial oxygen consumption used for ATP synthesis (ATP-coupled respiration) also improved by 40% in Surf1 and 30% in POLG, demonstrating PT1's positive effect on the coupling efficiency of oxidative phosphorylation (FIGS. 6D-6E).

Maximal respiration capacity, which reflects the cells' ability to respond to increased ATP demand, improved in both Surf1 and POLG cells, with a 50% and 20% increase, respectively (FIGS. 6F-6G), while PT1 demonstrated a 40% increase in maximal OCR in NGLY1 patient cells (FIG. 6H).

Conclusion: Activating AMPK through an AMP-independent mechanism may be a more suitable mechanism by which to target mitochondrial dysfunction.

Example 4: Measuring Oxidative Stress and Energy Status

Background: ATP and ROS content reflect cellular energy and oxidative status, both of which are dependent on effective ATP-coupled respiration and overall mitochondrial function. Mitochondrial dysfunction causes an incomplete electron transfer through the RC, leading to decreased ATP synthesis and over-production of reactive oxygen species (ROS). (Atkuri et al, Proc Natl Acad Sci USA. 2009 Mar. 10; 106(10):3941-5; Enns et al, PLoS One. 2014 Jun. 18; 9(6); the disclosures of which are incorporated by reference herein in their entirety.)

Methods: SURF1, POLG, and NGLY1 patient cells were supplemented with PT1 or DMSO (untreated control) for 48 hrs (n=3) and ATP levels measured by the CellTiter-Glo ATP Assay or for 72 hrs (n=3) and ROS levels were measured by the CellROX Deep Red Flow Cytometry Assay. Results were normalized to total protein concentration. Data are represented as the mean±standard error of the mean. Statistical significance was measured to $p<0.05$.

Results: ATP content increased with treatment by 35% in Surf1, 36% in POLG, and 40% in NGLY1 patient cells, and compared to DMSO treated cells, ROS levels decrease by 10%, 15%, and 18% respectively (FIGS. 7A-7F).

Conclusion: Consistent with the observed upregulation of ATP-coupled respiration and expression of the antioxidants Catalase and SOD2 (Example 2; FIGS. 5C-5D), both the energy deficiency and oxidative stress improved with PT1 treatment in cells from patients with either primary or secondary mitochondrial dysfunction.

Example 5: Measuring Effect on AMD

Methods: To generate an AMD model, mice were treated with 100 mg/kg of PT1 (or vehicle) 24 hrs and 12 hrs prior to SI (or vehicle) treatment, then treated every 24 hrs for 3 days post-SI. Both PT1 and SI were delivered by intraperitoneal (IP) injections and animals were phenotyped 3 days post-SI administration.

Mice were anesthetized and their pupils dilated using 1% atropine sulfate, 2.5% phenylephrine hydrochloride, and 0.5% proparacaine hydrochloride. Funduscopy was performed using the Micron III small animal retinal imaging AD camera (Phoenix Research Laboratories, INC).

Retinal function was evaluated by recording of dark- and light-adapted ERG (Espion E2 System, Diagnosys LLC). Mice were dark adapted overnight before ERG recording, and all procedures were performed in the dark or under dim red light. Mice were anesthetized and their pupils dilated as described above. For the ERG recordings, electrodes were placed on the center of cornea. A ground needle electrode was placed in the base of the tail, and reference needle electrode was placed subdermally between the eyes. The a-wave amplitude was measured from the baseline to the trough of the a-wave, and b-wave amplitude was measured from the trough of the a-wave to the peak of the b-wave.

Results: Fewer white deposits are observed in PT1 treated mice (+SI; +PT1) compared to untreated mice (+SI; −PT1) (n=5 mice per group). PT1 treatment alone (—SI; +PT1) does not alter funduscopy results, closely resembling control mice (−SI; −PT1) (FIG. 9A). H&E staining of retinal sections shows PT1 treatment (+SI; +PT1) protects against ONL thinning (white bars), prevents alterations in photoreceptor IS/OS morphology, and decreases melanin debris (black arrows) compared to untreated mice (+SI; −PT1) (n=5 mice per group) (FIG. 9B). ONL thickness in PT1 treated mice (+SI; +PT1) is similar to control mice (−SI; −PT1) and is significantly improved compared to untreated mice (+SI; −PT1). PT1 treatment alone does not alter ONL thickness (−SI; +PT1 vs. —SI; −PT1)(n=3-4 mice per group) (FIG. 9C). Electroretinography demonstrates significantly increased rod responses (scotopic a-wave and b-wave) in PT1 treated mice (+SI; +PT1) compared to untreated mice (+SI; −PT1) (n=3-4 mice per group) (FIG. 9D).

Conclusion: PT1 demonstrates improvements in retinas exhibiting AMD, thus indicating a positive use of AMPK agonists as a treatment for AMD.

Example 6: Neuroprotection in Ischemic Stroke

Methods: To generate an ischemic stroke model, ischemic lesions were induced by transiently occluding the middle cerebral artery for 45 minutes, followed by reperfusion.

Mice were then injected intraperitoneally with either 100 mg/kg of PT1 or vehicle in two doses, 1 hour and 24 hours post-occlusion, and sacrificed one hour later for terminal tissue collection.

Isolated brains were placed in cold saline for 20 minutes, sliced in seven coronal slices (2 mm thick), and stained in a 1.0% 2,3,5-triphenyltetrazolium chloride (TTC) solution in saline at 37° C. for 30 minutes. The stained brain tissues were fixed in 10% formalin in phosphate-buffered saline. The images were captured using a CCD camera (Panasonic Corporation, Japan) and the unstained damaged areas were defined as infarcted tissue and were quantified using Image Pro Plus 4.1 software (Media Cybernetics, Silver Spring, MD).

Results: TCC-stained brain slices from mice treated with PT1 showed a reduction in size of the infarcted regions (white) compared to mice treated with vehicle (FIGS. 10B-10C).

Conclusion: PT1 treatment showed a striking attenuation of the ischemic (stroke) area in brain slices from mice treated with PT1 compared with untreated controls.

Example 7: Enhancement of Motor Performance

Background: As a high-energy demand organ, the eye is particularly susceptible to the consequences of mitochondrial damage. Similarly, skeletal muscle is also a high-energy organ that relies on both oxidative phosphorylation and glycolysis for energy production.

Methods: To examine the effects of AMPK agonists on in vivo systems with mitochondrial dysfunction, MK8722 was used to treat a mouse model of mitochondrial disease. These mice have mitochondrial Complex IV deficiency caused by deficient cytochrome C oxidase assembly protein, SCO2, and harbor a Sco2 knock-out (KO) allele and a Sco2 knock-in (KI) allele expressing an E→K mutation at position 129 (E129K). The E129K mutation corresponds to the E140K mutation found in almost all human SCO2-mutated patients. (See e.g., Yang et al, Analysis of mouse models of cytochrome c oxidase deficiency owing to mutations in Sco2. Hum Mol Genet. 2010 Jan. 1; 19(1):170-80; the disclosure of which is incorporated by reference herein in its entirety.) The predominant phenotype of Sco2 deficient mice is reduced locomotor function and ocular defects, both common findings in patients with primary mitochondrial disease. The Sco2 mice were grouped into four treatment groups: Sco2 KI/KO+MK8722, Sco2 KI/KO+DMSO (vehicle), Control KI/WT+MK8722, Control KI/WT+DMSO with 7-9 mice per group. 1.5-month old Sco2 mice were treated once daily by oral gavage with MK8722 (10 mg/kg) or vehicle (DMSO) for 14 weeks. Locomotor function was evaluated using the activity chamber, rotarod, and hanging-wire tests and ocular structure using optical coherence tomography (OCT).

Results: As a result of this sensitivity to mitochondrial dysfunction, ocular structure measured in vivo by Optical Coherence Tomography (OCT) revealed retinal defects in both Sco2 KI/KO as well as the heterozygous KI/WT littermates. The thickness of the retinal nerve fiber layer (RNFL) was reduced in Sco2 KI/KO and KI/WT mice compared to WT/WT controls (KI/KO Veh: 74.1 µm and KI/WT Veh: 72.7 µm versus WT/WT Veh: 76.2 µm). By contrast, the RNFL in the MK8722-treated mice was thicker than the vehicle-treated Sco2 KO/KI and KI/WT mice (KI/KO Veh: 74.1 µm versus KI/KO MK8722: 77 µm and KI/WT Veh: 72.7 µm vs. KI/WT MK8722: 74.7 µm) (see FIG. 9E).

In the locomotor function studies evaluating muscle performance, MK8722-treated Sco2 KI/KO mutant mice outperformed the vehicle-treated Sco2 KI/KO mutant mice in the activity chamber (See FIG. 11A), rotarod running test (See FIG. 11B), and fore limb wire hang test (See FIG. 11C). As seen in FIG. 11A, vehicle-treated Sco2 KI/KO mice moved less distance in the activity chamber compared to the KI/WT littermate controls and 8 weeks of MK8722 treatment restored their activity to control levels (KO/KI Veh: 1516.7 cm; KO/KI MK8722: 2337.8 cm; KI/WT Veh: 2337 cm). FIG. 11B illustrates that MK8722 treatment also improved the rotarod running time of KI/KO mutant mice compared to vehicle-treated mice to levels similar to the controls (KO/KI Veh: 176.1 sec; KO/KI MK8722: 248.1 sec; KI/WT Veh: 235.7 sec). For the hanging wire test, FIG. 11C shows that MK8722 treatment increased the length of time Sco2 KO/KI mutant mice could hang by their four limbs to levels even above that of the KI/WT controls (KO/KI Veh: 173.2 sec; KO/KI MK8722: 312.5 sec; KI/WT Veh: 145.5 sec).

FIG. 11D shows the intensity of histological stains indicative of mitochondrial cytochrome C oxidase (CytoC) and succinate dehydrogenase (SDH) activities are increased in the skeletal muscle tissue of MK8722-treated Sco2 KI/KO mutant mice compared to vehicle-treated mutant mice. Similarly, FIG. 11E shows an increased glycogen content upon histological assessment of skeletal muscle in Sco2 KI/KO mutant mice treated with MK8722 compared to untreated mice. The increase in locomotor function (FIGS. 11A-11C) and mitochondrial function (FIGS. 11D-11E), was associated with an increase in ACC phosphorylation, as seen in FIG. 11F.

Conclusion: The retinal study (FIG. 9E) demonstrates that activation of AMPK can improve and/or prevent ocular damage associated with mitochondrial dysfunction. Additionally, the locomotor studies (FIGS. 11A-11C) demonstrate that AMPK activation can enhance strength, endurance, and overall locomotor function in muscle degenerative disorders associated with mitochondrial dysfunction. Further, the increased mitochondrial function (FIG. 11D) and glycogen content (FIG. 11E) may play an integral part of the mechanism of action by which energy levels are normalized within the skeletal muscle, thereby preventing degeneration and weakness. Coupled with the increased ACC phosphorylation indicative of increased AMPK activation, these results demonstrate the ability of AMPK agonists of many embodiments to have many pharmacological benefits.

Example 8: Synthesizing 6-chloro-5-(5-(1-hydroxy-cyclobutyl)thiophen-2-yl)-1H-indole-3-Carboxylic Acid and Analogs Thereof Background: FIG. 12A illustrates a generalized structure of a compound capable of activating AMPK. The synthesis of four derivatives (FIGS. 13A-13B and FIG. 14J-14K) are described in this example.

Methods: A graphical illustration of this example is illustrated in FIG. 12B, and while this example illustrates the synthesis of the compound illustrated in FIG. 13A, one of skill in the art would understand the use of different reagents, reactants, conditions, etc. to generate derivative compounds, including those illustrated in FIGS. 13B-13Z and FIGS. 14A-14O.

Step 1: 1-(5-bromothiophen-2-yl)cyclobutan-1-ol—To a stirred solution of 2,5-dibromothiophene (0.95 g, 3.922 mmol) in dry THF at −78° C., n-butyl lithium was added (2.69 ml, 4.314 mmol) drop wise at −78° C. and the mixture was allowed to stir for another 30 min at the same temp. Then a solution of cyclobutanone (0.27 g, 3.922 mmol) was slowly added over 2 min and the reaction mixture was allowed to stir at −78° C. for 1 h and then quenched with ammonium chloride. The product was extracted into ethyl acetate, dried over sodium sulfate, evaporated under reduced pressure and then purified by Flash chromatography (230-400 mesh, 10% EA in PE) to give 1-(5-bromothiophen-2-yl)cyclobutan-1-ol (0.6 g; 66%) as a colorless liquid.

Step 2: 1-(5-(4,4,5,5-tetramethyl-1,3,2-dioxaborolan-2-yl)thiophen-2-yl)cyclobutan-1-ol—A mixture of the product of Step 1 (2.0 g, 8.579 mmol), Bispinacalatodiboron (3.2 g, 12.87 mmol) and KOAc (2.25 g, 25.7 mmol) in 1,4-dioxane (20 ml) was purged with N2 gas for 5 minutes and then Pd(dppf)Cl$_2$ (0.32 g, 0.429 mmol) was added. After stirring for 16 h at 90° C. the solvent was removed by evaporation under reduced pressure and the residue was purified by column chromatography over florisil, eluting with 0-10% EA/PE, to give 1-(5-(4,4,5,5-tetramethyl-1,3,2-dioxaborolan-2-yl)thiophen-2-yl)cyclobutan-1-ol (0.6 g; 25%) as a gummy solid.

Step 3: Methyl 6-chloro-5-(5-(1-hydroxycyclobutyl)thiophen-2-yl)-1H-indole-3-carboxylate—A mixture of the product of Step 2 (0.275 g, 0.977 mmol), methyl 5-bromo-6-chloro-1H-indole-3-carboxylate (0.282 g, 0.977 mmol), K2CO3 (0.40 g, 2.931 mmol) in 1,4-dioxane (5 ml) and water (1 ml) was purged with N$_2$ gas for 5 minutes. Pd(dppf)Cl$_2$·DCM (0.04 g, 0.048 mmol) was then added and the resulting solution was stirred for 16 h at 100° C. The solvent was removed by evaporation under reduced pressure and the residue was purified by column chromatography over florisil by eluting with 0-10% EA/PE, to give methyl 6-chloro-5-(5-(1-hydroxycyclobutyl)thiophen-2-yl)-1H-indole-3-carboxylate (0.15 g; 91%) as an off white solid.

Step 4: 6-chloro-5-(5-(1-hydroxycyclobutyl)thiophen-2-yl)-1H-indole-3-carboxylic acid—To a stirred solution of the product of Step 3 (0.150 g, 0.414 mmol) in ethanol and 6N NaOH solution (10 ml) was stirred for 16 h at 80° C. The solvent was removed by evaporation under reduced pressure and the residue was acidified with citric acid and the product was extracted into ethyl acetate. After washing the extract with water and drying with sodium sulfate the solvent was removed under reduced pressure and the crude residue was purified by prep-HPLC to give 6-chloro-5-(5-(1-hydroxycyclobutyl)thiophen-2-yl)-1H-indole-3-carboxylic acid (0.06 g; 42%) as an off-white powder.

Figure 13B:
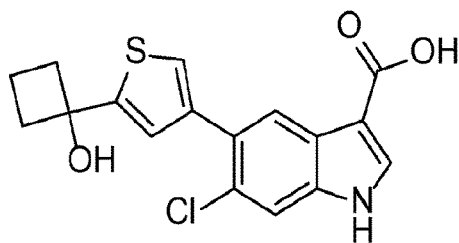
Figure 13C:
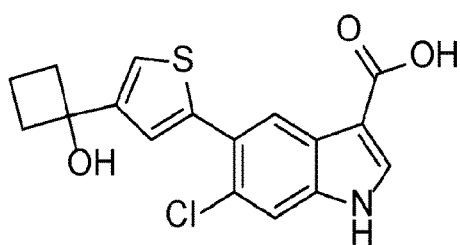
Figure 13D:
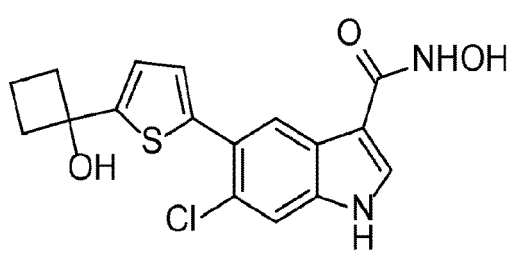
Figure 13E:
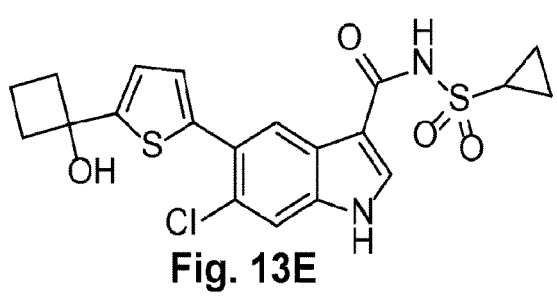
Figure 14A:
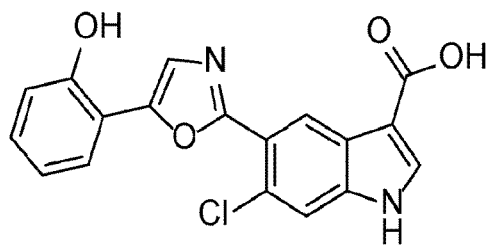
FIGS. 14A-14O illustrate structures of AMPK agonists in accordance with various embodiments.
Figure 14B:
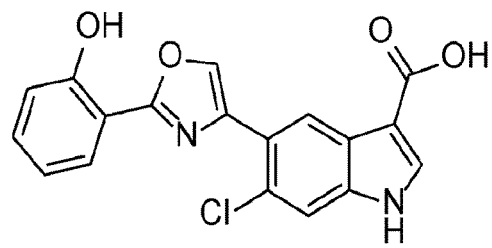
Figure 14C:
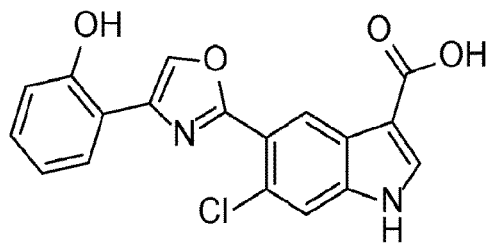
Figure 14D:
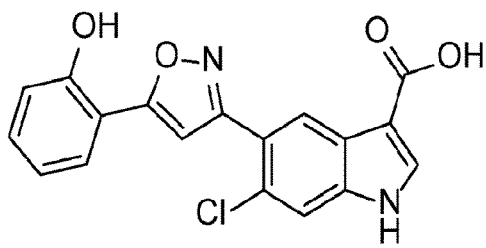
Figure 14E:
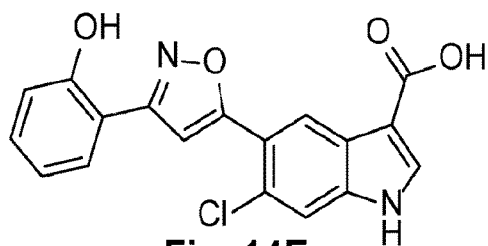
Figure 14F:
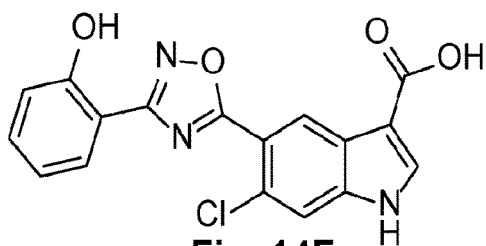
Figure 14G:
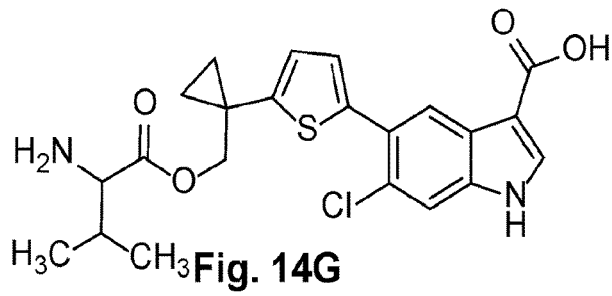
Figure 14H:
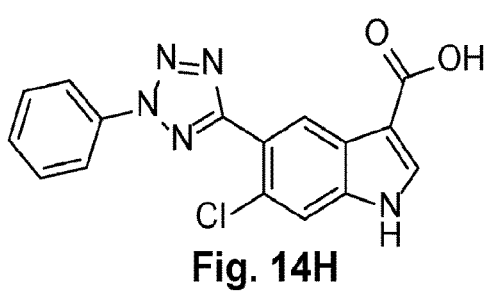
Figure 14I:
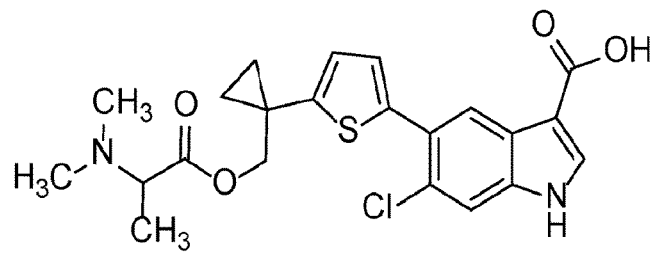
Figure 14J:
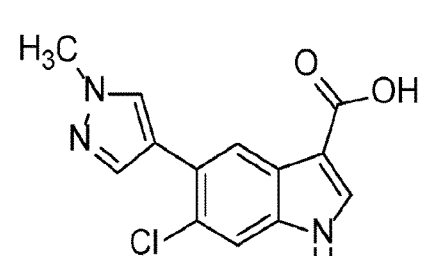
Figure 14K:
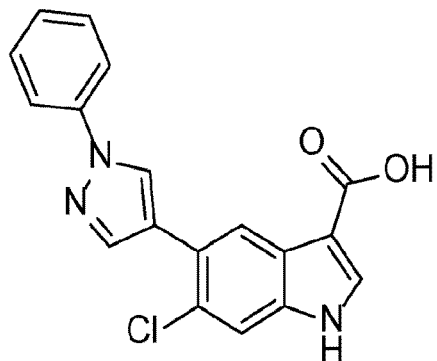

By altering certain reagents, the methodology described above in relation to FIG. 12B were also be used to generate 6-chloro-5-(5-(1-hydroxycyclobutyl)thiophen-3-yl)-1H-indole-3-carboxylic acid (FIG. 13B), 6-chloro-5-(1-methyl-1H-pyrazol-4-yl)-1H-indole-3-carboxylic acid (FIG. 14J), and 6-chloro-5-(1-phenyl-1H-pyrazol-4-yl)-1H-indole-3-carboxylic acid (FIG. 14K).

Results: Step 1 produced 1-(5-bromothiophen-2-yl)cyclobutan-1-ol with the following characteristics: $^1$H NMR (400 MHz, CDCl3): δ 6.91 (d, J=3.6 Hz, 1H), 6.81 (d, J=4.0 Hz, 1H), 2.49-2.36 (m, 4H), 2.21 (s, 1H), 1.96-1.91 (m, 1H), 1.76-1.69 (m, 1H). LCMS: 97.6% (217.07, M-18).

Step 3 produced Methyl 6-chloro-5-(5-(1-hydroxycyclobutyl)thiophen-2-yl)-1H-indole-3-carboxylate with the following characteristics: $^1$H NMR (400 MHz, CDCl3): δ 8.56 (bs, 1H), 8.29 (s, 1H), 7.93 (d, J=2.8 Hz, 1H), 7.54 (s, 1H), 7.16 (d, J=3.6 Hz, 1H), 7.06 (d, J=3.6 Hz, 1H), 3.92 (s, 3H), 2.65-2.58 (m, 2H), 2.51-2.44 (m, 2H), 2.31 (s, 1H), 1.99-1.91 (m, 1H), 1.84-1.80 (m, 1H). LCMS: 95.63% (344.23, M-18).

Step 4 produced 6-chloro-5-(5-(1-hydroxycyclobutyl)thiophen-2-yl)-1H-indole-3-carboxylic acid with the following characteristics: $^1$H NMR (400 MHz, DMSO-d6): δ 12 (br s, 1H), 8.12 (s, 1H), 8.07 (s, 1H), 7.63 (s, 1H), 7.12 (d, J=3.6 Hz, 1H), 7.06 (d, J=3.6 Hz, 1H), 5.96 (s, 1H), 2.45-2.31 (m, 4H), 1.91-1.82 (m, 1H), 1.78-1.68 (m, 1H). LCMS: 99.06% (465.30 [M+H]+), melting range: 228-232° C.

FIG. 13B illustrates 6-chloro-5-(5-(1-hydroxycyclobutyl)thiophen-3-yl)-1H-indole-3-carboxylic acid, which has $^1$H NMR (400 MHz, DMSO-d6): δ 11.90 (bs, 1H), 8.04 (s, 1H), 7.60 (s, 1H), 7.42 (d, J=1.2 Hz, 1H), 7.20 (d, J=1.6 Hz, 1H), 5.96 (s, 1H), 2.44-2.32 (m, 4H), 1.91-1.82 (m, 1H), 1.77-1.70 (m, 1H), LCMS: 97.92% (346.51 [M+H]+), and Melting Range: 248-252° C.

FIG. 14J illustrates 6-chloro-5-(1-methyl-1H-pyrazol-4-yl)-1H-indole-3-carboxylic acid, which has $^1$H NMR (400 MHz, DMSO-d6): δ 12.09 (s, 1H), 11.87 (s, 1H), 8.04 (d, J=2.4 Hz, 2H), 8.01 (s, 1H), 7.67 (s, 1H), 7.59 (s, 1H), 3.90 (s, 1H), LCMS: 99.32% (276.31 [M+H]+), and Melting range: 241-245° C.

FIG. 14K illustrates 6-chloro-5-(1-phenyl-1H-pyrazol-4-yl)-1H-indole-3-carboxylic acid, which has $^1$H NMR (400 MHz, DMSO-d6): δ 11.86 (br s, 1H), 8.77 (s, 1H), 8.20 (br s, 1H), 8.00 (s, 2H), 7.93 (d, J=7.6 Hz, 1H), 7.63 (s, 1H), 7.52 (t, 2H), 7.33 (t, 1H), LCMS: 97.20% (338.13 [M+H]+), and Melting Range: 245-249° C.

Conclusion: Embodiments are capable of synthesizing novel AMPK agonists and derivates thereof, such as those illustrated in FIGS. 13B-13Z and FIGS. 14A-14O.

Example 9: Synthesizing Analogs of EV8016 (FIG. 13A)

Background: FIG. 12A illustrates a generalized structure of a compound capable of activating AMPK. The synthesis of additional derivatives (FIG. 13F and FIGS. 14L-14M) are described in this example.

Methods: A graphical illustration of this example is illustrated in FIG. 12C, and while this example illustrates the synthesis of the compound illustrated in FIG. 14L, one of skill in the art would understand the use of different reagents, reactants, conditions, etc. to generate derivative compounds, including those illustrated in FIGS. 13A-13Z and FIGS. 14A-14O.

Figure 13F:
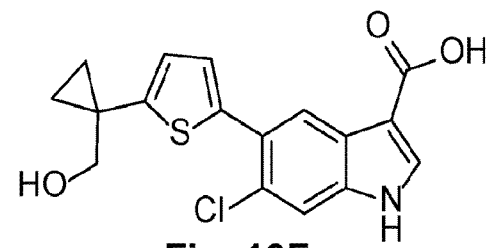
Figure 13G:
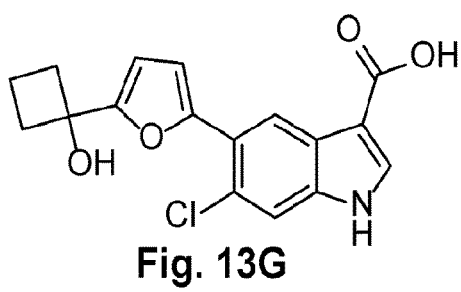
Figure 13H:
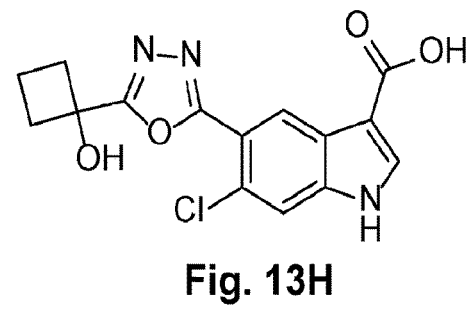
Figure 13I:
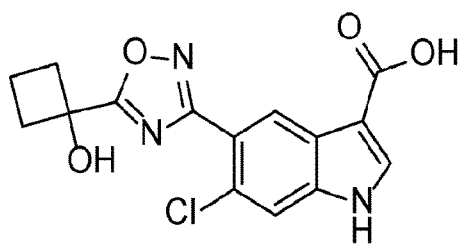
Figure 13J:
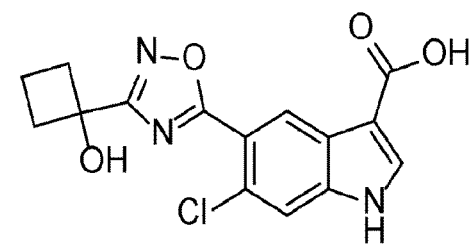
Figure 13K:
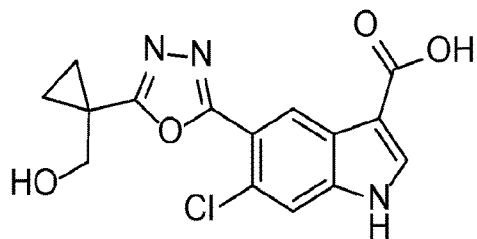
Figure 13L:
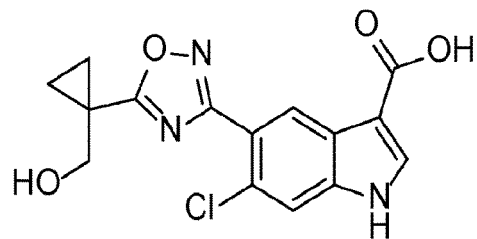
Figure 13M:
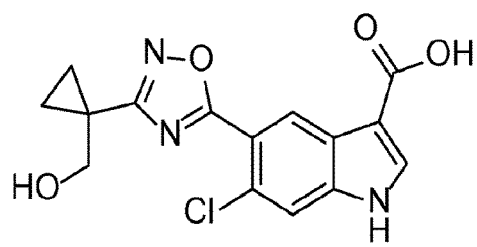
Figure 13N:
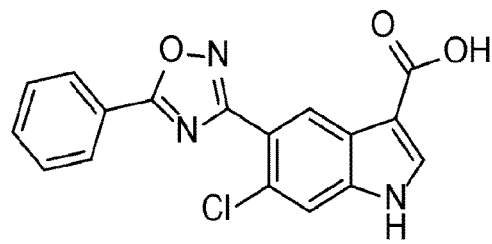
Figure 13O:
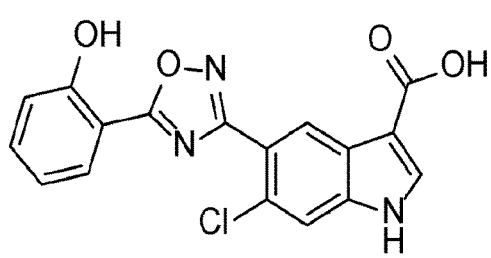
Figure 13P:
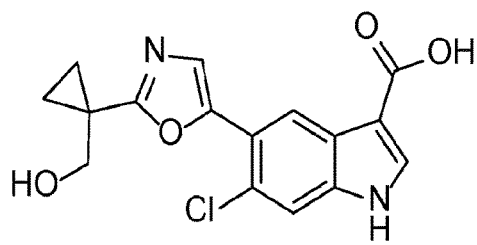
Figure 13Q:
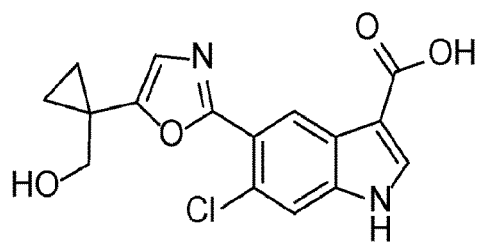
Figure 13R:
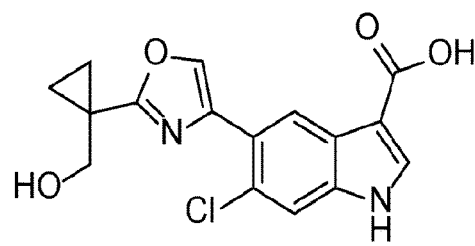
Figure 13S:
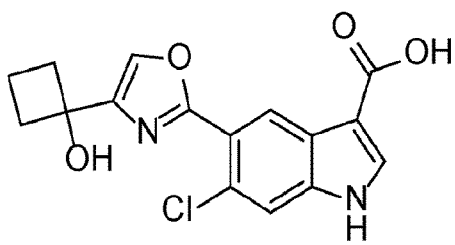
Figure 13T:
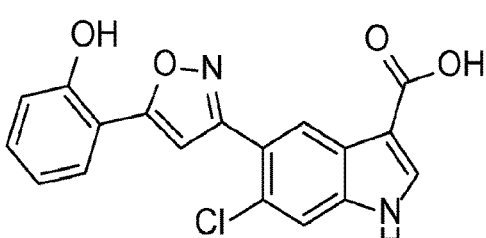
Figure 13U:
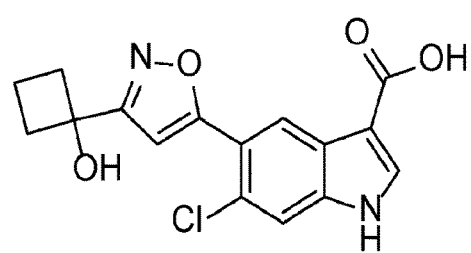
Figure 13V:
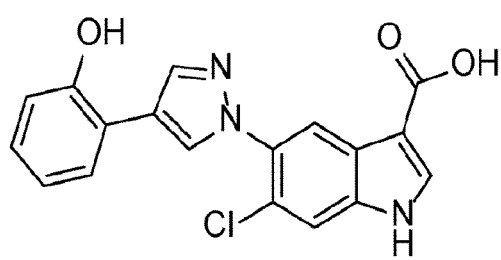
Figure 13W:
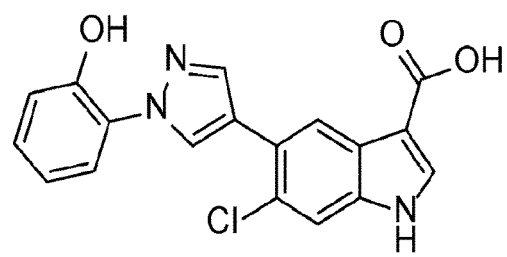
Figure 13X:
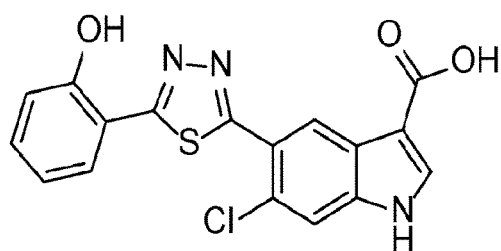
Figure 13Y:
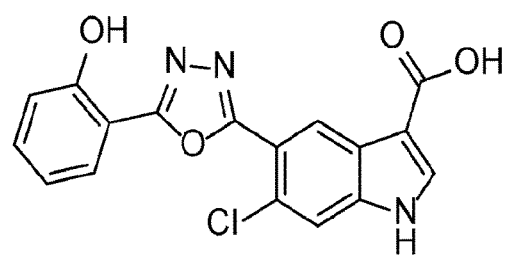
Figure 13Z:
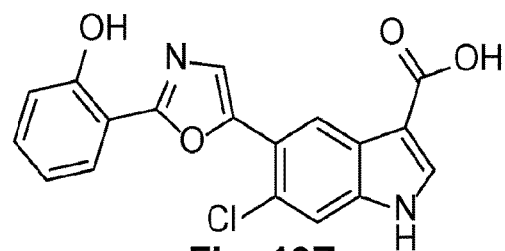

Results: FIG. 13F illustrates 6-chloro-5-(5-(1-(hydroxymethyl)cyclopropyl)thiophen-2-yl)-1H-indole-3-carboxylic acid which has $^1$H NMR (400 MHz, DMSO-d6): δ 11.65 (bs, 1H), 8.24 (bs, 1H), 7.89 (bs, 1H), 7.55 (d, J=9.2 Hz, 1H), 705 (s, 1H), 6.88 (d, J=3.6 Hz, 1H), 4.90 (s, 1H), 3.57 (s, 2H), 1.00-0.87 (m, 4H) and LCMS: 99.06% (465.30 [M+H]$^+$).

Figure 14L:
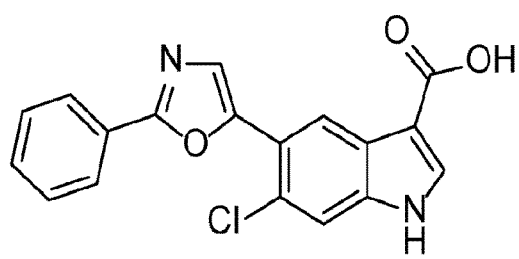

FIG. 14L illustrates 6-chloro-5-(2-phenyloxazol-5-yl)-1H-indole-3-carboxylic acid, which has $^1$H NMR (400 MHz, DMSO) δ 12.08 (s, 2H), 8.53 (s, 1H), 8.13 (s, 1H), 8.06 (d, J=6.6 Hz, 2H), 7.81 (s, 1H), 7.72 (s, 1H), 7.59 (t, J=7.1 Hz, 3H), LCMS: 91.95% (339.35 [M+H]$^+$), and Melting range: 261-265° C.

Figure 14M:
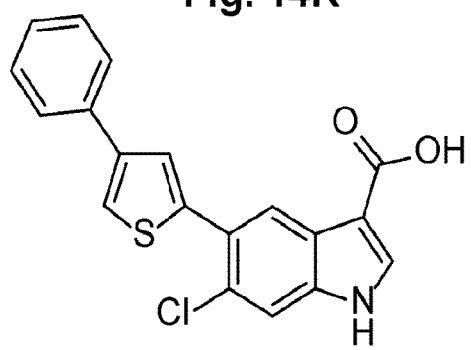

FIG. 14M illustrates 6-chloro-5-(4-phenylthiophen-2-yl)-1H-indole-3-carboxylic acid which has $^1$H NMR (400 MHz, DMSO-d6): δ 11.77 (bs, 1H), 8.31 (s, 1H), 7.91 (s, 1H), 7.88 (s, 1H), 7.76 (d, J=7.6 Hz, 2H), 7.66 (d, J=1.2 Hz, 1H), 7.61 (s, 1H), 7.43 (t, 2H), 7.31 (t, 1H), LCMS: 99.55% (354.10 [M+H]$^+$) and Melting range: 195-199° C.

Conclusion: Embodiments are capable of synthesizing novel AMPK agonists and derivates thereof, such as those illustrated in FIGS. 13A-13Z and FIGS. 14A-14O.

Example 10: Synthesizing Additional Analogs of EV8016 (FIG. 13A)

Background: FIG. 12A illustrates a generalized structure of a compound capable of activating AMPK. The synthesis of additional derivatives (FIGS. 14N-14O) are described in this example.

Methods: A graphical illustration of this example is illustrated in FIG. 12D, and while this example illustrates the synthesis of the compounds illustrated in FIGS. 14N-14O, one of skill in the art would understand the use of different reagents, reactants, conditions, etc. to generate derivative compounds, including those illustrated in FIGS. 13A-13Z and FIGS. 14A-14O.

Figure 14N:
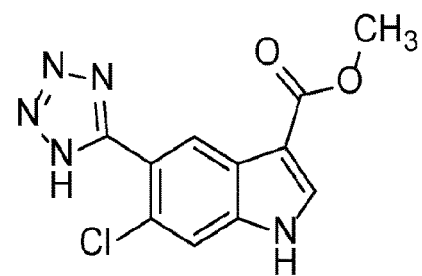

Results: FIG. 14N illustrates methyl 6-chloro-5-(1H-tetrazol-5-yl)-1H-indole-3-carboxylate, which is the product after Step 2 of FIG. 12D. This compound has $^1$H NMR (400 MHz, DMSO-d6): δ 12.03 (br s, 1H), 8.25 (s, 1H), 8.15 (s, 1H), 7.60 (s, 1H), 7.01-7.00 (br s, 1H), 3.81 (s, 3H), and LCMS: 93.9% (278.07 [M+H]$^+$).

Figure 14O:
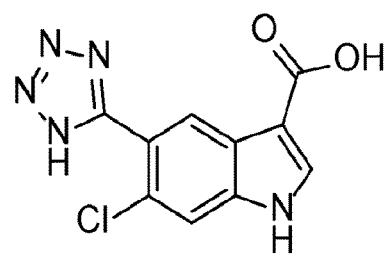

FIG. 14O illustrates 6-chloro-5-(1H-tetrazol-5-yl)-1H-indole-3-carboxylic acid, which a product of Step 3 of FIG. 12D. This compound has $^1$H NMR (400 MHz, DMSO-d6): δ 16.73 (s, 1H), 12.34 (s, 1H), 12.21 (s, 1H), 8.36 (s, 1H), 8.19 (d, J=2.9 Hz, 1H), 7.78 (s, 1H) and melting range: 268-272° C.

Conclusion: Embodiments are capable of synthesizing novel AMPK agonists and derivates thereof, such as those illustrated in FIGS. 13A-13Z and FIGS. 14A-14O.

Example 11: Synthesizing (3R,3aR,6R,6aR)-6-((5-([1,1'-biphenyl]-4-yl)-1H-naphtho[1,2-d]imidazol-2-yl)oxy)hexahydrofuro[3,2-b]furan-3-ol Methods: A graphical illustration of this example is shown in FIG. 15A. Additionally, while this example illustrates the synthesis of the compound illustrated in FIG. 15B, one of skill in the art would understand the use of different reagents, reactants, conditions, etc. to generate derivative compounds.

Step 1: Synthesizing N-(4-bromonaphthalen-1-yl)acetamide (Compound 2)—To a stirred solution of Compound-1 (5.0 g, 22.520 mmol) in Methanol, was added Acetic acid (4.2 mL, 45.040 mmol), at RT and the reaction mixture was allowed to stir at 70° C. for 2 h. The reaction progress was monitored by TLC. Upon completion, reaction mixture was poured into ice cold water and the precipitated solid was filtered off, dried under vacuo to afford compound-2 as a yellow solid (4.5 g, 75%).

Step 2: Synthesizing N-(4-bromo-2-nitronaphthalen-1-yl)acetamide (Compound 3)—To a stirred solution of Compound-2 (4.0 g, 15.150 mmol) in acetic acid (40 mL) at room temperature, was added Fuming HNO$_3$ (0.72 mL, 16.660 mmol) and the reaction mixture was stirred at 75° C. for 2 h. The reaction progress was monitored by TLC. Upon completion, reaction mixture was poured into ice cold water, precipitated solid was filtered off, washed with plenty of water and dried under vacuo to afford compound-3 as yellow solid (3.52 g, 72%).

Step 3: Synthesizing N-(4-([1,1'-biphenyl]-4-yl)-2-nitronaphthalen-1-yl)acetamide (Compound 5):

To a stirred solution of Compound-3 (20.0 g, 64.720 mmol) and Compound-4 (19.2 g, 97.080 mmol) in Dioxane and Water (9:1), was added K2CO3 (22.30 g, 161.800 mmol), the reaction mixture was purged for 15 min with nitrogen, then added Pd(PPh3)4 (3.73 g, 3.230 mmol) and again purged for 10 min with nitrogen, then the reaction mixture was stirred at 90° C. for 2 h. The reaction progress was monitored by TLC. Upon completion of reaction, reaction mixture was filtered through Celite, filtrate was concentrated under reduced pressure, residue was triturated with water and the precipitated solid was filtered. Solid was recrystallized from 2-propanol, obtained solid was filtered and dried under vacuo to afford compound-5 as yellow solid (11.1 g, 40%). Compound 5 was used as such in Step 6.

Step 4: Synthesizing 4-([1,1'-biphenyl]-4-yl)-2-nitronaphthalen-1-amine (Compound 6)—To a stirred solution of Compound-5 (5.0 g, 13.089 mmol) in 1, 4 Dioxane (500 mL), was added Conc. HCl (50 mL) and the reaction mixture was stirred at 100° C. for 48 h. The reaction progress was monitored by TLC. Upon completion of reaction, Dioxane was evaporated under reduced pressure, the aqueous residue was diluted with ice cold water and the precipitated solid was filtered. The solid was washed with plenty of water and dried under vacuo to afford compound-6 (4.05 g, 91.0%) as yellow solid. This compound was used in the next step without further purification.

Step 5: Synthesizing 4-([1,1'-biphenyl]-4-yl)naphthalene-1,2-diamine (Compound 7)—To a solution of compound-6 (5.0 g, 14.662 mmol) and in a mixture of THF (400 mL) and Ethanol (100 mL), were added 10% w/w wet Pd-C (1.0 g,) the resulting reaction mixture was hydrogenated in a Parr apparatus, under 80 psi pressure of hydrogen for 16 h at RT. The progress of the reaction was monitored by TLC. After completion of reaction, filtered through Celite and the filtrate was concentrated under reduced pressure. The crude product was triturated with n-pentane and precipitated solid was filtered, dried under vacuo to afford compound-7 as a yellow solid (3.5 g crude). This compound was used a such immediately in the next step.

Step 6: Synthesizing 5-([1,1'-biphenyl]-4-yl)-1,3-dihydro-2H-naphtho[1,2-d]imidazole-2-thione (Compound 8)—To a stirred solution of Compound-7 (3.5 g, 11.290 mmol) in THF (70 mL), was added DMAP (2.75 g 22.80 mmol) followed by thiophosgene (0.89 mL, 11.290 mmol) at 0° C. and the resulting reaction mixture was stirred for 3 h at RT. Reaction progress was monitored by TLC. Upon completion of reaction, solvent was evaporated under reduced pressure, residue was partitioned between ethyl acetate and water. Organic layer was washed with brine, dried over anhydrous Na$_2$SO$_4$, filtered and concentrated under reduced pressure to afford crude compound-8 (3.2 g) as a yellow solid.

Step 7: Synthesizing 5-([1,1'-biphenyl]-4-yl)-2-(methylthio)-1H-naphtho[1,2-d]imidazole (Compound 9)—To a stirred solution of Compound-8 (3.0 g, 8.522 mmol) in Acetone (100 mL), was added K$_2$CO$_3$ (1.41 g, 10.226 mmol) at 0° C., stirred for 10-15 min, was added Methyl iodide (0.55 mL, 8.522 mmol) and the resulting reaction mixture was allowed to stir for 3 h at RT. Reaction progress was monitored by TLC. Upon completion of reaction, solvent was evaporated under reduced pressure and the residue was partitioned between ethyl acetate and water. Organic layer was washed with brine, dried over anhydrous Na$_2$SO$_4$, filtered and concentrated under reduced pressure to afford crude. The crude was purified by Flash chromatography (230×400 mesh, 15-20% EA in PE) to afford 1.1 g (35.3%) compound-9 as a yellow solid.

Step 8: Synthesizing 5-([1,1'-biphenyl]-4-yl)-2-(methylsulfonyl)-1H-naphtho[1,2-d]imidazole (Compound 10)—To a stirred solution of Compound-9 (1.0 g, 2.732 mmol) in dichloromethane (30 mL), was added 3-Chloro perbenzoic acid (1.41 g, 8.196 mmol) at 0° C. and the resulting reaction mixture was stirred for 2 h at RT.

Reaction progress was monitored by TLC. Upon completion of reaction, reaction mixture was diluted with dichloromethane, washed with 10% aqueous NaHCO$_3$ solution, 10% sodium thiosulphate solution followed by brine. Organic layer was dried over anhydrous Na$_2$SO$_4$, filtered and concentrated under reduced pressure to afford 3.5 g of crude yellow solid compound 10.

Step 9: Synthesizing 5-([1,1'-biphenyl]-4-yl)-2-(methylsulfonyl)-1-((2-(trimethylsilyl)ethoxy)methyl)-1H-naphtho[1,2-d]imidazole (Compound 11)—To a stirred solution of Compound-10 (1.3 g, 3.266 mmol) in dichloromethane (50 mL), was added Triethylamine (0.68 mL, 4.899 mmol) followed by SEM chloride (0.65 g, 3.919 mmol), at 0° C. and the resulting reaction mixture was stirred for 2 h at RT. Reaction progress was monitored by TLC. Upon completion of reaction, diluted with dichloromethane, washed with 10% aqueous NaHCO$_3$ solution, followed by brine. Organic layer was dried over anhydrous Na$_2$SO$_4$, filtered and concentrated under reduced pressure. The crude product was purified by Flash chromatography (230×400 mesh, 10-15% EA in PE) to afford compound-11 (0.35 g, 20%).

Step 10: Synthesizing 5-([1,1'-biphenyl]-4-yl)-2-(((3R,3aR,6R,6aS)-6-((tert-butyldimethylsilyl)oxy)hexahydrofuro[3,2-b]furan-3-yl)oxy)-1-((2-(trimethylsilyl)ethoxy)methyl)-1H-naphtho[1,2-d]imidazole (13)—To a stirred solution of Compound-12 (0.34 g, 1.325 mmol) in Tetrahydrofuran (5 mL), was added Potassium tert-butoxide (0.15 g, 1.325 mmol) at 0° C. and the resulting reaction mixture was stirred for 1 h at 0° C. To this reaction mixture, was added the solution of Compound-11 in Tetrahydrofuran at 0° C. and the resulting reaction mixture was allowed to stir at RT for 2 h. Reaction progress was monitored by TLC. Upon completion of reaction, solvent was evaporated under reduced pressure and the residue was partitioned between ethyl acetate and water. Organic layer was washed with brine, dried over anhydrous Na$_2$SO$_4$, filtered and concentrated under reduced pressure to afford crude compound-13 (0.6 g) as a brown gummy solid.

Step 11: Synthesizing (3R,3aR,6R,6aR)-6-((5-([1,1'-biphenyl]-4-yl)-1H-naphtho[1,2-d]imidazol-2-yl)oxy)hexahydrofuro[3,2-b]furan-3-ol (Compound EV8017)—To a stirred solution of Compound-13 (0.6 g, 0.846 mmol) in Formic acid (12 mL), was added solution of KHSO$_4$ (0.11 g, 0.846 mmol) in water (1.0 mL) and the resulting reaction mixture was stirred for 16 h at 60° C. Reaction progress was monitored by TLC and LCMS. Upon completion of reaction, cooled to 0° C., basified with 2N aqueous NaOH solution by adjusting pH to 12-13, stirred the solution at 0° C. for further 1 h, neutralized with 2N HCl and extracted with ethyl acetate. Combined organic layer was washed with brine, dried over anhydrous Na$_2$SO$_4$, filtered and concentrated under reduced pressure. Crude product was purified by Flash chromatography (C-18 column, 80% MeOH in Water) to afford compound-EV8017 as off white solid (0.14 g, 35.7%).

Results: Step 1 produced Compound 2 with the following characteristics: LCMS: 98.8% (266.06 M+H$^+$ & 264.06 M−H$^+$); $^1$H NMR (400 MHz, CDCl$_3$): δ 8.31 (d, J=8.4 Hz, 1H), 7.88 (d, J=8.0 Hz, 1H), 7.82-7.80 (m, 2H), 7.67-7.61 (m, 2H), 7.47 (br s, 1H), 2.36 (s, 3H).

Step 2 produced Compound 3 with the following characteristics: LCMS: 94.0% (309.12 M−H$^+$); $^1$H NMR (400 MHz, CDCl$_3$): δ 8.72 (br s, 1H), 8.38 (s, 1H), 8.30 (d, J=8.4 Hz, 1H), 8.06 (d, J=8.4 Hz, 1H), 7.82-7.78 (m, 1H), 7.71-7.67 (m, 1H), 2.37 (s, 3H).

Step 3 produced Compound 5 with the following characteristics: LCMS: 91.85% (381.31 M−H$^+$).

Step 4 produced Compound 6 with the following characteristics: LCMS: 90.48% (341.29, M+H$^+$).

Step 5 produced Compound 7 with the following characteristics: LCMS: 52.0% (311.3 [M+H]$^+$).

Step 6 produced Compound 8 with the following characteristics: LCMS: 52.0% (353.2 [M+H]$^+$).

Step 7 produced Compound 9 with the following characteristics: LCMS: 77.6.0% (367.29 [M+H]$^+$).

Step 8 produced Compound 10 with the following characteristics: LCMS: 76.9% (397.29 [M−H]$^+$).

Step 9 produced Compound 11 with the following characteristics: LCMS: 88.0% (529.40 [M+H]$^+$); $^1$H NMR (400 MHz, CDCl$_3$): δ 8.75 (d, J=7.6 Hz, 1H), 8.00 (s, 1H), 7.75 (d, J=6.4 Hz, 2H), 7.71 (m, 3H), 7.67 (s, 1H), 7.60 (d, J=8.4 Hz, 1H), 7.54-7.40 (m, 4H), 6.04 (s, 2H), 3.70 (t, J=8.0 Hz, 2H), 0.93 (t, J=8.0 Hz, 2H), −0.47 (s, 9H).

Step 10 produced Compound 13 with the following characteristics: LCMS: 84.8% (709.70 [M+H]$^+$).

Step 11 produced Compound EV8017 with the following characteristics: LCMS: 99.89% (465.30 [M+H]$^+$); HPLC: 99.86%; m.p.; 158-162° C. $^1$H NMR (400 MHz, DMSO-d6): δ 13-12 (br s, 1H), 8.29 (br s, 1H), 7.87 (d, J=8.4 Hz, 1H), 7.83-7.77 (m, 4H), 7.59-7.50 (m, 6H), 7.42-7.35 (m, 2H), 5.52 (d, J=5.6 Hz, 1H), 4.98 (d, J=6.8 Hz, 1H), 4.89 (t, J=4.8 Hz, 1H), 4.41 (t, J=4.8 Hz, 1H), 4.23-4.16 (m, 2H), 3.88 (q, J=6.8 Hz, 1H), 3.82 (t, J=6.8 Hz, 1H), 3.48 (t, J=8.4 Hz, 1H).

Conclusion: Embodiments are capable of synthesizing novel AMPK agonists and derivates thereof, such as those illustrated in FIG. 15B.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:
1. A compound of formula:

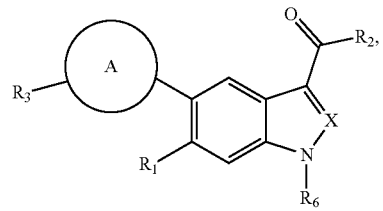

wherein:
A is selected from

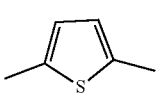 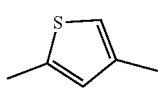 and

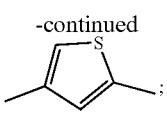

X is CR$_5$ or N;
R$_1$ is H, CF$_3$, or halo;
R$_2$ is OR$_5$, NHOH, NHSO$_2$R$_4$, or OCH$_2$OCOR$_4$, or COR$_2$ is a C-linked tetrazole,
R$_3$ is C$_{1-10}$ alkyl, C$_{3-7}$ cycloalkyl, C$_{4-12}$ alkylcycloalkyl, C$_{4-10}$ cycloalkylalkyl, C$_{3-7}$ heterocycloalkyl, C$_{4-12}$ alkylheterocycloalkyl, C$_{4-10}$ heterocycloalkylalkyl, aryl or heteroaryl either unsubstituted or substituted with one to three substituents selected from halo, OH and OCOR$_7$;
R$_4$ is C$_{1-10}$ alkyl, C$_{3-7}$ cycloalkyl, C$_{4-12}$ alkylcycloalkyl, C$_{4-10}$ cycloalkylalkyl either unsubstituted or substituted with one to three halogen substituents;
R$_5$ is R$_4$ or H;
R$_6$ is H, C$_{1-6}$ alkyl, C$_{3-6}$ cycloalkyl, or two R$_6$ groups, together with the nitrogen atom to which they are attached can form a four to seven membered heterocycloalkyl ring, all of which can be optionally substituted with 1 to 3 fluorine atoms; and
R$_7$ is C$_{1-10}$ alkyl, C$_{3-7}$ cycloalkyl, C$_{4-12}$ alkylcycloalkyl unsubstituted or substituted with one to three substituents selected from fluoro, C$_{1-10}$ alkyl, and NR$_6$R$_6$.

2. The compound of claim 1, wherein X is CH, R$_6$ is H, R$_1$ is Cl, and R$_2$ is OH.

3. The compound of claim 1, wherein the compound is selected from:

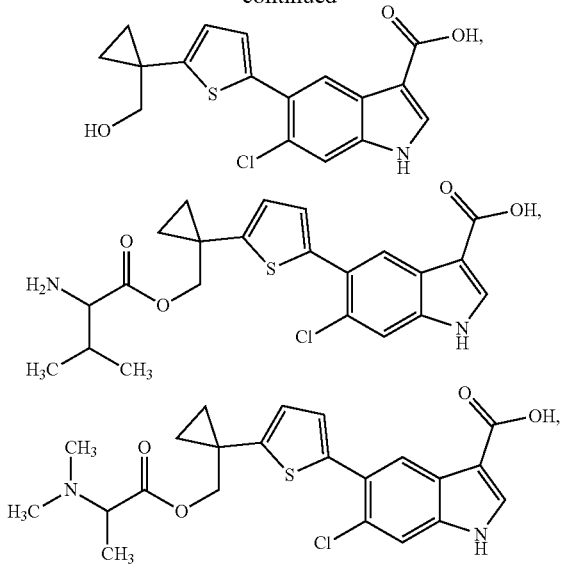

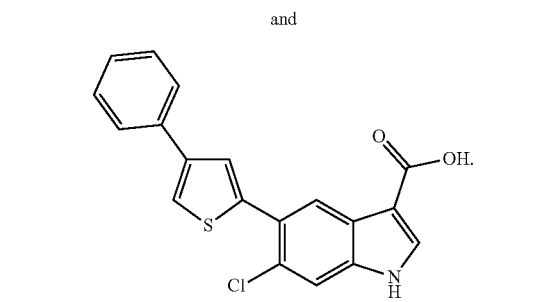

4. The compound of claim 1, wherein the compound is:

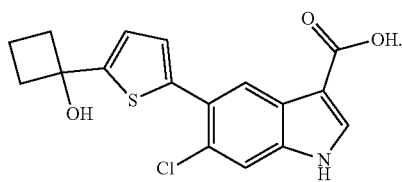 [SMILES: O=C(O)c1c[nH]c2cc(Cl)c(-c3ccc(C4(O)CCC4)s3)cc12]

5. The compound of claim 1, wherein R$_1$ is Cl.
6. The compound of claim 1, wherein R$_2$ is OH.
7. The compound of claim 1, wherein X is CH.
8. The compound of claim 1, wherein R$_3$ is selected from:

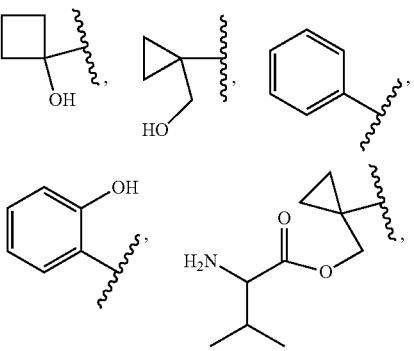

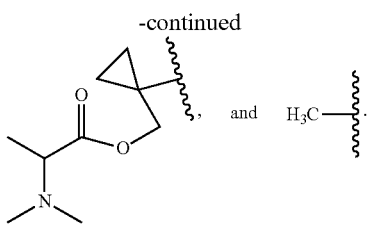

9. A pharmaceutical formulation comprising the compound of claim 1.

10. A method of treating a patient with mitochondrial dysfunction comprising:
administering a compound of claim 1, to the patient,
wherein the mitochondrial dysfunction is selected from the group consisting of Autosomal Dominant Optic Atrophy, Alpers-Huttenlocher syndrome, Barth syndrome/Lethal Infantile Cardiomyopathy, Co-enzyme Q deficiency, Complex I deficiency, Complex II deficiency, Complex Ill deficiency, Complex IV deficiency, Complex V deficiency, Chronic progressive external ophthalmoplegia, Kearns-Sayre syndrome, Leigh syndrome, Leber's hereditary optic neuropathy, Luft Disease, MELAS syndrome, Mitochondrial Enoyl CoA Reductase Protein-Associated Neurodegeneration, Myoclonic epilepsy with ragged red fibers, mitochondrial recessive ataxia syndrome, Mitochondrial neurogastrointestinal encephalopathy syndrome, NARP syndrome, Pearson syndrome, Pyruvate dehydrogenase complex deficiency, DNA polymerase gamma deficiency, Pyruvate carboxylase deficiency, Thymidine kinase 2 deficiency, Amyotrophic Lateral Sclerosis, Alzheimer's disease, Friedreich's ataxia, Huntington's disease, N-glycanase deficiency, Parkinson's disease, Spinal muscular atrophy, Spinocerebellar ataxia, Becker muscular dystrophy, Duchenne muscular dystrophy, Emery-Dreifuss muscular dystrophy, Facioscapulohumeral muscular dystrophy, Myotonic dystrophy, Oculopharyngeal muscular dystrophy, Charcot-Marie-Tooth disease, hyperthyroid myopathy, hypothyroid myopathy, Giant axonal neuropathy, Hereditary spastic paraplegia, dermatomyositis, inclusion-body myositis, polymyositis, Chronic fatigue syndrome, and age-related macular degeneration.

11. The method of claim 10, wherein the mitochondrial dysfunction is age-related macular degeneration.

12. The method of claim 10, wherein the compound is provided in a pharmaceutical formulation that comprises the compound and at least one selected from a binding agent, a lubricating agent, a buffer, and a coating.

13. The method of claim 10, wherein the administering is daily for at least one week.

14. The method of claim 10, further comprising assessing the efficacy of the compound in the patient.

15. The method of claim 10, wherein the administering the compound is selected from the group consisting of: oral administration, subcutaneous administration, intravenous administration, intraperitoneal administration, intranasal administration, dermal administration, intravitreal injection, and inhalation.

16. The compound of claim 1, wherein the compound is:

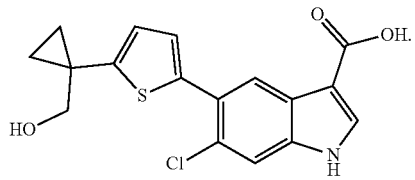 [SMILES: O=C(O)c1c[nH]c2cc(Cl)c(-c3ccc(C4(CO)CC4)s3)cc12]

17. The compound of claim 1, wherein the compound is:

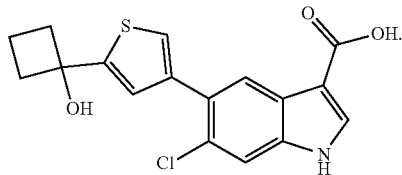 [SMILES: O=C(O)c1c[nH]c2cc(Cl)c(-c3csc(C4(O)CCC4)c3)cc12]

* * * * *